US006372726B1

(12) United States Patent
Slusher et al.

(10) Patent No.: US 6,372,726 B1
(45) Date of Patent: *Apr. 16, 2002

(54) METHODS OF CANCER TREATMENT USING NAALADASE INHIBITORS

(75) Inventors: Barbara S. Slusher, Kingsville; Paul F. Jackson, Bel Air; Kevin L. Tays, Elkridge; Keith M. Maclin, Baltimore, all of MD (US)

(73) Assignee: Guilford Pharmaceuticals Inc., Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/405,842

(22) Filed: Sep. 27, 1999

Related U.S. Application Data

(60) Division of application No. 08/864,545, filed on May 28, 1997, now Pat. No. 6,011,021, which is a continuation-in-part of application No. 08/665,775, filed on Jun. 17, 1996, now Pat. No. 5,804,602.

(51) Int. Cl.$^7$ .............................. A61K 31/66; C07F 9/02
(52) U.S. Cl. ................ 514/75; 562/8; 562/12; 514/908
(58) Field of Search ............. 514/908, 75; 562/8, 562/12

(56) References Cited

U.S. PATENT DOCUMENTS

| | | |
|---|---|---|
| 3,472,932 A | 10/1969 | Shindo et al. ............. 424/210 |
| 4,151,172 A | 4/1979 | Ondetti et al. ............ 26/326.2 |
| 4,168,267 A | 9/1979 | Petrillo, Jr. |
| 4,316,896 A | 2/1982 | Thorsett et al. |
| 4,337,201 A | 6/1982 | Petrillo, Jr. |
| 4,374,131 A | 2/1983 | Petrillo, Jr. |
| 4,444,765 A | 4/1984 | Karanewsky et al. |
| 4,448,772 A | 5/1984 | Karanewsky |
| 4,452,790 A | 6/1984 | Karanewsky et al. |
| 4,452,791 A | 6/1984 | Ryono et al. |
| 4,468,519 A | 8/1984 | Krapcho |
| 4,547,324 A | 10/1985 | Wong et al. |
| 4,555,506 A | 11/1985 | Karanewsky et al. |
| 4,560,680 A | 12/1985 | Ryono et al. |
| 4,560,681 A | 12/1985 | Karanewsky |
| 4,567,166 A | 1/1986 | Karanewsky et al. |
| 4,616,005 A | 10/1986 | Karanewsky et al. |
| 4,671,958 A | 6/1987 | Rodwell et al. |
| 4,703,043 A | 10/1987 | Karanewsky et al. |
| 4,715,994 A | 12/1987 | Parsons et al. |
| 4,716,155 A | 12/1987 | Karanewsky et al. |
| 4,741,900 A | 5/1988 | Alvarez et al. |
| 4,849,525 A | 7/1989 | Weller, III et al. |
| 4,853,326 A | 8/1989 | Quash et al. |
| 4,867,973 A | 9/1989 | Goers et al. |
| 4,885,283 A | 12/1989 | Broadhurst et al. |
| 4,906,779 A | 3/1990 | Weber et al. |
| 4,918,064 A | 4/1990 | Cordi et al. |
| 4,937,183 A | 6/1990 | Ultee et al. |
| 4,950,738 A | 8/1990 | King et al. |
| 4,959,493 A | 9/1990 | Ohfume et al. |
| 4,962,097 A | 10/1990 | Parsons et al. |
| 4,966,999 A | 10/1990 | Coughlin |
| 4,988,681 A | 1/1991 | Ishikawa et al. |
| 4,994,446 A | 2/1991 | Sokolovsky et al. |
| 5,030,732 A | 7/1991 | Morita et al. |
| 5,041,644 A | 8/1991 | Morita et al. |
| 5,047,227 A | 9/1991 | Rodwell et al. |
| 5,061,806 A | 10/1991 | Morita et al. |
| 5,093,525 A | 3/1992 | Weber et al. |
| 5,099,063 A | 3/1992 | Parsons et al. |
| 5,136,080 A | 8/1992 | Miller et al. |
| 5,140,104 A | 8/1992 | Couglin et al. |
| 5,143,908 A | 9/1992 | Parsons et al. |
| 5,145,990 A | 9/1992 | Parsons et al. |
| 5,147,867 A | 9/1992 | Parsons et al. |
| 5,156,840 A | 10/1992 | Goers et al. |
| 5,162,504 A | 11/1992 | Horoszewicz |
| 5,162,512 A | 11/1992 | King et al. |
| 5,190,976 A | 3/1993 | Weber et al. |
| 5,196,510 A | 3/1993 | Rodwell et al. |
| 5,242,915 A | 9/1993 | Ueda et al. |
| 5,262,568 A | 11/1993 | Weber et al. |
| H1312 H | 5/1994 | Coughlin et al. |
| 5,326,856 A | 7/1994 | Coughlin et al. |
| 5,336,689 A | 8/1994 | Weber et al. |
| 5,449,761 A | 9/1995 | Belinka, Jr. et al. |
| 5,474,547 A | 12/1995 | Aebishcher et al. |
| 5,489,525 A | 2/1996 | Pastan |
| 5,495,042 A | 2/1996 | Belinka, Jr. et al. |
| 5,500,420 A | 3/1996 | Maiese ................ 514/131 |
| 5,508,273 A | 4/1996 | Beers et al. |
| 5,527,885 A | 6/1996 | Coughlin et al. |
| 5,538,866 A | 7/1996 | Israeli et al. ............. 435/69.3 |
| 5,538,957 A | 7/1996 | Tsaklidis et al. .......... 514/114 |
| 5,594,007 A | 1/1997 | Chenard |
| 5,672,592 A * | 9/1997 | Jackson et al. ............. 514/75 |
| 5,698,402 A | 12/1997 | Luderer et al. |

(List continued on next page.)

OTHER PUBLICATIONS

Pudovik, A.N. et al., "Reaction of Partial Esters of Phosphorus Acids with Ethyl Benzoylformate, " *Chemical Abstracts*, (1969) Abstract No. 69:87,915u, *Zh. Obshch. Khim.* (1969) 1968, 38(7), 1539–45 (Russ.).

Pudovik, A.N. et al., "Reactions of Ethyl Hydrogen Phenylphosphonite with Esters of α–Oxocarboxylic and α–Oxophosphonic Acids," *Chemical Abstracts*, (1969) Abstract No. 71:61, 476x, *Zh. Obshch. Khim.* (1960) 39(5), 1021–7 (Russ.).

Shindo, N. et al., "O–alkyl (S–alkoxycarbonyl) (phenyl) methyl phenyltiophosphonate," *Chemical Abstracts*, (1970) Abstract No. 73:25, 664q, 1970. Japan 70–03772.

(List continued on next page.)

*Primary Examiner*—Charanjit S. Aulakh
(74) *Attorney, Agent, or Firm*—Lyon & Lyon LLP

(57) ABSTRACT

The present disclosure relates to dipeptidase inhibitors, and more particularly, to novel methods of using phosphonate derivatives, hydroxyphosphinyl derivatives, and phosphoramidate derivatives to inhibit N-Acetylated α-Linked Acidic Dipeptidase (NAALADase) enzyme activity, and to treat prostate diseases, especially using the compounds of the present invention for the inhibition of the growth of prostate cancer cells.

12 Claims, 6 Drawing Sheets

U.S. PATENT DOCUMENTS

| | | | | |
|---|---|---|---|---|
| 5,804,602 A | * | 9/1998 | Slusher et al. | 514/574 |
| 5,880,112 A | * | 3/1999 | Jackson et al. | 514/121 |
| 5,968,915 A | * | 10/1999 | Jackson et al. | 514/89 |
| 6,025,344 A | * | 2/2000 | Jackson et al. | 514/75 |
| 6,025,345 A | * | 2/2000 | Jackson et al. | 514/75 |
| 6,046,180 A | * | 4/2000 | Jackson et al. | 514/75 |

OTHER PUBLICATIONS

Campbell, D.A., "The Synthesis of Phosphonate Esters, an Extension of the Mitsunobu Reaction," *Journal of Organic Chemistry*, (1992) 57:6331–6335.

Vornov, J. et al., "Toxic NMDA–receptor activation occurs during recovery in a tissue culture model of ischemia," *J. of Neurochemistry*, 65, pp. 1681–1691 (1995).

Slusher, B. et al., "Rat brain N–acetylated α–linked acidic dipeptidase activity," *The J. of Biological Chemistry*, Vol. 265, No. 34, pp. 21297–21301, (1990).

Slusher, B. et al., "Immunocytochemical localization of the N–acetyl–aspartyl–glutamate (NAAG) hydrolyzing enzyme N–acetylated α–linked acidic dipeptidase (NAALADase)," *J. of Comp. Neurology*, 315, pp. 217–229 (1992).

Slusher, B. et al., "NAALADase: A Potential Regulator of Synaptic Glutamate," *Biotech Update DuPont NEN*, 9, pp. 37–39 (1994).

Jackson, P. et al., "Design, synthesis, and biological activity of a potent inhibitor of the neuropeptidase N–acetylated α–linked acidic dipeptidase," *J. of Medicinal Chemistry*, (1995) 39:2, 619–622.

Carter, R. et al., "Prostate–specific membrane antigen is a hydrolase with substrate and pharmacologic characteristics of neuropeptidase," *Proc. Nat. Acad. Sci.*, 93, pp. 749–753 (1996).

Heston, W.D.W., "Potential Uses of Prostate Specific Membrane Antigen (PSMA) : A Neurocarboxypeptidase and Membrane Folate Hydrolase," *Urologe* [A], v. 35, pp. 400–407 (1996).

Hurn, P., "Gender–Linked Injury After Focal Cerebral Ischemia," *Society for Neuroscience 1996 Abstract Form*, (1996).

Bhardwaj, A. et al., "Striatal nitric oxide (NO) production is enhanced in focal cerebral ischemia: An in vivo microdialysis study," *Soc. For Neuropscience 1996 Abstract Form*, (1996).

Stauch, B. et al., "The effects of N–acetylated alpha linked acidic dipeptidase (NAALADase), inhibitors on[$^3$H]NAAG catabolism in vivo," *Neuroscience Letters*, 100, pp. 295–300 (1989).

Meyerhoff, J. et al., "Activity of a NAAG–hydrolyzing enzyme in brain may affect seizure susceptibility in genetically epilepsy–prone rats," *Molecular Neurobiology of Epilepsy*, pp. 163–172 (1992).

Subasinghe, N. et al., "Synthesis of Acyclic and Dehydroaspartic Acid Analogues of Ac–Asp–Glu–Oh and Their Inhibition of Rat Brain N–acetylated α–linked Acidic Dipeptidase (NAALA Dipeptidase)," *J. Med. Chem.*, 33, pp. 2734–2744, (1990).

Coyle, J. et al., "N–acetyl–aspartyl glutamate," *Excitatory Amino Acids*, pp. 69–77 (1990).

Tsai, G. et al., "Reductions in acidic amino acids and N–acetylaspartylglutamate in amyotrophic lateral sclerosis," *Brain Research*, 556, pp. 151–161 (1991).

Tsai, G. et al., "Changes of excitatory neurotransmitter metabolism in schizophrenic brains," *Salmon Lecturer of the New York Academy of Medicine*, (Dec. 2–3, 1993).

Rothstein, J. et al., "Abnormal excitatory amino acid metabolism in amyotrophic lateral sclerosis," *Anals of Neurology*, vol. 28, pp. 18–25 (1990).

Tsai, G. et al., "Immunocytochemical distribution of N–acetylaspartylglutamate in the rat forebrain and glutamergic pathways," *J. of Chem. Neuroanatomy*, 6, p. 277–292 (1993).

Koenig, M. et al., "N–acetyl–aspartyl–glutamate (NAAG), elicits rapid increase in intraneuronal $Ca^{2+}$ in vitro," *NeuroReports*, 5, pp. 1063–1068 (1994).

Carter, R, et al., "Prostate–specific membrane antigen is a hydrolase with substrate and pharmacologic characteristics of neuropeptidase," *Proc. Nat. Acad. Sci.*, 93, pp. 749–753 (1996).

Meyerhoff, J. et al., "Genetically epilepsy–prone rats have increased brain regional activity of an enzyme which liberates glutamate from N–acetyl–aspartyl–glutamate," *Brain Research*, 593, pp. 140–143 (1992).

Woods, D. et al., "Gender–linked injury after focal cerebral ischemia," *Soc. For Neuroscience 1996 Abstract Form*, (1996).

\* cited by examiner

METHODS OF CANCER TREATMENT USING NAALADASE INHIBITORS

RELATED APPLICATIONS

This application is a divisional of U.S. patent application Ser. No. 08/864,545, filed May 28, 1997 now U.S. Pat. No. 6,011,021, entitled "Methods of Cancer Treatment Using NAALADase Inhibitors".

This application is a continuation-in-part (CIP) of U.S. patent application Ser. No. 08/665,775, filed Jun. 17, 1996 now U.S. Pat. No. 5,804,602, entitled "Methods of Cancer Treatment Using NAALADase Inhibitors".

BACKGROUND OF THE INVENTION

1. Field of the Invention

The present invention relates to novel methods of treating cancer, preventing tumor cell growth, inhibiting prostate tumor cell growth, and inhibiting NAALADase enzyme activity, by administering an effective amount of a NAALADase inhibitor.

2. Description of the Prior Art

Prostate Cancer

Prostate cancer is the leading form of cancer and the second leading cause of death from cancer for men in the United States. The American Cancer Society has estimated that in 1996 alone, 317,100 new cases of prostate cancer were diagnosed and 41,400 deaths were caused by prostate cancer. The incidence rate of prostate cancer increased 65% between 1980 and 1990, and will continue to rise with improved screening tests and longer life expectancies. While most men used to die of other illnesses before prostate cancer had a chance to develop, higher prostate cancer mortality rates are expected as men live longer and the disease has more time to progress.

In 1993, the molecular cloning of Prostate Specific Membrane Antigen (PSMA) was reported as a potential prostate carcinoma marker and hypothesized to serve as a target for imaging and cytotoxic treatment modalities for prostate cancer. PSMA antibodies, particularly indium-111 labelled and tritium labelled PSMA antibodies, have been described and examined clinically for the diagnosis and treatment of prostate cancer. PSMA is expressed in prostatic ductal epithelium and is present in seminal plasma, prostatic fluid and urine. In 1996, it was found that the expression of PSMA cDNA confers the activity of NAALADase.

NAALADase Inhibitors

NAAG and NAALADase have been implicated in several human and animal pathological conditions relating to glutamate abnormalities and neurotoxicity. For example, it has been demonstrated that intra-hippocampal injections of NAAG elicit prolonged seizure activity. More recently, it was reported that rats genetically prone to epileptic seizures have a persistent increase in their basal level of NAALADase activity. These observations lend support the hypothesis that increased availability of synaptic glutamate elevates seizure susceptibility, and suggest that NAALADase inhibitors may provide anti-epileptic activity.

NAAG and NAALADase have also been implicated in the pathogenesis of ALS and in the pathologically similar animal disease called Hereditary Canine Spinal Muscular Atrophy (HCSMA). It has been shown that concentrations of NAAG and its metabolites—NAA, glutamate and aspartate—are elevated two- to three-fold in the cerebrospinal fluid of ALS patients and HCSMA dogs. Additionally, NAALADase activity is significantly increased (two- to three-fold) in post-mortem spinal cord tissue from ALS patients and HCSMA dogs. As such, NAALADase inhibitors might be clinically useful in curbing the progression of ALS if an increased metabolism of NAAG is responsible for the alterations of CSF levels of these acidic amino acids and peptides.

Abnormalities in NAAG levels and NAALADase activity have also been documented in post-mortem schizophrenic brain, specifically in the prefrontal and limbic brain regions.

The findings described above suggest that NAALADase inhibitors could be useful in treating glutamate abnormalities. However, the present invention is directed to the surprising and unexpected discovery that the novel compounds of the present invention are not only effective NAALADase inhibitors but are effective in treating prostate diseases, particularly prostate cancer. Although the cancer data relate to prostate cancer cells, NAALADase inhibitors are expected to be equally effective in treating cancer of other tissues where NAALADase enzyme reside, such as the brain, kidney and testis.

While a few NAALADase inhibitors have been identified, they have only been used in non-clinical research. Examples of such inhibitors include general metallopeptidase inhibitors such as o-phenanthroline, metal chelators such as EGTA and EDTA, and peptide analogs such as quisqualic acid and β-NAAG. Accordingly, a need exists for more NAALADase inhibitors to be identified and, particularly, for the treatment of prostate diseases such as prostate cancer.

SUMMARY OF THE INVENTION

The present invention is directed to novel methods for treating cancer, preventing tumor cell growth, inhibiting prostate tumor cell growth, and inhibiting NAALADase enzyme activity, in an animal, comprising administering an effective amount of a NAALADase inhibitor.

Preferred NAALADase inhibitors include compounds of formula I:

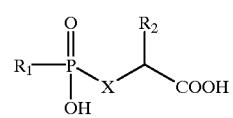

wherein $R_1$ is hydrogen, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$;

X is $CH_2$, O, or N; and $R_2$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$, wherein said alkyl, alkenyl, cycloalkyl, cycloalkenyl or aryl groups may be optionally substituted with carboxylic acid.

Preferably, the compound of formula I is present in an amount that is effective for inhibiting NAALADase enzyme activity, or treating a prostate disease in an animal.

The present invention further relates to a method of inhibiting NAALADase enzyme activity in an animal, comprising administering an effective amount of the compound of formula I to said animal.

BRIEF DESCRIPTION OF THE FIGURES

FIG. 1 shows the effect of 7-day treatment with quisqualate on the growth of LNCAP cells. Concentrations ranging from 10 nM to 1 μM of quisqualate show a sharp dose-dependent decrease of LNCAP cell proliferation as indicated by the significant decrease in the incorporation of [3H]thymidine.

FIG. 2 shows the effect of 7-day treatment with 2-(phosphonomethyl)pentanedioic acid on the growth of LNCAP cells. Concentrations ranging from 100 pM to 10 nM of 2-(phosphonomethyl)pentanedioic acid show a sharp dose-dependent decrease of LNCAP cell proliferation as indicated by the significant decrease in the incorporation of [3H]thymidine.

FIG. 4 shows the higher mean survival percentage of animals injected with 2-(phosphonomethyl)pentanedioic acid mixed with polymer as compared to those animals only receiving intratumoral injections of 2-(phosphonomethyl) pentanedioic acid or a vehicle control. The graph shows that 88% of the animals treated with polymer were alive after 72 days, and those animals had small tumors.

FIG. 5 shows that tumor growth slowed as a function of 2-(phosphonomethyl)pentanedioic acid dosage.

DETAILED DESCRIPTION OF THE INVENTION

Definitions

Figure 1:
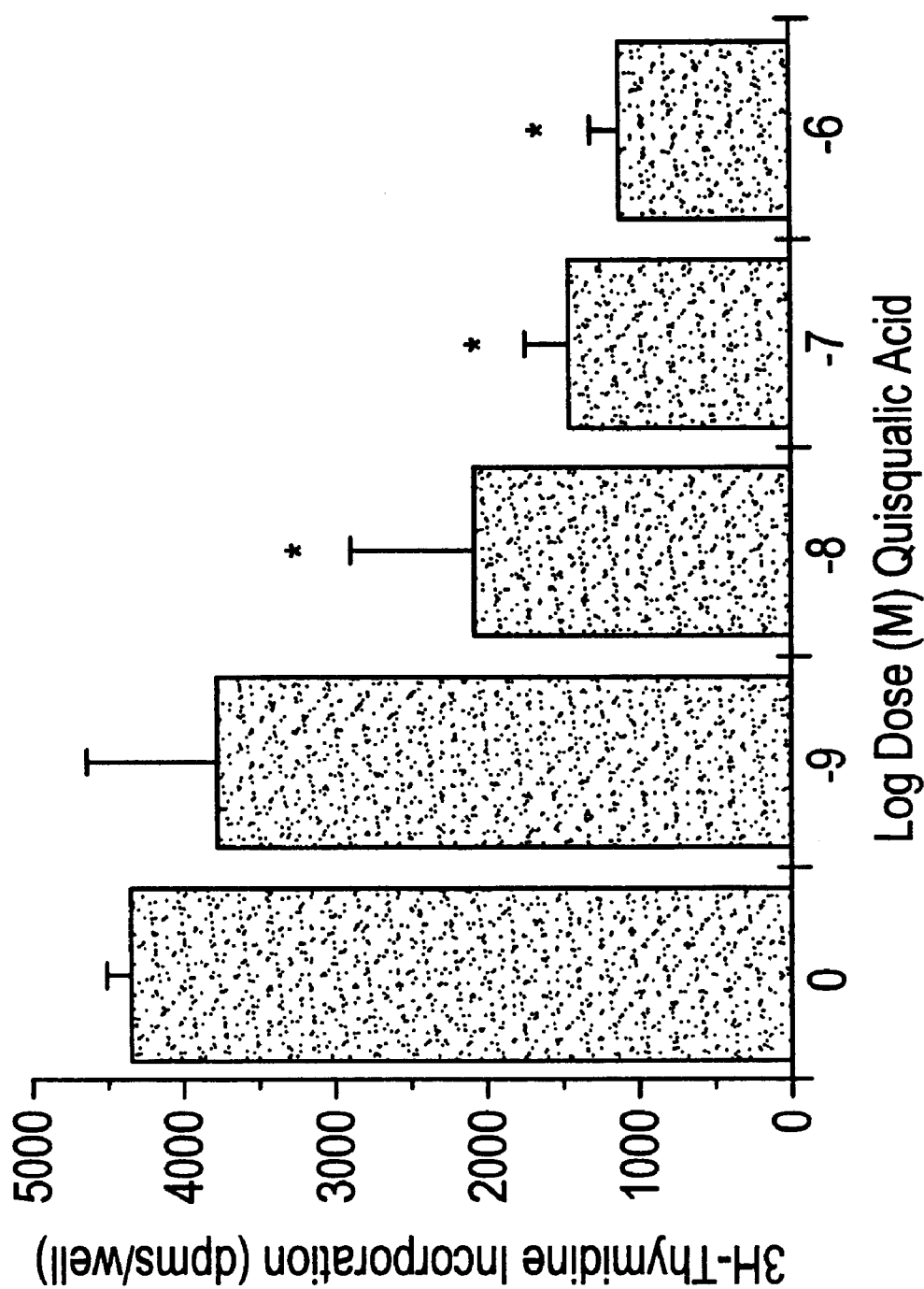
FIG. 1 is a bar graph plotting the growth of the prostate cancer cell line, LNCAP, against various concentrations of quisqualic acid, a NAALADase Inhibitor.

"Compound 3" refers to 2-(phosphonomethyl) pentanedioic acid, a NAALADase inhibitor.

"Inhibition", in the context of enzymes, refers to reversible enzyme inhibition such as competitive, uncompetitive and non-competitive inhibition. Competitive, uncompetitive and non-competitive inhibition can be distinguished by the effects of an inhibitor on the reaction kinetics of an enzyme. Competitive inhibition occurs when the inhibitor combines reversibly with the enzyme in such a way that it competes with a normal substrate for binding at the active site. The affinity between the inhibitor and the enzyme may be measured by the inhibitor constant, K$_i$, which is defined as:

$$K_i = \frac{[E][I]}{[EI]}$$

wherein [E] is the concentration of the enzyme, [I] is the concentration of the inhibitor, and [EI] is the concentration of the enzyme-inhibitor complex formed by the reaction of the enzyme with the inhibitor. Unless otherwise specified, K$_i$ as used herein refers to the affinity between the inventive compounds and NAALADase. "IC50" is a related term used to define the concentration or amount of a compound which is required to cause a 50% inhibition of the target enzyme.

The term "inhibition", in the context of tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention.

"NAAG" refers to N-acetyl-aspartyl-glutamate, an important peptide component of the brain, with levels comparable to the major inhibitor neurotransmitter gamma-aminobutyric acid (GABA). NAAG is neuron-specific, present in synaptic vesicles and released upon neuronal stimulation in several systems presumed to be glutamatergic. Studies suggest that NAAG may function as a neurotransmitter and/or neuromodulator in the central nervous system, or as a precursor of the neurotransmitter glutamate.

"NAALADase" refers to N-acetylated a-linked acidic dipeptidase, a membrane-bound metallopeptidase which catabolizes NAAG to N-acetylaspartate (NAA) and glutamate:

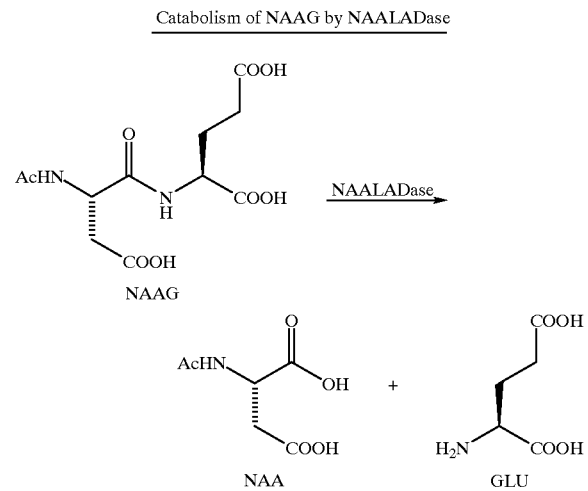

Catabolism of NAAG by NAALADase

NAALADase shows a high affinity for NAAG with a Km of 540 nM. If NAAG is a bioactive peptide, then NAALADase may serve to inactivate NAAG'S synaptic action. Alternatively, if NAAG functions as a precursor for glutamate, the primary function of NAALADase may be to regulate synaptic glutamate availability.

"Pharmaceutically acceptable salt" refers to a salt of the inventive compounds which possesses the desired pharmacological activity and which is neither biologically nor otherwise undesirable. The salt can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Examples of a base salt include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. The basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The term "prevention", in relation to tumor growth or tumor cell growth, means no tumor or tumor cell growth if none had occurred, no further tumor or tumor cell growth if there had already been growth.

The term "prostate disease" relates to prostate cancer such as adenocarcinoma or metastatic cancers, conditions characterized by abnormal growth of prostatic epithelial cells such as benign prostatic hyperplasia, and other conditions requiring treatment by the compounds of the present invention.

"PSA" refers to Prostate Specific Antigen, a well known prostate cancer marker. It is a protein produced by prostate cells and is frequently present at elevated levels in the blood of men with prostate cancer. PSA correlates with tumor burden, serves as an indicator of metastatic involvement, and provides a parameter for following a prostate cancer patient's response to surgery, irradiation and androgen replacement therapy.

"PSMA" refers to Prostate Specific Membrane Antigen, a potential prostate carcinoma marker that has been hypothesized to serve as a target for imaging and cytotoxic treatment modalities for prostate cancer. PSMA is expressed in prostatic ductal epithelium and is present in seminal plasma, prostatic fluid and urine. It has been found that the expression of PSMA cDNA confers the activity of NAALADase.

The term "treatment" refers to any process, action, application, therapy, or the like, wherein an animal, including a human being, is subject to medical aid with the object of improving the animal's condition, directly or indirectly.

Preferred NAALADase Inhibitors of the Present Invention

The present invention relates to a compound of formula I:

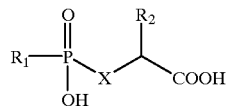

I or a pharmaceutically acceptable salt, hydrate, or a mixture thereof, wherein:

$R_1$ is hydrogen, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$;

X is $CH_2$, O, or $NR_1$, where $R_1$ is defined above; and $R_2$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$, wherein said alkyl, alkenyl, cycloalkyl, cycloalkenyl or aryl group may be optionally substituted with carboxylic acid.

The present invention also contemplates that said alkyl, alkenyl, cycloalkyl, cycloalkenyl or aryl groups may be optionally substituted with $C_3$–$C_8$ cycloalkyl, $C_3$ or $C_5$ cycloalkyl, $C_5$–$C_7$ cycloalkenyl, $C_1$–$C_4$ alkyl, $C_1$–$C_4$ alkenyl, halo, hydroxy, carboxy, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or $Ar_1$, and where $Ar_1$ is selected from the group consisting of 1-naphthyl, 2-naphthyl, 2-indolyl, 3-indolyl, 4-indolyl, 2-furyl, 3-furyl, tetrahydrofuranyl, 2-thienyl, 3-thienyl, 4-thienyl, 2-, 3-, or 4-pyridyl, or phenyl, having one to five substituents which are independently selected from the group consisting of hydrogen, halo, hydroxy, carboxy, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino; or pharmaceutically acceptable salts, hydrates, or mixtures thereof.

In a preferred embodiment, the compound is selected from the group of formula II:

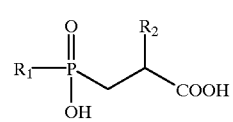

II wherein $R_1$ is hydrogen, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; and $R_2$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$, wherein said alkyl, alkenyl, cycloalkyl, cycloalkenyl or aryl group may be optionally substituted with carboxylic acid.

In another preferred embodiment, the R groups are either straight or branched aliphatic substituents or carbocyclic substituents illustrated by the compounds selected from the group of formula II:

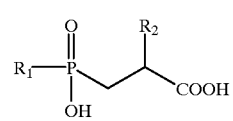

II wherein $R_1$ is hydrogen, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, 1-naphthyl, 2-naphthyl, or phenyl; and $R_2$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, 1-naphthyl, 2-naphthyl, or phenyl, wherein said alkyl, alkenyl, cycloalkyl, cycloalkenyl, 1-naphthyl, 2-naphthyl, or phenyl group may be optionally substituted with carboxylic acid.

Especially preferred methods utilize compounds wherein $R_1$ is either a straight or branched aliphatic group or a carbocyclic group, $R_2$ is ethyl which is substituted with a carboxylic acid, and X is $CH_2$ are selected from the group consisting of:

2-[[methylhydroxyphosphinyl]methyl]pentanedioic acid;
2-[[ethylhydroxyphosphinyl]methyl]pentanedioic acid;
2-[[propylhydroxyphosphinyl]methyl]pentanedioic acid;
2-[[butylhydroxyphosphinyl]methyl]pentanedioic acid;
2-[[cyclohexylhydroxyphosphinyl]methyl]pentanedioic acid;
2-[[(cyclohexyl)methylhydroxyphosphinyl]methyl] pentanedioic acid;
2-[[phenylhydroxyphosphinyl]methyl]pentanedioic acid;
2-[[benzylhydroxyphosphinyl]methyl]pentanedioic acid;
2-[[phenylethylhydroxyphosphinyl]methyl]pentanedioic acid;
2-[[phenylpropylhydroxyphosphinyl]methyl] pentanedioic acid;
2-[[phenylbutylhydroxyphosphinyl]methyl]pentanedioic acid;
2-[[(4-methylbenzyl)hydroxyphosphinyl]methyl] pentanedioic acid;
2-[[(4-fluorobenzyl)hydroxyphosphinyl]methyl] pentanedioic acid;
2-[[(2-fluorobenzyl)hydroxyphosphinyl]methyl] pentanedioic acid;
2-[[(pentafluorobenzyl)hydroxyphosphinyl]methyl] pentanedioic acid;
2-[[(methoxybenzyl)hydroxyphosphinyl]methyl] pentanedioic acid;
2-[[(4-fluorophenyl)hydroxyphosphinyl]methyl] pentanedioic acid;
2-[[((hydroxy)phenylmethyl)hydroxyphosphinyl]methyl] pentanedioic acid;
2-[[(3-methylbenzyl)hydroxyphosphinyl]methyl] pentanedioic acid;
2-(phosphonomethyl)pentanedioic acid;
2-[[(3-trifluoromethylbenzyl)hydroxyphosphinyl]methyl] pentanedioic acid;
2-[[(2,3,4-trimethoxyphenyl)hydroxyphosphinyl]methyl] pentanedioic acid;
2-[[(1-naphthyl)hydroxyphosphinyl]methyl]pentanedioic acid;
2-[[(2-naphthyl)hydroxyphosphinyl]methylpentanedioic acid;
2-[[(1-naphthyl)methylhydroxyphosphinyl]methyl] pentanedioic acid;
2-[[(2-naphthyl)methylhydroxyphosphinyl]methyl] pentanedioic acid;
2-[[(1-naphthyl)ethylhydroxyphosphinyl]methyl] pentanedioic acid;
2-[[(2-naphthyl)ethylhydroxyphosphinyl]methyl] pentanedioic acid;
2-[[(1-naphthyl)propylhydroxyphosphinyl]methyl] pentanedioic acid;
2-[[(2-naphthyl)propylhydroxyphosphinyl]methyl] pentanedioic acid;
2-[[(1-naphthyl)butylhydroxyphosphinyl]methyl] pentanedioic acid;
2-[[(2-naphthyl)butylhydroxyphosphinyl]methyl] pentanedioic acid; and
2-[[(phenylprop-2-enyl)hydroxyphosphinyl]methyl] pentanedioic acid.

Especially preferred methods utilize compounds wherein $R_1$ is either a straight or branched aliphatic group or a carbocyclic group, $R_2$ is ethyl which is substituted with a carboxylic acid, and X is $CH_2$ are selected from the group consisting of:

2-[(benzylhydroxyphosphinyl)methyl]pentanedioic acid;
2-[(phenylhydroxyphosphinyl)methyl]pentanedioic acid;
2-[[(hydroxy)phenylmethyl)hydroxyphosphinyl]methyl] pentanedioic acid;
2-(butylhydroxyphosphinyl)methyl]pentanedioic acid;
2-[[(3-methylbenzyl)hydroxyphosphinyl]methyl] pentanedioic acid;
2-[(3-phenylpropylhydroxyphosphinyl) methylpentanedioic acid;
2-[[(4-fluorophenyl)hydroxyphosphinyl]methyl] pentanedioic acid;
2-[(methylhydroxyphosphinyl)methyl]pentanedioic acid;
2-[(phenylethylhydroxyphosphinyl)methyl]pentanedioic acid;
2-[[(4-methylbenzyl)hydroxyphosphinyl]methyl] pentanedioic acid;
2-[[(4-fluorobenzyl)hydroxyphosphinyl]methyl] pentanedioic acid;
2-[[(4-methoxybenzyl)hydroxyphosphinyl]methyl] pentanedioic acid;
2-[[(2-fluorobenzyl)hydroxyphosphinyl]methyl] pentanedioic acid;
2-[[(pentafluorobenzyl)hydroxyphosphinyl]methyl] pentanedioic acid;
2-(phosphonomethyl)pentanedioic acid; and
2-[[(3-trifluoromethylbenzyl)hydroxyphosphinyl]methyl] pentanedioic acid.

Especially preferred methods utilize compounds wherein $R_1$ is a straight or branched aliphatic group or a carbocyclic group, $R_2$ is phenyl, and X is $CH_2$ are selected from the group consisting of:

3-(methylhydroxyphosphinyl)-2-phenylpropanoic acid;
3-(ethylhydroxyphosphinyl)-2-phenylpropanoic acid;
3-(propylhydroxyphosphinyl)-2-phenylpropanoic acid;
3-(butylhydroxyphosphinyl)-2-phenylpropanoic acid;
3-(cyclohexylhydroxyphosphinyl)-2-phenylpropanoic acid;
3-((cyclohexyl)methylhydroxyphosphinyl)-2-phenylpropanoic acid;
3-(phenylhydroxyphosphinyl)-2-phenylpropanoic acid;
3-(benzylhydroxyphosphinyl)-2-phenylpropanoic acid;
3-(phenylethylhydroxyphosphinyl)-2-phenylpropanoic acid;
3-(phenylpropylhydroxyphosphinyl)-2-phenylpropanoic acid;
3-(phenylbutylhydroxyphosphinyl)-2-phenylpropanoic acid;
3-[(2,3,4-trimethoxyphenyl)-3-hydroxyphosphinyl]-2-phenylpropanoic acid;
3-[(1-naphthyl)hydroxyphosphinyl]-2-phenylpropanoic acid;
3-[(2-naphthyl)hydroxyphosphinyl]-2-phenylpropanoic acid;
3-[(1-naphthyl)methylhydroxyphosphinyl]-2-phenylpropanoic acid;
3-[(2-naphthyl)methylhydroxyphosphinyl]-2-phenylpropanoic acid;

3-[(1-naphthyl)ethylhydroxyphosphinyl]-2-phenylpropanoic acid;

3-[(2-naphthyl)ethylhydroxyphosphinyl]-2-phenylpropanoic acid;

3-[(1-naphthyl)propylhydroxyphosphinyl]-2-phenylpropanoic acid;

3-[(2-naphthyl)propylhydroxyphosphinyl]-2-phenylpropanoic acid;

3-[(-naphthyl)butylhydroxyphosphinyl]-2-phenylpropanoic acid;

3-[(2-naphthyl)butylhydroxyphosphinyl]-2-phenylpropanoic acid; and

3-[phenylprop-2-enylhydroxyphosphinyl]-2-phenylpropanoic acid.

Although not limited to any one species, a highly preferred species where $R_1$ is a straight or branched aliphatic group or a carbocyclic group, $R_2$ is ethyl which is substituted with carboxylic acid, and X is $CH_2$ is 2-[[benzylhydroxyphosphinyl]methyl]pentanedioic acid.

Other preferred compounds of the present invention are selected from the group consisting of: hydroxyphosphinyl derivatives wherein X is $CH_2$, $R_1$ is a straight or branched aliphatic group or a carbocyclic group, and $R_2$ is an $C_2$–$C_8$ alkyl or alkenyl chain which is substituted with a carboxylic acid. Exemplary species include:

2-[(methylhydroxyphosphinyl)methyl]hexanedioic acid;

2-[(benzylhydroxyphosphinyl)methyl]hexanedioic acid;

2-[(methylhydroxyphosphinyl)methyl]heptanedioic acid;

2-[(benzylhydroxyphosphinyl)methyl]heptanedioic acid;

2-[(methylhydroxyphosphinyl)methyl]octanedioic acid;

2-[(benzylhydroxyphosphinyl)methyl]octanedioic acid;

2-[(methylhydroxyphosphinyl)methyl]nonanedioic acid;

2-[(benzylhydroxyphosphinyl)methyl]nonanedioic acid;

2-[(methylhydroxyphosphinyl)methyl]decanedioic acid; and

2-[(benzylhydroxyphosphinyl)methyl]decanedioic acid.

Other preferred compounds are selected from the group consisting of: and $R_2$ is a straight or branched aliphatic group or a carbocyclic group. Exemplary species include:

3-(benzylhydroxyphosphinyl)-2-methylpropanoic acid;

3-(benzylhydroxyphosphinyl)-2-ethylpropanoic acid;

3-(benzylhydroxyphosphinyl)-2-propylpronanoic acid;

3-(benzylhydroxyphosphinyl)-2-butylpropanoic acid;

3-(benzylhydroxyphosphinyl)-2-cyclohexylpropanoic acid;

3-(benzylhydroxyphosphinyl)-2-(cyclohexyl)methylpropanoic acid;

3-(benzylhydroxyphosphinyl)-2-phenylpropanoic acid;

3-(benzylhydroxyphosphinyl)-2-benzylpropanoic acid;

3-(benzylhydroxyphosphinyl)-2-phenylethylpropanoic acid;

3-(benzylhydroxyphosphinyl)-2-phenylpropylpropanoic acid;

3-(benzylhydroxyphosphinyl)-2-phenylbutylpropanoic acid;

3-(benzylhydroxyphosphinyl)-2-(2,3,4-trimethoxyphenyl)propanoic acid;

3-(benzylhydroxyphosphinyl)-2-(1-naphthyl)propanoic acid;

3-(benzylhydroxyphosphinyl)-2-(2-naphthyl)propanoic acid;

3-(benzylhydroxyphosphinyl)-2-(1-naphthyl)methylpropanoic acid;

3-(benzylhydroxyphosphinyl)-2-(2-naphthyl)methylpropanoic acid;

3-(benzylhydroxyphosphinyl)-2-(1-naphthyl)ethylpropanoic acid;

3-(benzylhydroxyphosphinyl)-2-(2-naphthyl)ethylpropanoic acid;

3-(benzylhydroxyphosphinyl)-2-(1-naphthyl)propylpropanoic acid;

3-(benzylhydroxyphosphinyl)-2-(2-naphthyl)propylpropanoic acid;

3-(benzylhydroxyphosphinyl)-2-(1-naphthyl)butylpropanoic acid;

3-(benzylhydroxyphosphinyl)-2-(2-naphthyl)butylpropanoic acid; and 3-(benzylhydroxyphosphinyl)-2-phenylprop-2-enylpropanoic acid.

Especially preferred methods use compounds wherein $R_1$ is said alkyl, alkenyl, cycloalkyl, or aryl group which is substituted with a heterocyclic group, $R_2$ is ethyl which is substituted with a carboxylic acid, and X is $CH_2$ are selected from the group consisting of:

2-[[(2-pyridyl)methylhydroxyphosphinyl]methyl]pentanedioic acid;

2-[[(3-pyridyl)methylhydroxyphosphinyl]methyl]pentanedioic acid;

2-[[(4-pyridyl)methylhydroxyphosphinyl]methyl]pentanedioic acid;

2-[[(3-pyridyl)ethylhydroxyphosphinyl]methyl]pentanedioic acid;

2-[[(3-pyridyl)propylhydroxyphosphinyl]methyl]pentanedioic acid;

2-[[(tetrahydrofuranyl)methylhydroxyphosphinyl]methyl]pentanedioic acid;

2-[[(tetrahydrofuranyl)ethylhydroxyphosphinyl]methyl]pentanedioic acid;

2-[[(tetrahydrofuranyl)propylhydroxyphosphinyl]methyl]pentanedioic acid;

2-[[(2-indolyl)methylhydroxyphosphinyl]methyl]pentanedioic acid;

2-[[(3-indolyl)methylhydroxyphosphinyl]methyl]pentanedioic acid;

2-[[(4-indolyl)methylhydroxyphosphinyl]methyl]pentanedioic acid;

2-[[(3-indolyl)ethylhydroxyphosphinyl]methyl]pentanedioic acid;

2-[[(3-indolyl)propylhydroxyphosphinyl]methyl]pentanedioic acid;

2-[[(2-thienyl)methylhydroxyphosphinyl]methyl]pentanedioic acid;

2-[[(3-thienyl)methylhydroxyphosphinyl]methyl]pentanedioic acid;

2-[[(4-thienyl)methylhydroxyphosphinyl]methyl]pentanedioic acid;

2-[[(3-thienyl)ethylhydroxyphosphinyl]methyl]pentanedioic acid; and

2-[[(3-thienyl)propylhydroxyphosphinyl]methyl]pentanedioic acid.

Especially preferred methods use compounds wherein $R_1$ is said alkyl, alkenyl, cycloalkyl, or aryl group which is substituted with a heterocyclic group, $R_2$ is phenyl, and X is $CH_2$ are selected from the group consisting of:

3-[(2-pyridyl)methylhydroxyphosphinyl]-2-phenylpropanoic acid;
3-[(3-pyridyl)methylhydroxyphosphinyl]-2-phenylpropanoic acid;
3-[(4-pyridyl)methylhydroxyphosphinyl]-2-phenylpropanoic acid;
3-[(3-pyridyl)ethylhydroxyphosphinyl]-2-phenylpropanoic acid;
3-[(3-pyridyl)propylhydroxyphosphinyl]-2-phenylpropanoic acid;
3-[(tetrahydrofuranyl)methylhydroxyphosphinyl]-2-phenylpropanoic acid;
3-[(tetrahydrofuranyl)ethylhydroxyphosphinyl]-2-phenylpropanoic acid;
3-[(tetrahydrofuranyl)propylhydroxyphosphinyl]-2-phenylpropanoic acid;
3-[(2-indolyl)methylhydroxyphosphinyl]-2-phenylpropanoic acid;
3-[(3-indolyl)methylhydroxyphosphinyl]-2-phenylpropanoic acid;
3-[(4-indolyl)methylhydroxyphosphinyl]-2-phenylpropanoic acid;
3-[(3-indolyl)ethylhydroxyphosphinyl]-2-phenylpropanoic acid;
3-[(3-indolyl)propylhydroxyphosphinyl]-2-phenylpropanoic acid;
3-[(2-thienyl)methylhydroxyphosphinyl]-2-phenylpropanoic acid;
3-[(3-thienyl)methylhydroxyphosphinyl]-2-phenylpropanoic acid;
3-[(4-thienyl)methylhydroxyphosphinyl]-2-phenylpropanoic acid;
3-[(3-thienyl)ethylhydroxyphosphinyl]-2-phenylpropanoic acid; and
3-[(3-thienyl)propylhydroxyphosphinyl]-2-phenylpropanoic acid.

Especially preferred methods use compounds wherein $R_1$ is benzyl, $R_2$ is said alkyl, alkenyl, cycloalkyl, or aryl group which is substituted with a heterocyclic group, and X is $CH_2$ are selected from the group consisting of:

3-(benzylhydroxyphosphinyl)-2-(2-pyridyl)methylpropanoic acid;
3-(benzylhydroxyphosphinyl)-2-(3-pyridyl)methylpropanoic acid;
3-(benzylhydroxyphosphinyl)-2-(4-pyridyl)methylpropanoic acid;
3-(benzylhydroxyphosphinyl)-2-(3-pyridyl)ethypropanoic acid;
3-(benzylhydroxyphosphinyl)-2-(3-pyridyl)propylpropanoic acid;
3-(benzylhydroxyphosphinyl)-2-(tetrahydrofuranyl)methylpropanoic acid;
3-(benzylhydroxyphosphinyl)-2-(tetrahydrofuranyl)ethylpropanoic acid;
3-(benzylhydroxyphosphinyl)-2-(tetrahydrofuranyl)propylpropanoic acid;
3-(benzylhydroxyphosphinyl)-2-(2-indolyl)methylpropanoic acid;
3-(benzylhydroxyphosphinyl)-2-(3-indolyl)methylpropanoic acid;
3-(benzylhydroxyphosphinyl)-2-(4-indolyl)methylpropanoic acid;
3-(benzylhydroxyphosphinyl)-2-(3-indolyl)ethylpropanoic acid;
3-(benzylhydroxyphosphinyl)-2-(3-indolyl)propylpropanoic acid;
3-(benzylhydroxyphosphinyl)-2-(2-thienyl)methylpropanoic acid;
3-(benzylhydroxyphosphinyl)-2-(3-thienyl)methylpropanoic acid;
3-(benzylhydroxyphosphinyl)-2-(4-thienyl)methylpropanoic acid;
3-(benzylhydroxyphosphinyl)-2-(3-thienyl)ethylpropanoic acid; and
3-(benzylhydroxyphosphinyl)-2-(3-thienyl)propylpropanoic acid.

In another preferred embodiment, the R groups are heterocyclic substituents illustrated by the compounds selected from the group having formula II:

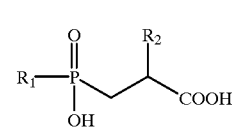

II wherein
$R_1$ is $Ar_1$; and
$R_2$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$, wherein said alkyl, alkenyl, cycloalkyl, cycloalkenyl or aryl group may be optionally substituted with carboxylic acid.

Especially preferred methods use compounds wherein $R_1$ is a heterocyclic group, $R_2$ is ethyl which is substituted with carboxylic acid, and X is $CH_2$ are selected from the group consisting of:

2-[[(2-pyridyl)hydroxyphosphinyl]methyl]pentanedioic acid;
2-[[(3-pyridyl)hydroxyphosphinyl]methyl]pentanedioic acid;
2-[[(4-pyridyl)hydroxyphosphinyl]methyl]pentanedioic acid;
2-[[(tetrahydrofuranyl)hydroxyphosphinyl]methyl]pentanedioic acid;
2-[[(2-indolyl)hydroxyphosphinyl]methyl]pentanedioic acid;
2-[[(3-indolyl)hydroxyphosphinyl]methyl]pentanedioic acid;
2-[[(4-indolyl)hydroxyphosphinyl]methyl]pentanedioic acid;
2-[[(2-thienyl)hydroxyphosphinyl]methyl]pentanedioic acid;
2-[[(3-thienyl)hydroxyphosphinyl]methyl]pentanedioic acid; and
2-[[(4-thienyl)hydroxyphosphinyl]methyl]pentanedioic acid.

Compounds of the present invention wherein $R_1$ is a heterocyclic group, $R_2$ is phenyl, and X is $CH_2$ are selected from the group consisting of:

3-[(2-pyridyl)hydroxyphosphinyl]-2-phenylpropanoic acid;
3-[(3-pyridyl)hydroxyphosphinyl]-2-phenylpropanoic acid;
3-[(4-pyridyl)hydroxyphosphinyl]-2-phenylpropanoic acid;

3-[(tetrahydrofuranyl)hydroxyphosphinyl]-2-phenylpropanoic acid;

3-[(2-indolyl)hydroxyphosphinyl]-2-phenylpropanoic acid;

3-[(3-indolyl)hydroxyphosphinyl]-2-phenylpropanoic acid;

3-[(4-indolyl)hydroxyphosphinyl]-2-phenylpropanoic acid;

3-[(2-thienyl)hydroxyphosphinyl]-2-phenylpropanoic acid;

3-[(3-thienyl)hydroxyphosphinyl]-2-phenylpropanoic acid; and

3-[(4-thienyl)hydroxyphosphinyl]-2-phenylpropanoic acid.

Compounds are also preferably selected from the group of formula II:

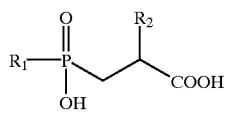

II wherein $R_1$ is hydrogen, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; and $R_2$ is $Ar_1$, wherein said aryl group may be optionally substituted with carboxylic acid.

Particular species wherein $R_2$ is heterocyclic may be easily made and used by persons of ordinary skill in the art in accordance with the teachings provided herein and known in the art.

Compounds wherein $R_1$ is benzyl, $R_2$ is heterocyclic, and X is $CH_2$ are selected from the group consisting of:

3-(benzylhydroxyphosphinyl)-2-(2-pyridyl)propanoic acid;

3-(benzylhydroxyphosphinyl)-2-(3-pyridyl)propanoic acid;

3-(benzylhydroxyphosphinyl)-2-(4-pyridyl)propanoic acid;

3-(benzylhydroxyphosphinyl)-2-(tetrahydrofuranyl) propanoic acid;

3-(benzylhydroxyphosphinyl)-2-(2-indolyl)propanoic acid;

3-(benzylhydroxyphosphinyl)-2-(3-indolyl)propanoic acid;

3-(benzylhydroxyphosphinyl)-2-(4-indolyl)propanoic acid;

3-(benzylhydroxyphosphinyl)-2-(2-thienyl)propanoic acid;

3-(benzylhydroxyphosphinyl)-2-(3-thienyl)propanoic acid; and 3-(benzylhydroxyphosphinyl)-2-(4-thienyl)propanoic acid.

Preferred compounds are also selected from formula III:

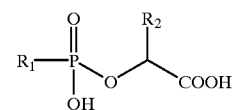

III wherein $R_1$ is hydrogen, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; and $R_2$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$, wherein said alkyl, alkenyl, cycloalkyl, cycloalkenyl or aryl group may be optionally substituted with carboxylic acid.

In another preferred embodiment, the R groups are straight or branched or carbocyclic substituents illustrated by the compounds selected from the group of formula III:

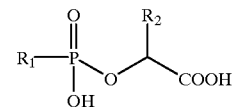

III wherein $R_1$ is hydrogen, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, 1-naphthyl, 2-naphthyl, or phenyl; and $R_2$ is $C_2$–$C_9$ straight or branched chain alkyl, $C_2$–$C_9$ straight or branched chain alkenyl group, $C_3$–$C_8$ cycloalkyl, $C_5$–$C_7$ cycloalkenyl, 1-naphthyl, 2-naphthyl, or phenyl, wherein said alkyl, alkenyl, cycloalkyl, cycloalkenyl, 1-naphthyl, 2-naphthyl, or phenyl group may be optionally substituted with carboxylic acid.

Especially preferred compounds of Formula III of the present invention wherein $R_1$ is a straight or branched aliphatic group or a carbocyclic group and $R_2$ is ethyl which is substituted with a carboxylic acid are selected from the group consisting of:

2-[[methylhydroxyphosphinyl]oxy]pentanedioic acid;

2-[[ethylhydroxyphosphinyl]oxy]pentanedioic acid;

2-[[propylhydroxyphosphinyl]oxy]pentanedioic acid;

2-[[butylhydroxyphosphinyl]oxy]pentanedioic acid;

2-[[cyclohexylhydroxyphosphinyl]oxy]pentanedioic acid;

2-[[(cyclohexyl)methylhydroxyphosphinyl]oxy] pentanedioic acid;

2-[[phenylhydroxyphosphinyl]oxy]pentanedioic acid;

2-[[benzylhydroxyphosphinyl]oxy]pentanedioic acid;

2-[[phenylethylhydroxyphosphinyl]oxy]pentanedioic acid;

2-[[phenylpropylhydroxyphosphinyl]oxy]pentanedioic acid;

2-[[phenylbutylhydroxyphosphinyl]oxy]pentanedioic acid;

2-[[(4-methylbenzyl)hydroxyphosphinyl]oxy] pentanedioic acid;

2-[[(4-fluorobenzyl)hydroxyphosphinyl]oxy] pentanedioic acid;

2-[[(2-fluorobenzyl)hydroxyphosphinyl]oxy] pentanedioic acid;
2-[[(pentafluorobenzyl)hydroxyphosphinyl]oxy] pentanedioic acid;
2-[[(methoxybenzyl)hydroxyphosphinyl]oxy] pentanedioic acid;
2-[[(4-fluorophenyl)hydroxyphosphinyl]oxy] pentanedioic acid;
2-[[((hydroxy)phenylmethyl)hydroxyphosphinyl]oxy] pentanedioic acid;
2-[[(3-methylbenzyl)hydroxyphosphinyl]oxy] pentanedioic acid;
2-(phosphono)oxy]pentanedioic acid;
2-[[(3-trifluoromethylbenzyl)hydroxyphosphinyl]oxy] pentanedioic acid;
2-[[(2,3,4-trimethoxyphenyl)hydroxyphosphinyl]oxy] pentanedioic acid;
2-[[(1-naphthyl)hydroxyphosphinyl]oxy]pentanedioic acid;
2-[[(2-naphthyl)hydroxyphosphinyl]oxy]pentanedioic acid;
2-[[(1-naphthyl)methylhydroxyphosphinyl]oxy] pentanedioic acid;
2-[[(2-naphthyl)methylhydroxyphosphinyl]oxy] pentanedioic acid;
2-[[(1-naphthyl)ethylhydroxyphosphinyl]oxy] pentanedioic acid;
2-[[(2-naphthyl)ethylhydroxyphosphinyl]oxy] pentanedioic acid;
2-[[(1-naphthyl)propylhydroxyphosphinyl]oxy] pentanedioic acid;
2-[[(2-naphthyl)propylhydroxyphosphinyl]oxy] pentanedioic acid;
2-[[(1-naphthyl)butylhydroxyphosphinyl]oxy] pentanedioic acid;
2-[[(2-naphthyl)butylhydroxyphosphinyl]oxy] pentanedioic acid; and
2-[[(phenylprop-2-enyl)hydroxyphosphinyl]oxy] pentanedioic acid.

Especially preferred compounds of Formula III of the present invention wherein $R_1$ is a straight or branched aliphatic group or a carbocyclic group and $R_2$ is ethyl which is substituted with a carboxylic acid are selected from the group consisting of:
2-[(benzylhydroxyphosphinyl)oxy]pentanedioic acid;
2-[(phenylhydroxyphosphinyl)oxy]pentanedioic acid;
2-[[((hydroxy)phenylmethyl)hydroxyphosphinyl]oxy] pentanedioic acid;
2-[(butylhydroxyphosphinyl)oxy]pentanedioic acid;
2-[[(3-methylbenzyl)hydroxyphosphinyl]oxy] pentanedioic acid;
2-[(3-phenylpropylhydroxyphosphinyl)oxy]pentanedioic acid;
2-[[(4-fluorophenyl)hydroxyphosphinyl]oxy] pentanedioic acid;
2-[(methylhydroxyphosphinyl)oxy]pentanedioic acid;
2-[(phenylethylhydroxyphosphinyl)oxy]pentanedioic acid;
2-[[(4-methylbenzyl)hydroxyphosphinyl]oxy] pentanedioic acid;
2-[[(4-fluorobenzyl)hydroxyphosphinyl]oxy] pentanedioic acid;
2-[[(4-methoxybenzyl)hydroxyphosphinyl]oxy] pentanedioic acid;
2-[[(2-fluorobenzyl)hydroxyphosphinyl]oxy] pentanedioic acid;
2-[[(pentafluorobenzyl)hydroxyphosphinyl]oxy] pentanedioic acid;
2-[(phosphono)oxy]pentanedioic acid; and
2-[[(3-trifluoromethylbenzyl)hydroxyphosphinyl]oxy] pentanedioic acid.

Compounds of the present invention wherein $R_1$ is a straight or branched aliphatic group or a carbocyclic group, $R_2$ is phenyl, and X is oxygen are selected from the group consisting of:
2-[[methylhydroxyphosphinyl]oxy]-2-phenylethanoic acid;
2-[[ethylhydroxyphosphinyl]oxy]-2-phenylethanoic acid;
2-[[propylhydroxyphosphinyl]oxy]-2-phenylethanoic acid;
2-[[butylhydroxyphosphinyl]oxy]-2-phenylethanoic acid;
2-[[cyclohexylhydroxyphosphinyl]oxy]-2-phenylethanoic acid;
2-[[(cyclohexyl)methylhydroxyphosphinyl]oxy]-2-phenylethanoic acid;
2-[[phenylhydroxyphosphinyl]oxy]-2-phenylethanoic acid;
2-[[benzylhydroxyphosphinyl]oxy]-2-phenylethanoic acid;
2-[[phenylethylhydroxyphosphinyl]oxy]-2-phenylethanoic acid;
2-[[phenylpropylhydroxyphosphinyl]oxy]-2-phenylethanoic acid;
2-[[phenylbutylhydroxyphosphinyl]oxy]-2-phenylethanoic acid;
2-[[(2,3,4-trimethoxyphenyl)-3-hydroxyphosphinyl]oxy]-2-phenylethanoic acid;
2-[[(1-naphthyl)hydroxyphosphinyl]oxy]-2-phenylethanoic acid;
2-[[(2-naphthyl)hydroxyphosphinyl]oxy]-2-phenylethanoic acid;
2-[[(1-naphthyl)methylhydroxyphosphinyl]oxy]-2-phenylethanoic acid;
2-[[(2-naphthyl)methylhydroxyphosphinyl]oxy]-2-phenylethanoic acid;
2-[[(1-naphthyl)ethylhydroxyphosphinyl]oxy]-2-phenylethanoic acid;
2-[[(2-naphthyl)ethylhydroxyphosphinyl]oxy]-2-phenylethanoic acid;
2-[[(1-naphthyl)propylhydroxyphosphinyl]oxy]-2-phenylethanoic acid;
2-[[(2-naphthyl)propylhydroxyphosphinyl]oxy]-2-phenylethanoic acid;
2-[[(1-naphthyl)butylhydroxyphosphinyl]oxy]-2-phenylethanoic acid;
2-[[(2-naphthyl)butylhydroxyphosphinyl]oxy]-2-phenylethanoic acid; and
2-[[phenylprop-2-enylhydroxyphosphinyl]oxy]-2-phenylethanoic acid.

Although not limited to any one particular species, a highly preferred species where $R_1$ is a straight or branched aliphatic group or a carbocyclic group, $R_2$ is ethyl which is substituted with carboxylic acid, and X is oxygen is 2-[[benzylhydroxyphosphinyl]oxy]pentanedioic acid.

Other especially preferred compounds of the present invention are selected from the group consisting of: phosphonate derivatives wherein X is oxygen, $R_1$ is a straight or branched aliphatic group or a carbocyclic group, and $R_2$ is an $C_2$–$C_8$ alkyl or alkenyl chain which is substituted with a carboxylic acid. Exemplary species include:

2-[(methylhydroxyphosphinyl)oxy]hexanedioic acid;
2-[(benzylhydroxyphosphinyl)oxy]hexanedioic acid;
2-[(methylhydroxyphosphinyl)oxy]heptanedioic acid;
2-[(benzylhydroxyphosphinyl)oxy]heptanedioic acid;
2-[(methylhydroxyphosphinyl)oxy]octanedioic acid;
2-[(benzylhydroxyphosphinyl)oxy]octanedioic acid;
2-[(methylhydroxyphosphinyl)oxy]nonanedioic acid;
2-[(benzylhydroxyphosphinyl)oxy]nonanedioic acid;
2-[(methylhydroxyphosphinyl)oxy]decanedioic acid; and
2-[(benzylhydroxyphosphinyl)oxy]decanedioic acid.

Other especially preferred compounds are selected from the group consisting of: phosphonate derivatives wherein X is oxygen, $R_1$ is benzyl, and $R_2$ is a straight or branched aliphatic group or a carbocyclic group. Exemplary species include:

2-[[benzylhydroxyphosphinyl]oxy]-2-methylethanoic acid;
2-[[benzylhydroxyphosphinyl]oxy]-2-ethylethanoic acid;
2-[[benzylhydroxyphosphinyl]oxy]-2-propylethanoic acid;
2-[[benzylhydroxyphosphinyl]oxy]-2-butylethanoic acid;
2-[[benzylhydroxyphosphinyl]oxy]-2-cyclohexylethanoic acid;
2-[[benzylhydroxyphosphinyl]oxy]-2-(cyclohexyl)methylethanoic acid;
2-[[benzylhydroxyphosphinyl]oxy]-2-phenylethanoic acid;
2-[[benzylhydroxyphosphinyl]oxy]-2-benzylethanoic acid;
2-[[benzylhydroxyphosphinyl]oxy]-2-phenylethylethanoic acid;
2-[[benzylhydroxyphosphinyl]oxy]-2-phenylpropylethanoic acid;
2-[[benzylhydroxyphosphinyl]oxy]-2-phenylbutylethanoic acid;
2-[[benzylhydroxyphosphinyl]oxy]-2-(2,3,4-trimethoxyphenyl)ethanoic acid;
2-[[benzylhydroxyphosphinyl]oxy]-2-(1-naphthyl)ethanoic acid;
2-[[benzylhydroxyphosphinyl]oxy]-2-(2-naphthyl)ethanoic acid;
2-[[benzylhydroxyphosphinyl]oxy]-2-(1-naphthyl)methylethanoic acid;
2-[[benzylhydroxyphosphinyl]oxy]-2-(2-naphthyl)methylethanoic acid;
2-[[benzylhydroxyphosphinyl]oxy]1-2-(1-naphthyl)ethylethanoic acid;
2-[[benzylhydroxyphosphinyl]oxy]-2-(2-naphthyl)ethylethanoic acid;
2-[[benzylhydroxyphosphinyl]oxy]-2-(1-naphthyl)propylethanoic acid;
2-[[benzylhydroxyphosphinyl]oxy]-2-(2-naphthyl)propylethanoic acid;
2-[[benzylhydroxyphosphinyl]oxy]-2-(1-naphthyl)butylethanoic acid;
2-[[benzylhydroxyphosphinyl]oxy]-2-(2-naphthyl)butylethanoic acid; and
2-[[benzylhydroxyphosphinyl]oxy]-2-phenylprop-2-enylethanoic acid.

Especially preferred methods utilize compounds wherein $R_1$ is said alkyl, alkenyl, cycloalkyl, or aryl group which is substituted with a heterocyclic group, $R_2$ is ethyl which is substituted with a carboxylic acid, and X is oxygen are selected from the group consisting of:

2-[[(2-pyridyl)methylhydroxyphosphinyl]oxy]pentanedioic acid;
2-[[(3-pyridyl)methylhydroxyphosphinyl]oxy]pentanedioic acid;
2-[[(4-pyridyl)methylhydroxyphosphinyl]oxy]pentanedioic acid;
2-[[(3-pyridyl)ethylhydroxyphosphinyl]oxy]pentanedioic acid;
2-[[(3-pyridyl)propylhydroxyphosphinyl]oxy]pentanedioic acid;
2-[[(tetrahydrofuranyl)methylhydroxyphosphinyl]oxy]pentanedioic acid;
2-[[(tetrahydrofuranyl)ethylhydroxyphosphinyl]oxy]pentanedioic acid;
2-[[(tetrahydrofuranyl)propylhydroxyphosphinyl]oxy]pentanedioic acid;
2-[[(2-indolyl)methylhydroxyphosphinyl]oxy]pentanedioic acid;
2-[[(3-indolyl)methylhydroxyphosphinyl]oxy]pentanedioic acid;
2-[[(4-indolyl)methylhydroxyphosphinyl]oxy]pentanedioic acid;
2-[[(3-indolyl)ethylhydroxyphosphinyl]oxy]pentanedioic acid;
2-[[(3-indolyl)propylhydroxyphosphinyl]oxy]pentanedioic acid;
2-[[(2-thienyl)methylhydroxyphosphinyl]oxy]pentanedioic acid;
2-[[(3-thienyl)methylhydroxyphosphinyl]oxy]pentanedioic acid;
2-[[(4-thienyl)methylhydroxyphosphinyl]oxy]pentanedioic acid;
2-[[(3-thienyl)ethylhydroxyphosphinyl]oxy]pentanedioic acid; and
2-[[(3-thienyl)propylhydroxyphosphinyl]oxy]pentanedioic acid.

Especially preferred methods utilize compounds wherein $R_1$ is said alkyl, alkenyl, cycloalkyl, or aryl group which is substituted with a heterocyclic group, $R_2$ is phenyl, and X is oxygen are selected from the group consisting of:

2-[[(2-pyridyl)methylhydroxyphosphinyl]oxy]-2-phenylethanoic acid;
2-[[(3-pyridyl)methylhydroxyphosphinyl]oxy]-2-phenylethanoic acid;
2-[[(4-pyridyl)methylhydroxyphosphinyl]oxy]-2-phenylethanoic acid;
2-[[(3-pyridyl)ethylhydroxyphosphinyl]oxy]-2-phenylethanoic acid;
2-[[(3-pyridyl)propylhydroxyphosphinyl]oxy]-2-phenylethanoic acid;
2-[[(tetrahydrofuranyl)methylhydroxyphosphinyl]oxy]-2-phenylethanoic acid;
2-[[(tetrahydrofuranyl)ethylhydroxyphosphinyl]oxy]-2-phenylethanoic acid;

2-[[(tetrahydrofuranyl)propylhydroxyphosphinyl]oxy]-2-phenylethanoic acid;

2-[[(2-indolyl)methylhydroxyphosphinyl]oxy]-2-phenylethanoic acid;

2-[[(3-indolyl)methylhydroxyphosphinyl]oxy]-2-phenylethanoic acid;

2-[[(4-indolyl)methylhydroxyphosphinyl]oxy]-2-phenylethanoic acid;

2-[[(3-indolyl)ethylhydroxyphosphinyl]oxy]-2-phenylethanoic acid;

2-[[(3-indolyl)propylhydroxyphosphinyl]oxy]-2-phenylethanoic acid;

2-[[(2-thienyl)methylhydroxyphosphinyl]oxy]-2-phenylethanoic acid;

2-[[(3-thienyl)methylhydroxyphosphinyl]oxy]-2-phenylethanoic acid;

2-[[(4-thienyl)methylhydroxyphosphinyl]oxy]-2-phenylethanoic acid;

2-[[(3-thienyl)ethylhydroxyphosphinyl]oxy]-2-phenylethanoic acid; and

2-[[(3-thienyl)propylhydroxyphosphinyl]oxy]-2-phenylethanoic acid.

Especially preferred methods utilize compounds wherein $R_1$ is benzyl, $R_2$ is said alkyl, alkenyl, cycloalkyl, or aryl group which is substituted with a heterocyclic group, and X is oxygen are selected from the group consisting of:

2-[[benzylhydroxyphosphinyl]oxy]-2-(2-pyridyl)methylethanoic acid;

2-[[benzylhydroxyphosphinyl]oxy]-2-(3-pyridyl)methylethanoic acid;

2-[[benzylhydroxyphosphinyl]oxy]-2-(4-pyridyl)methylethanoic acid;

2-[[benzylhydroxyphosphinyl]oxy]-2-(3-pyridyl)ethylethanoic acid;

2-[[benzylhydroxyphosphinyl]oxy]-2-(3-pyridyl)propylethanoic acid;

2-[[benzylhydroxyphosphinyl]oxy]-2-(tetrahydrofuranyl)methylethanoic acid;

2-[[benzylhydroxyphosphinyl]oxy]-2-(tetrahydrofuranyl)ethylethanoic acid;

2-[[benzylhydroxyphosphinyl]oxy]-2-(tetrahydrofuranyl)propylethanoic acid;

2-[[benzylhydroxyphosphinyl]oxy]-2-(2-indolyl)methylethanoic acid;

2-[[benzylhydroxyphosphinyl]oxy]-2-(3-indolyl)methylethanoic acid;

2-[[benzylhydroxyphosphinyl]oxy]-2-(4-indolyl)methylethanoic acid;

2-[[benzylhydroxyphosphinyl]oxy]-2-(3-indolyl)ethylethanoic acid;

2-[[benzylhydroxyphosphinyl]oxy]-2-(3-indolyl)propylethanoic acid;

2-[[benzylhydroxyphosphinyl]oxy]-2-(2-thienyl)methylethanoic acid;

2-[[benzylhydroxyphosphinyl]oxy]-2-(3-thienyl)methylethanoic acid;

2-[[benzylhydroxyphosphinyl]oxy]-2-(4-thienyl)methylethanoic acid;

2-[[benzylhydroxyphosphinyl]oxy]-2-(3-thienyl)ethylethanoic acid; and

2-[[benzylhydroxyphosphinyl]oxy]-2-(3-thienyl)propylethanoic acid.

In another preferred embodiment, $R_1$ is a heterocyclic substituent illustrated by the compounds selected from the group of formula III:

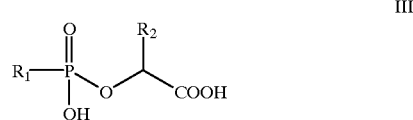

wherein $R_1$ is $Ar_1$; and $R_2$ is $C_2$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$, wherein said alkyl, alkenyl, cycloalkyl, cycloalkenyl or aryl group may be optionally substituted with carboxylic acid.

Especially preferred compounds wherein $R_1$ is a heterocyclic group, $R_2$ is ethyl which is substituted with carboxylic acid, and X is oxygen are selected from the group consisting of:

2-[[(2-pyridyl)hydroxyphosphinyl]oxy]pentanedioic acid;

2-[[(3-pyridyl)hydroxyphosphinyl]oxy]pentanedioic acid;

2-[[(4-pyridyl)hydroxyphosphinyl]oxy]pentanedioic acid;

2-[[(tetrahydrofuranyl)hydroxyphosphinyl]oxy]pentanedioic acid;

2-[[(2-indolyl)hydroxyphosphinyl]oxy]pentanedioic acid;

2-[[(3-indolyl)hydroxyphosphinyl]oxy]pentanedioic acid;

2-[[(4-indolyl)hydroxyphosphinyl]oxy]pentanedioic acid;

2-[[(2-thienyl)hydroxyphosphinyl]oxy]pentanedioic acid;

2-[[(3-thienyl)hydroxyphosphinyl]oxy]pentanedioic acid; and

2-[[(4-thienyl)hydroxyphosphinyl]oxy]pentanedioic acid.

Compounds of the present invention wherein $R_1$ is a heterocyclic group, $R_2$ is phenyl, and X is oxygen are selected from the group consisting of:

2-[[(2-pyridyl)hydroxyphosphinyl]oxy]-2-phenylethanoic acid;

2-[[(3-pyridyl)hydroxyphosphinyl]oxy]-2-phenylethanoic acid;

2-[[(4-pyridyl)hydroxyphosphinyl]oxy]-2-phenylethanoic acid;

2-[[(tetrahydrofuranyl)hydroxyphosphinyl]oxy]-2-phenylethanoic acid;

2-[[(2-indolyl)hydroxyphosphinyl]oxy]-2-phenylethanoic acid;

2-[[(3-indolyl)hydroxyphosphinyl]oxy]-2-phenylethanoic acid;

2-[[(4-indolyl)hydroxyphosphinyl]oxy]-2-phenylethanoic acid;

2-[[(2-thienyl)hydroxyphosphinyl]oxy]-2-phenylethanoic acid;

2-[[(3-thienyl)hydroxyphosphinyl]oxy]-2-phenylethanoic acid; and

2-[[(4-thienyl)hydroxyphosphinyl]oxy]-2-phenylethanoic acid.

Compounds are also preferably selected from the group of formula III:

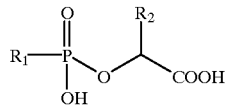

III wherein
R$_1$ is hydrogen, C$_1$–C$_9$ straight or branched chain alkyl, C$_2$–C$_9$ straight or branched chain alkenyl group, C$_3$–C$_8$ cycloalkyl, C$_5$–C$_7$ cycloalkenyl, or Ar$_1$; and
R$_2$ is Ar$_1$, wherein said aryl group may be optionally substituted with carboxylic acid.

Particular species wherein R$_1$ is heterocyclic may be easily made and used by persons of ordinary skill in the art in accordance with the teachings provided herein and known in the art.

Compounds of the present invention wherein R$_1$ is benzyl, R$_2$ is a heterocyclic group, and X is oxygen are selected from the group consisting of:

2-[[benzylhydroxyphosphinyl]oxy]-2-(2-pyridyl)ethanoic acid;
2-[[benzylhydroxyphosphinyl]oxy]-2-(3-pyridyl)ethanoic acid;
2-[[benzylhydroxyphosphinyl]oxy]-2-(4-pyridyl)ethanoic acid;
2-[[benzylhydroxyphosphinyl]oxy]-2-(tetrahydrofuranyl)ethanoic acid;
2-[[benzylhydroxyphosphinyl]oxy]-2-(2-indolyl)ethanoic acid;
2-[[benzylhydroxyphosphinyl]oxy]-2-(3-indolyl)ethanoic acid;
2-[[benzylhydroxyphosphinyl]oxy]-2-(4-indolyl)ethanoic acid;
2-[[benzylhydroxyphosphinyl]oxy]-2-(2-thienyl)ethanoic acid;
2-[[benzylhydroxyphosphinyl]oxy]-2-(3-thienyl)ethanoic acid; and
2-[[benzylhydroxyphosphinyl]oxy]-2-(4-thienyl)ethanoic acid.

Preferred phosphoramidate compounds are selected from formula IV:

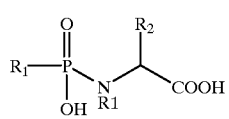

IV wherein
R$_1$ is hydrogen, C$_1$–C$_9$ straight or branched chain alkyl, C$_2$–C$_9$ straight or branched chain alkenyl group, C$_3$–C$_8$ cycloalkyl, C$_5$–C$_7$ cycloalkenyl, or Ar$_1$; and
R$_2$ is C$_1$–C$_9$ straight or branched chain alkyl, C$_2$–C$_9$ straight or branched chain alkenyl group, C$_3$–C$_8$ cycloalkyl, C$_5$–C$_7$ cycloalkenyl, or Ar$_1$, wherein said alkyl, alkenyl, cycloalkyl, cycloalkenyl or aryl group may be optionally substituted with carboxylic acid.

In a preferred embodiment, the R groups are straight branched aliphatic or carbocyclic substituents illustrated by the compounds selected from the group of formula IV:

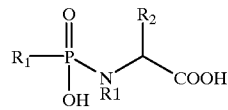

IV wherein
R$_1$ is hydrogen, C$_1$–C$_9$ straight or branched chain alkyl, C$_2$–C$_9$ straight or branched chain alkenyl group, C$_3$–C$_8$ cycloalkyl, C$_5$–C$_7$ cycloalkenyl, 1-naphthyl, 2-naphthyl, or phenyl; and
R$_2$ is C$_1$–C$_9$ straight or branched chain alkyl, C$_2$–C$_9$ straight or branched chain alkenyl group, C$_3$–C$_8$ cycloalkyl, C$_5$–C$_7$ cycloalkenyl, 1-naphthyl, 2-naphthyl, or phenyl, wherein said alkyl, alkenyl, cycloalkyl, cycloalkenyl, 1-naphthyl, 2-naphthyl, or phenyl group may be optionally substituted with carboxylic acid.

Especially preferred compounds of Formula IV of the present invention wherein R$_1$ is a straight or branched aliphatic group or a carbocyclic group, R$_2$ is ethyl which is substituted with a carboxylic acid, and the NR$_1$ is amino are selected from the group consisting of:

2-[[methylhydroxyphosphinyl]amino]pentanedioic acid;
2-[[ethylhydroxyphosphinyl]amino]pentanedioic acid;
2-[[propylhydroxyphosphinyl]amino]pentanedioic acid;
2-[[butylhydroxyphosphinyl]amino]pentanedioic acid;
2-[[cyclohexylhydroxyphosphinyl]amino]pentanedioic acid;
2-[[(cyclohexyl)methylhydroxyphosphinyl]amino]pentanedioic acid;
2-[[phenylhydroxyphosphinyl]amino]pentanedioic acid;
2-[[benzylhydroxyphosphinyl]amino]pentanedioic acid;
2-[[phenylethylhydroxyphosphinyl]amino]pentanedioic acid;
2-[[phenylpropylhydroxyphosphinyl]amino]pentanedioic acid;
2-[[phenylbutylhydroxyphosphinyl]amino]pentanedioic acid;
2-[(4-methylbenzyl)hydroxyphosphinyl]amino]pentanedioic acid;
2-[[(4-fluorobenzyl)hydroxyphosphinyl]amino]pentanedioic acid;
2-[[(2-fluorobenzyl)hydroxyphosphinyl]amino]pentanedioic acid;
2-[[(pentafluorobenzyl)hydroxyphosphinyl]amino]pentanedioic acid;
2-[[(methoxybenzyl)hydroxyphosphinyl]amino]pentanedioic acid;
2-[[(4-fluorophenyl)hydroxyphosphinyl]amino]pentanedioic acid;
2-[[((hydroxy)phenylmethyl)hydroxyphosphinyl]amino]pentanedioic acid;
2-[[(3-methylbenzyl)hydroxyphosphinyl]amino]pentanedioic acid;
2-[(phosphono)amino]pentanedioic acid;
2-[[(3-trifluoromethylbenzyl)hydroxyphosphinyl]amino]pentanedioic acid;
2-[[(2,3,4-trimethoxyphenyl)hydroxyphosphinyl]amino]pentanedioic acid;
2-[[(1-naphthyl)hydroxyphosphinyl]amino]pentanedioic acid;

2-[[(2-naphthyl)hydroxyphosphinyl]amino]pentanedioic acid;

2-[[(1-naphthyl)methylhydroxyphosphinyl]amino] pentanedioic acid;

2-[[(2-naphthyl)methylhydroxyphosphinyl]amino] pentanedioic acid;

2-[[(1-naphthyl)ethylhydroxyphosphinyl]amino] pentanedioic acid;

2-[[(2-naphthyl)ethylhydroxyphosphinyl]amino] pentanedioic acid;

2-[[(1-naphthyl)propylhydroxyphosphinyl]amino] pentanedioic acid;

2-[[(2-naphthyl)propylhydroxyphosphinyl]amino] pentanedioic acid;

2-[[(1-naphthyl)butylhydroxyphosphinyl]amino] pentanedioic acid;

2-[(2-naphthyl)butylhydroxyphosphinyl]amino] pentanedioic acid; and

2-[[(phenylprop-2-enyl)hydroxyphosphinyl]amino] pentanedioic acid.

Especially preferred compounds of Formula IV of the present invention wherein $R_1$ is a straight or branched aliphatic group or a carbocyclic group, $R_2$ is ethyl which is substituted with a carboxylic acid, and the $NR_1$ is amino are selected from the group consisting of:

2-[(benzylhydroxyphosphinyl)amino]pentanedioic acid;

2-[(phenylhydroxyphosphinyl)amino]pentanedioic acid;

2-[[((hydroxy)phenylmethyl)hydroxyphosphinyl]amino] pentanedioic acid;

2-[(butylhydroxyphosphinyl)amino]pentanedioic acid;

2-[[(3-methylbenzyl)hydroxyphosphinyl]amino] pentanedioic acid;

2-[(3-phenylpropylhydroxyphosphinyl)amino] pentanedioic acid;

2-[[(4-fluorophenyl)hydroxyphosphinyl]amino] pentanedioic acid;

2-[(methylhydroxyphosphinyl)amino]pentanedioic acid;

2-[(phenylethylhydroxyphosphinyl)amino]pentanedioic acid;

2-[[(4-methylbenzyl)hydroxyphosphinyl]amino] pentanedioic acid;

2-[[(4-fluorobenzyl)hydroxyphosphinyl]amino] pentanedioic acid;

2-[[(4-methoxybenzyl)hydroxyphosphinyl]amino] pentanedioic acid;

2-[[(2-fluorobenzyl)hydroxyphosphinyl]amino] pentanedioic acid;

2-[[(pentafluorobenzyl)hydroxyphosphinyl]amino] pentanedioic acid;

2-[(phosphono)amino]pentanedioic acid; and

2-[[(3-trifluoromethylbenzyl)hydroxyphosphinyl]amino] pentanedioic acid.

Compounds of the present invention wherein $R_1$ is a straight or branched aliphatic group or a carbocyclic group, $R_2$ is phenyl, and X is amino are selected from the group consisting of:

2-[[methylhydroxyphosphinyl]amino]-2-phenylethanoic acid;

2-[[ethylhydroxyphosphinyl]amino]-2-phenylethanoic acid;

2-[[propylhydroxyphosphinyl]amino]-2-phenylethanoic acid;

2-[[butylhydroxyphosphinyl]amino]-2-phenylethanoic acid;

2-[[cyclohexylhydroxyphosphinyl]amino]-2-phenylethanoic acid;

2-[[(cyclohexyl)methylhydroxyphosphinyl]amino]-2-phenylethanoic acid;

2-[[phenylhydroxyphosphinyl]amino]-2-phenylethanoic acid;

2-[[benzylhydroxyphosphinyl]amino]-2-phenylethanoic acid;

2-[[phenylethylhydroxyphosphinyl]amino]-2-phenylethanoic acid;

2-[[phenylpropylhydroxyphosphinyl]amino]-2-phenylethanoic acid;

2-[[phenylbutylhydroxyphosphinyl]amino]-2-phenylethanoic acid;

2-[[(2,3,4-trimethoxyphenyl)-3-hydroxyphosphinyl] amino]-2-phenylethanoic acid;

2-[[(1-naphthyl)hydroxyphosphinyl]amino]-2-phenylethanoic acid;

2-[[(2-naphthyl)hydroxyphosphinyl]amino]-2-phenylethanoic acid;

2-[[(1-naphthyl)methylhydroxyphosphinyl)]amino]-2-phenylethanoic acid;

2-[[(2-naphthyl)methylhydroxyphosphinyl]amino]-2-phenylethanoic acid;

2-[[(1-naphthyl)ethylhydroxyphosphinyl]amino]-2-phenylethanoic acid;

2-[[(2-naphthyl)ethylhydroxyphosphinyl]amino]-2-phenylethanoic acid;

2-[[(1-naphthyl)propylhydroxyphosphinyl]amino]-2-phenylethanoic acid;

2-[[(2-naphthyl)propylhydroxyphosphinyl]amino]-2-phenylethanoic acid;

2-[[(1-naphthyl)butylhydroxyphosphinyl]amino]-2-phenylethanoic acid;

2-[[(2-naphthyl)butylhydroxyphosphinyl]amino]-2-phenylethanoic acid; and

2-[[phenylprop-2-enylhydroxyphosphinyl]amino]-2-phenylethanoic acid.

Although not limited to any one particular species, a highly preferred phosphoramidate species where $R_1$ is aliphatic or carbocyclic, $R_2$ is ethyl which is substituted with carboxylic acid, and X is amino is 2-[[benzylhydroxyphosphinyl]amino]pentanedioic acid.

Other especially preferred compounds are selected from the group consisting of:

phosphoramidate derivatives wherein X is amino, $R_1$ is a straight or branched aliphatic group or a carbocyclic group, and $R_2$ is an $C_2$–$C_8$ alkyl or alkenyl chain which is substituted with a carboxylic acid. Exemplary species include:

2-[(methylhydroxyphosphinyl)amino]hexanedioic acid;

2-[(benzylhydroxyphosphinyl)amino]hexanedioic acid;

2-[(methylhydroxyphosphinyl)amino]heptanedioic acid;

2-[(benzylhydroxyphosphinyl)amino]heptanedioic acid;

2-[(methylhydroxyphosphinyl)amino]octanedioic acid;

2-[(benzylhydroxyphosphinyl)amino]octanedioic acid;

2-[(methylhydroxyphosphinyl)amino]nonanedioic acid;

2-[(benzylhydroxyphosphinyl)amino]nonanedioic acid;

2-[(methylhydroxyphosphinyl)amino]decanedioic acid; and

2-[(benzylhydroxyphosphinyl)amino]decanedioic acid.

Other especially preferred compounds are selected from the group consisting of:
phosphoramidate derivatives wherein X is amino, $R_1$ is benzyl, and $R_2$ is a straight or branched aliphatic group or a carbocyclic group. Exemplary species include:

2-[[benzylhydroxyphosphinyl]amino]-2-methylethanoic acid;
2-[[benzylhydroxyphosphinyl]amino]-2-ethylethanoic acid;
2-[[benzylhydroxyphosphinyl]amino]-2-propylethanoic acid;
2-[[benzylhydroxyphosphinyl]amino]-2-butylethanoic acid;
2-[[benzylhydroxyphosphinyl]amino]-2-cyclohexylethanoic acid;
2-[[benzylhydroxyphosphinyl]amino]-2-(cyclohexyl)methylethanoic acid;
2-[[benzylhydroxyphosphinyl]amino]-2-phenylethanoic acid;
2-[[benzylhydroxyphosphinyl]amino-2-benzylethanoic acid;
2-[[benzylhydroxyphosphinyl]amino]-2-phenylethylethanoic acid;
2-[[benzylhydroxyphosphinyl]amino]-2-phenylpropylethanoic acid;
2-[[benzylhydroxyphosphinyl]amino]-2-phenylbutylethanoic acid;
2-[[benzylhydroxyphosphinyl]amino]-2-(2,3,4-trimethoxyphenyl)ethanoic acid;
2-[[benzylhydroxyphosphinyl]amino]-2-(1-naphthyl)ethanoic acid;
2-[[benzylhydroxyphosphinyl]amino]-2-(2-naphthyl)ethanoic acid;
2-[[benzylhydroxyphosphinyl]amino]-2-(1-naphthyl)methylethanoic acid;
2-[[benzylhydroxyphosphinyl]amino]-2-(2-naphthyl)methylethanoic acid;
2-[[benzylhydroxyphosphinyl]amino]-2-(1-naphthyl)ethylethanoic acid;
2-[[benzylhydroxyphosphinyl]amino]-2-(2-naphthyl)ethylethanoic acid;
2-[[benzylhydroxyphosphinyl]amino]-2-(1-naphthyl)propylethanoic acid;
2-[[benzylhydroxyphosphinyl]amino]-2-(2-naphthyl)propylethanoic acid;
2-[[benzylhydroxyphosphinyl]amino]-2-(1-naphthyl)butylethanoic acid;
2-[[benzylhydroxyphosphinyl]amino]-2-(2-naphthyl)butylethanoic acid; and
2-[[benzylhydroxyphosphinyl]amino]-2-phenylprop-2-enylethanoic acid.

Especially preferred methods utilize compounds wherein $R_1$ is said alkyl, alkenyl, cycloalkyl, or aryl group which is substituted with a heterocyclic group, $R_2$ is ethyl which is substituted with carboxylic acid, and X is amino are selected from the group consisting of:

2-[[(2-pyridyl)methylhydroxyphosphinyl]amino] pentanedioic acid;
2-[[(3-pyridyl)methylhydroxyphosphinyl]amino] pentanedioic acid;
2-[[(4-pyridyl)methylhydroxyphosphinyl]amino] pentanedioic acid;
2-[[(3-pyridyl)ethylhydroxyphosphinyl]amino] pentanedioic acid;
2-[[(3-pyridyl)propylhydroxyphosphinyl]amino] pentanedioic acid;
2-[[(tetrahydrofuranyl)methylhydroxyphosphinyl]amino] pentanedioic acid;
2-[[(tetrahydrofuranyl)ethylhydroxyphosphinyl]amino] pentanedioic acid;
2-[[(tetrahydrofuranyl)propylhydroxyphosphinyl]amino] pentanedioic acid;
2-[[(2-indolyl)methylhydroxyphosphinyl]amino] pentanedioic acid;
2-[[(3-indolyl)methylhydroxyphosphinyl]amino] pentanedioic acid;
2-[[(4-indolyl)methylhydroxyphosphinyl]amino] pentanedioic acid;
2-[[(3-indolyl)ethylhydroxyphosphinyl]amino] pentanedioic acid;
2-[[(3-indolyl)propylhydroxyphosphinyl]amino] pentanedioic acid;
2-[[(2-thienyl)methylhydroxyphosphinyl]amino] pentanedioic acid;
2-[[(3-thienyl)methylhydroxyphosphinyl]amino] pentanedioic acid;
2-[[(4-thienyl)methylhydroxyphosphinyl]amino] pentanedioic acid;
2-[[(3-thienyl)ethylhydroxyphosphinyl]amino] pentanedioic acid; and
2-[[(3-thienyl)propylhydroxyphosphinyl]amino] pentanedioic acid.

Especially preferred methods utilize compounds wherein $R_1$ is said alkyl, alkenyl, cycloalkyl, or aryl group which is substituted with a heterocyclic group, $R_2$ is phenyl, and X amino are selected from the group consisting of:

2-[[(2-pyridyl)methylhydroxyphosphinyl]amino]-2-phenylethanoic acid;
2-[[(3-pyridyl)methylhydroxyphosphinyl]amino]-2-phenylethanoic acid;
2-[[(4-pyridyl)methylhydroxyphosphinyl]amino]-2-phenylethanoic acid;
2-[[(3-pyridyl)ethylhydroxyphosphinyl]amino]-2-phenylethanoic acid;
2-[[(3-pyridyl)propylhydroxyphosphinyl]amino]-2-phenylethanoic acid;
2-[[(tetrahydrofuranyl)methylhydroxyphosphinyl]amino]-2-phenylethanoic acid;
2-[[(tetrahydrofuranyl)ethylhydroxyphosphinyl]amino]-2-phenylethanoic acid;
2-[[(tetrahydrofuranyl)propylhydroxyphosphinyl]amino]-2-phenylethanoic acid;
2-[[(2-indolyl)methylhydroxyphosphinyl]amino]-2-phenylethanoic acid;
2-[[(3-indolyl)methylhydroxyphosphinyl]amino]-2-phenylethanoic acid;
2-[[(4-indolyl)methylhydroxyphosphinyl]amino]-2-phenylethanoic acid;
2-[[(3-indolyl)ethylhydroxyphosphinyl]amino]-2-phenylethanoic acid;
2-[[(3-indolyl)propylhydroxyphosphinyl]amino]-2-phenylethanoic acid;
2-[[(2-thienyl)methylhydroxyphosphinyl]amino]-2-phenylethanoic acid;

2-[[(3-thienyl)methylhydroxyphosphinyl]amino]-2-phenylethanoic acid;

2-[[(4-thienyl)methylhydroxyphosphinyl]amino]-2-phenylethanoic acid;

2-[[(3-thienyl)ethylhydroxyphosphinyl]amino]-2-phenylethanoic acid; and

2-[[(3-thienyl)propylhydroxyphosphinyl]amino]-2-phenylethanoic acid.

Especially preferred methods utilize compounds wherein $R_1$ is benzyl, $R_2$ is said alkyl, alkenyl, cycloalkyl, or aryl group which is substituted with a heterocyclic group, and X is amino are selected from the group consisting of:

2-[[benzylhydroxyphosphinyl]amino]-2-(2-pyridyl)methylethanoic acid;

2-[[benzylhydroxyphosphinyl]amino]-2-(3-pyridyl)methylethanoic acid;

2-[[benzylhydroxyphosphinyl]amino]-2-(4-pyridyl)methylethanoic acid;

2-[[benzylhydroxyphosphinyl]amino]-2-(3-pyridyl)ethylethanoic acid;

2-[[benzylhydroxyphosphinyl]amino]-2-(3-pyridyl)propylethanoic acid;

2-[[benzylhydroxyphosphinyl]amino]-2-(tetrahydrofuranyl)methylethanoic acid;

2-[[benzylhydroxyphosphinyl]amino]-2-(tetrahydrofuranyl)ethylethanoic acid;

2-[[benzylhydroxyphosphinyl]amino]-2-(tetrahydrofuranyl)propylethanoic acid;

2-[[benzylhydroxyphosphinyl]amino]-2-(2-indolyl)methylethanoic acid;

2-[[benzylhydroxyphosphinyl]amino]-2-(3-indolyl)methylethanoic acid;

2-[[benzylhydroxyphosphinyl]amino]-2-(4-indolyl)methylethanoic acid;

2-[[benzylhydroxyphosphinyl]amino]-2-(3-indolyl)ethylethanoic acid;

2-[[benzylhydroxyphosphinyl]amino]-2-(3-indolyl)propylethanoic acid;

2-[[benzylhydroxyphosphinyl]amino]-2-(2-thienyl)methylethanoic acid;

2-[[benzylhydroxyphosphinyl]amino]-2-(3-thienyl)methylethanoic acid;

2-[[benzylhydroxyphosphinyl]amino]-2-(4-thienyl)methylethanoic acid;

2-[[benzylhydroxyphosphinyl]amino]-2-(3-thienyl)ethylethanoic acid; and

2-[[benzylhydroxyphosphinyl]amino]-2-(3-thienyl)propylethanoic acid.

In another preferred embodiment, $R_1$ is a heterocyclic substituent illustrated by the compounds selected from the group of formula IV:

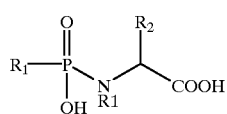

IV wherein
$R_1$ is $Ar_1$; and
$R_2$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$, wherein said alkyl, alkenyl, cycloalkyl, cycloalkenyl or aryl group may be optionally substituted with carboxylic acid.

Especially preferred compounds wherein $R_1$ is a heterocyclic group, $R_2$ is ethyl which is substituted with carboxylic acid, and X is amino are selected from the group consisting of:

2-[[(2-pyridyl)hydroxyphosphinyl]amino]pentanedioic acid;

2-[[(3-pyridyl)hydroxyphosphinyl]amino]pentanedioic acid;

2-[[(4-pyridyl)hydroxyphosphinyl]amino]pentanedioic acid;

2-[[(tetrahydrofuranyl)hydroxyphosphinyl]amino]pentanedioic acid;

2-[[(2-indolyl)hydroxyphosphinyl]amino]pentanedioic acid;

2-[[(3-indolyl)hydroxyphosphinyl]amino]pentanedioic acid;

2-[[(4-indolyl)hydroxyphosphinyl]amino]pentanedioic acid;

2-[[(2-thienyl)hydroxyphosphinyl]amino]pentanedioic acid;

2-[[(3-thienyl)hydroxyphosphinyl]amino]pentanedioic acid; and

2-[[(4-thienyl)hydroxyphosphinyl]amino]pentanedioic acid.

Compounds of the present invention wherein $R_1$ is a heterocyclic group, $R_2$ is phenyl, and X is amino are selected from the group consisting of:

2-[[(2-pyridyl)hydroxyphosphinyl]amino]-2-phenylethanoic acid;

2-[[(3-pyridyl)hydroxyphosphinyl]amino]-2-phenylethanoic acid;

2-[[(4-pyridyl)hydroxyphosphinyl]amino]-2-phenylethanoic acid;

2-[[(tetrahydrofuranyl)hydroxyphosphinyl]amino]-2-phenylethanoic acid;

2-[[(2-indolyl)hydroxyphosphinyl]amino]-2-phenylethanoic acid;

2-[[(3-indolyl)hydroxyphosphinyl]amino]-2-phenylethanoic acid;

2-[(4-indolyl)hydroxyphosphinyl amino]-2-phenylethanoic acid;

2-[[(2-thienyl)hydroxyphosphinyl]amino]-2-phenylethanoic acid;

2-[[(3-thienyl)hydroxyphosphinyl]amino]-2-phenylethanoic acid; and

2-[[(4-thienyl)hydroxyphosphinyl]amino]-2-phenylethanoic acid.

Compounds are also preferably selected from the group of formula IV:

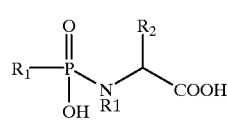

IV wherein
$R_1$ is hydrogen, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; and $R_2$ is $Ar_1$; wherein said aryl group may be optionally substituted with carboxylic acid.

Particular species wherein $R_2$ is heterocyclic may be easily made and used by persons of ordinary skill in the art in accordance with the teachings provided herein and known in the art.

Compounds of the present invention wherein $R_1$ is benzyl, $R_2$ is heterocyclic, and X is amino are selected from the group consisting of:

2-[[benzylhydroxyphosphinyl]amino]-2-(2-pyridyl)ethanoic acid;

2-[[benzylhydroxyphosphinyl]amino]-2-(3-pyridyl)ethanoic acid;

2-[[benzylhydroxyphosphinyl]amino]-2-(4-pyridyl)ethanoic acid;

2-[[benzylhydroxyphosphinyl]amino]-2-(tetrahydrofuranyl)ethanoic acid;

2-[[benzylhydroxyphosphinyl]amino]-2-(2-indolyl)ethanoic acid;

2-[[benzylhydroxyphosphinyl]amino]-2-(3-indolyl)ethanoic acid;

2-[[benzylhydroxyphosphinyl]amino]-2-(4-indolyl)ethanoic acid;

2-[[benzylhydroxyphosphinyl]amino]-2-(2-thienyl)ethanoic acid;

2-[[benzylhydroxyphosphinyl]amino]-2-(3-thienyl)ethanoic acid; and

2-[[benzylhydroxyphosphinyl]amino]-2-(4-thienyl)ethanoic acid.

Synthesis of Compounds

The compounds of the present invention can be readily prepared by standard techniques of organic chemistry, utilizing the general synthetic pathways depicted below (see Schemes I–IX). Precursor compounds may be prepared by methods known in the art, such as those described in the method of Jackson et al. (*J. Med. Chem.* 39(2), 619–622, Design, Synthesis, and Biological Activity of a Potent Inhibitor of the Neuropeptidase N-Acetylated a-Linked Acidic Dipeptidase) and, for example, in Froestl et al. (*J. Med. Chem.*, 1995, 38, 3313–3331, Phosphinic Acid Analogues of GABA).

SCHEME I

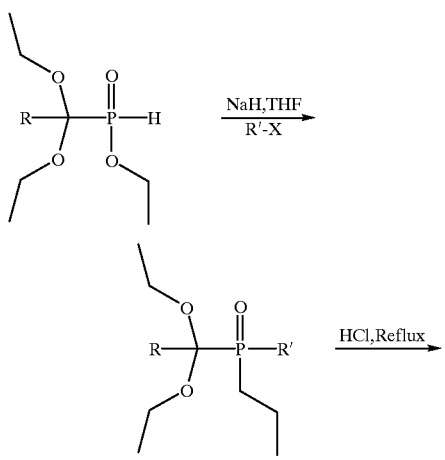

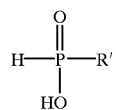

Production of compounds containing the R group substitutions can be easily made utilizing known methods. Further methods of synthesizing phosphinic acid esters are also described in *J. Med. Chem.*, 1988, 31, 204–212, and may be found in Scheme II, below.

SCHEME II

Method A

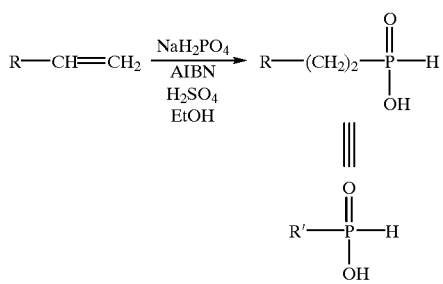

| A. | $R' = (CH_2)_3Ph$ | H. | n-$C_7H_{15}$ |
| B. | $(CH_2)_4Ph$ | I. | n-$C_8H_{17}$ |
| C. | $(CH_2)_5Ph$ | J. | n-$C_9H_{19}$ |
| D. | $(CH_2)_4(P$—F—$Ph)$ | K. | n-$C_{10}H_{21}$ |
| E. | $(CH_2)_4$—(3-pyridyl) | L. | $CH_2(CH)(CH_3)C_4H_9$ |
| F. | n-$C_5H_{11}$ | M. | $CH_2(CH_3)CH(CH_3)_2$ |
| G. | n-$C_6H_{13}$ | | |

Method B

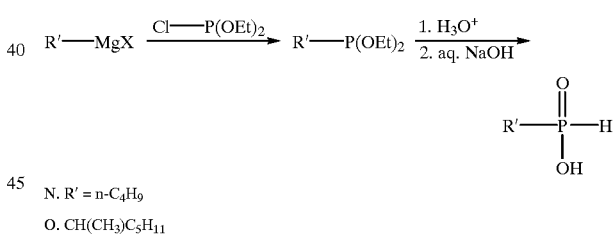

N. $R' = n-C_4H_9$

O. $CH(CH_3)C_5H_{11}$

Starting with the aforementioned phosphinic acid esters, there are a variety of routes that can be used to prepare the compounds of the present invention. For example, a general route was recently described in *J. Med. Chem.*, 1996, 39, 619–622, and is set forth below in Scheme III.

SCHEME III

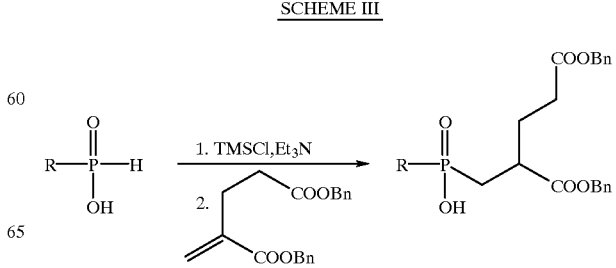

-continued

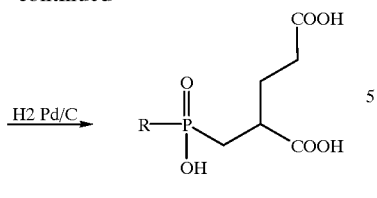

Another route for preparing the compounds of the present invention is as set forth below in scheme IV and Scheme V. Scheme IV and Scheme V also show a phosphinic acid derivative as a starting material to prepare the compounds of the present invention and the R group is contemplated as including any reasonable chemical substitution and includes without limitation the R groups listed in Scheme II and within the specification.

SCHEME IV

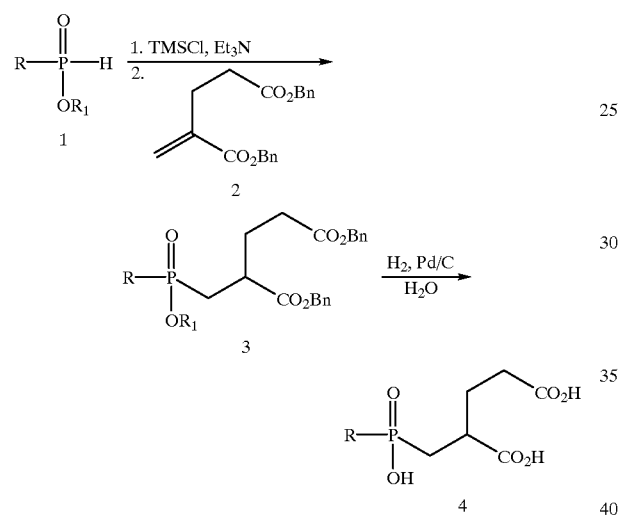

SCHEME V

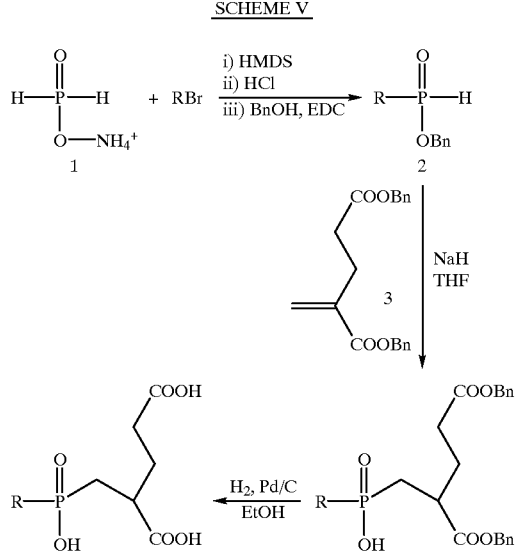

Another route of preparing the compounds of the present invention allows for aromatic substitution at R1 and is set forth below in Scheme VI.

SCHEME VI

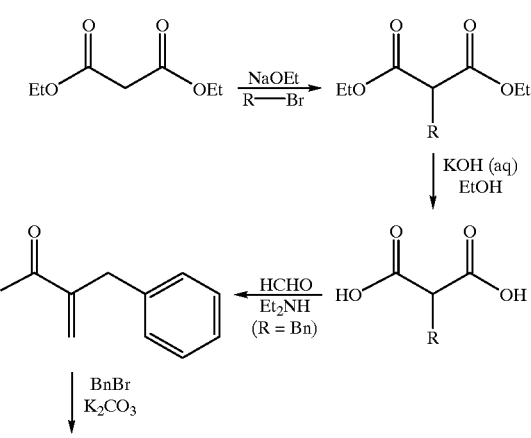

Another route of preparing the compounds of the present invention allows for aromatic substitution at the $R_2$ position and is set forth below in Scheme VII.

SCHEME VII

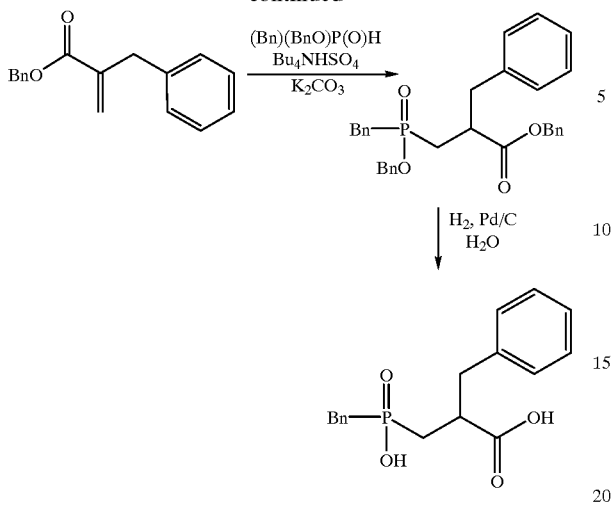

Preparation of the compounds of the present invention wherein X is NR1 is set forth below in Scheme VIII.

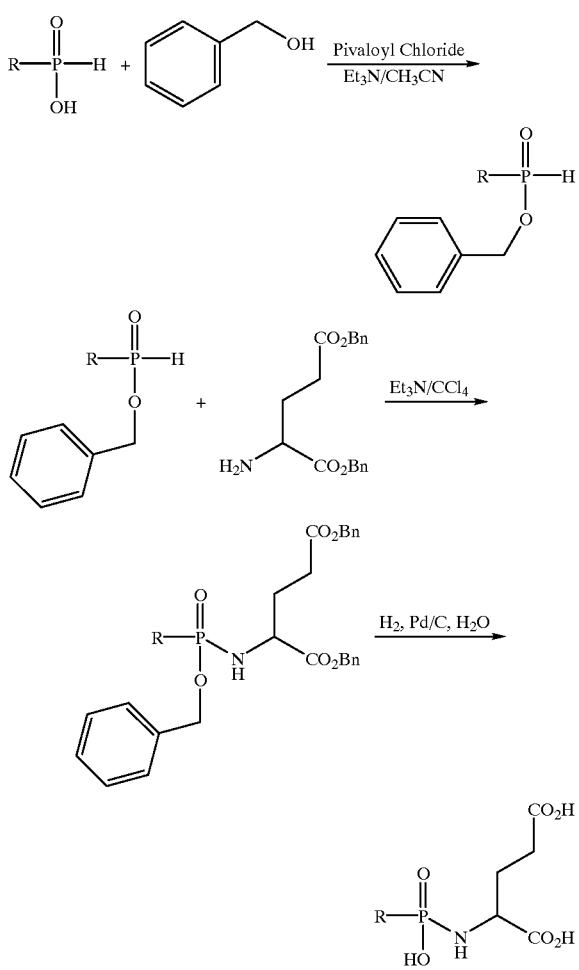

Preparation of the compounds of the present invention wherein X is oxygen is set forth below in Scheme IX.

SCHEME IX

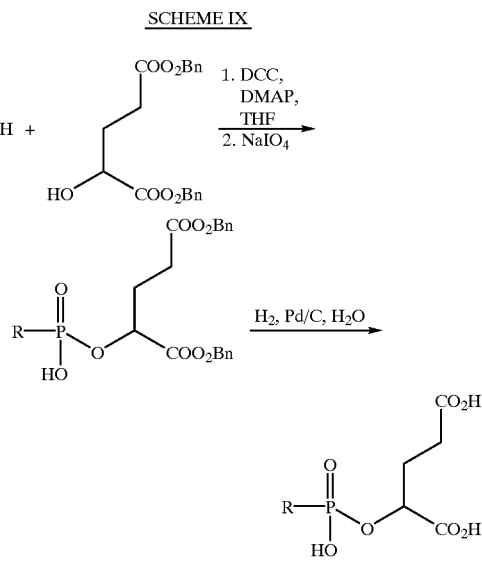

Pharmaceutical Compositions of the Present Invention

The present invention also relates to a pharmaceutical composition comprising:

(i) a therapeutically effective amount of a compound of formulas I, II, III or IV; and (ii) a pharmaceutically acceptable carrier.

In another preferred embodiment, the pharmaceutical composition further comprises a therapeutic agent selected from the group consisting of therapeutic hormones, chemotherapeutic agents, monoclonal antibodies, antiangiogenesis agents, radiolabelled compounds, antineoplastic agents and mixtures thereof. Examples of therapeutic hormones include diethylstilbestrol (DES), leuprolide, flutamide, cyproterone acetate, ketoconazole and amino glutethimide are preferred. Examples of antineoplastic agents include 5-fluorouracil, vinblastine sulfate, estramustine phosphate, suramin and strontium-89. Examples of chemotherapeutic agents include buserelin, chlorotranisene, chromic phosphate, cisplatin, cyclophosphamide, dexamethasone, doxorubicin, estradiol, estradiol valerate, estrogens conjugated and esterified, estrone, ethinyl estradiol, floxuridine, goserelin, hydroxyurea, melphalan, methotrexate, mitomycin and prednisone.

In a further preferred embodiment, the compound of formula I, II, III or IV is present in an amount that is effective for inhibiting NAALADase activity in an animal or treating a prostate disease in an animal.

Process for Preparing Pharmaceutical Compositions

In yet another preferred embodiment, a process for preparing a pharmaceutical composition or medicament containing a compound of the present invention for treating a disease is also contemplated.

Methods of Use of the Present Invention i) Method of Inhibiting NAALADase Enzyme Activity The present invention further relates to a method of inhibiting NAALADase enzyme activity in an animal, comprising administering an effective amount of a compound of formula I, II, III or IV to said animal.

ii) Method of Treating a Prostate Disease

The present invention also relates to a method of treating a prostate disease in an animal, comprising administering an effective amount of a compound of formula I, II, III or IV to said animal.

In a preferred embodiment, said prostate disease is prostate cancer such as prostatic adenocarcinoma, benign prostatic hyperplasia, or conditions involving the prostate requiring administration of the compounds of the present invention, such prostatic intraepithelial neoplasia (PIN).

iii) Method of Treating Cancer

In addition to prostate cancer, other forms of cancer that may be treated with the compounds of the present invention include without limitation: ACTH-producing tumors, acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer(small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva and Wilm's tumor.

The compounds of the present invention are particularly useful in treating cancer of tissues where NAALADase enzymes reside. Such tissues include the prostate as well as the brain, kidney and testis.

For patients who initially present without advanced or metastatic cancer, NAALADase inhibitor based drugs are used as an immediate initial therapy prior to surgery and radiation therapy, and as a continuous post-treatment therapy in patients at risk for recurrence or metastasis (based upon high PSA, high Gleason's score, locally extenstive disease, and/or pathological evidence of tumor invasion In the surgical specimen). The goal in these patients is to inhibit the growth of potentially metastatic cells from the primary tumor during surgery or radiotherapy and inhibit the growth of tumor cells from undetectable residual primary tumor.

For patients who initially present with advanced or metastatic cancer, NAALADase inhibitor based drugs are used as a continuous supplement to, or possible as a replacement for hormonal ablation. The goal in these patients is to slow tumor cell growth from both the untreated primary tumor and from the existing metastatic lesions.

In addition, the invention may be particularly efficacious during post-surgical recovery, where the present compositions and methods may be particularly effective in lessening the chances of recurrence of a tumor engendered by shed cells that cannot be removed by surgical intervention.

iv) Diagnostic Kits

The present invention also includes a diagnostic kit for performing the methods of the present invention and may contain compounds and/or compositions containing the compounds of the present invention. Radiolabelled compounds and monoclonal antibodies may be used in a manner so as to provide diagnostic information. Examples of diagnostic information and uses include determining the type of disease, the progress of the particular disease, the location of cells targeted by a NAALADase inhibitor, radiolabelled compound or monoclonal antibody, and similar diagnostic uses known to persons skilled in the art.

Route of Administration

In the methods of the present invention, the compounds may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneal, intrathecal, intraventricular, intrasternal or intracranial injection and infusion techniques. Invasive techniques are preferred, particularly direct administration to damaged neuronal tissue.

To be effective therapeutically as central nervous system targets, the compounds of the present invention should readily penetrate the blood-brain barrier when peripherally administered. Compounds which cannot penetrate the blood-brain barrier can be effectively administered by an intraventricular route.

The compounds may also be administered in the form of sterile injectable preparations, for example, as sterile injectable aqueous or oleaginous suspensions. These suspensions can be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated forms, are useful in the preparation of injectables. These oil solutions or suspensions may also contain long-chain alcohol diluents or dispersants.

Additionally, the compounds may be administered orally in the form of capsules, tablets, aqueous suspensions or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

The compounds may further be administered rectally in the form of suppositories. These compositions can be prepared by mixing the drug with suitable non-irritating excipients which are solid at room temperature, but liquid at rectal temperature such that they will melt in the rectum to release the drug. Such excipients include cocoa butter, beeswax and polyethylene glycols.

Moreover, the compounds may be administered topically, especially when the conditions addressed for treatment involve areas or organs readily accessible by topical application, including neurological disorders of the eye, the skin or the lower intestinal tract.

For topical application to the eye, or ophthalmic use, the compounds can be formulated as micronized suspensions in isotonic, pH adjusted sterile saline or, preferably, as a solution in isotonic, pH adjusted sterile saline, either with or without a preservative such as benzylalkonium chloride.

Alternatively, the compounds may be formulated into ointments, such as petrolatum.

For topical application to the skin, the compounds can be formulated into suitable ointments containing the compounds suspended or dissolved in, for example, mixtures with one or more of the following: mineral oil, limpid petrolatum, white petrolatum, propylene glycol, polyoxyethylene polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 50, cetyl ester wax, cetearyl alcohol, 2-octyldodecanol, benzyl alcohol and water.

Topical application to the lower intestinal tract can be effected in rectal suppository formulations (see above) or in suitable enema formulations.

The compounds of the present invention may be administered by a single dose, multiple discrete doses or continuous infusion. Since the compounds are small, easily diffusible and relatively stable, they are well suited to continuous infusion. Pump means, particularly subcutaneous pump means, are preferred for continuous infusion.

Compositions and methods of the invention also may utilize controlled release technology. Thus, for example, NAALADase inhibitors may be incorporated into a polymer matrix for controlled release over a period of days. Such controlled release films are well known to the art. Examples of polymers commonly employed for this purpose that may be used in the present invention include nondegradable ethylene-vinyl acetate copolymer and degradable lactic acid-glycolic acid copolymers. Certain hydrogels such as poly(hydroxyethylmethacrylate) or poly(vinylalcohol) also may be useful.

Dosage

Dose levels on the order of about 0.1 mg to about 10,000 mg of the active ingredient compound are useful in the treatment of the above conditions, with preferred levels being about 0.1 mg to about 1,000 mg. The specific dose level for any particular patient will vary depending upon a variety of factors, including the activity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful, particularly in determining effective doses for treating cancer. The considerations for determining the proper dose levels are well known in the art.

In a preferred embodiment, the compounds of the present invention are administered in lyophilized form. In this case, 1 to 100 mg of a compound of the present invention may be lyophilized in individual vials, together with a carrier and a buffer, such as mannitol and sodium phosphate. The compound may be reconstituted in the vials with bacteriostatic water before administration.

As previously mentioned, the compounds of the present invention may be administered in combination with one or more therapeutic agents, including chemotherapeutic agents. TABLE I provides known median dosages for selected chemotherapeutic agents. Specific dose levels for these agents will depend upon considerations such as those identified above for the compounds of the present invention.

TABLE I

| CHEMOTHERAPEUTIC AGENT | MEDIAN DOSAGE |
| --- | --- |
| Asparaginase | 10,000 units |
| Bleomycin Sulfate | 15 units |
| Carboplatin | 50–450 mg |
| Carmustine | 100 mg |
| Cisplatin | 10–50 mg |
| Cladribine | 10 mg |
| Cyclophosphamide (lyophilized) | 100 mg–2 gm |
| Cyclophosphamide (non-lyophilized) | 100 mg–2 gm |
| Cytarabine (lyophilized powder) | 100 mg–2 gm |
| Dacarbazine | 100 mg–200 mg |
| Dactinomycin | 0.5 mg |
| Daunorubicin | 20 mg |
| Diethylstilbestrol | 250 mg |
| Doxorubicin | 10–150 mg |
| Etidronate | 300 mg |
| Etoposide | 100 mg |
| Floxuridine | 500 mg |
| Fludarabine Phosphate | 50 mg |
| Fluorouracil | 500 mg–5 gm |
| Goserelin | 3.6 mg |
| Granisetron Hydrochloride | 1 mg |
| Idarubicin | 5–10 mg |
| Ifosfamide | 1–3 gm |
| Leucovorin Calcium | 50–350 mg |
| Leuprolide | 3.75–7.5 mg |
| Mechlorethamine | 10 mg |
| Medroxyprogesterone | 1 gm |
| Melphalan | 50 gm |
| Methotrexate | 20 mg–1 gm |
| Mitomycin | 5–40 mg |
| Mitoxantrone | 20–30 mg |
| Ondansetron Hydrochloride | 40 mg |
| Paclitaxel | 30 mg |
| Pamidronate Disodium | 30–*90 mg |
| Pegaspargase | 750 units |
| Plicamycin | 2,500 mcgm |
| Streptozocin | 1 gm |
| Thiotepa | 15 mg |
| Teniposide | 50 mg |
| Vinblastine | 10 mg |
| Vincristine | 1–5 mg |
| Aldesleukin | 22 million units |
| Epoetin Alpha | 2,000–10,000 units |
| Filgrastim | 300–480 mcgm |
| Immune Globulin | 500 mg–10 gm |
| Interferon Alpha-2a | 3–36 million units |
| Interferon Alpha-2b | 3–50 million units |
| Levamisole | 50 mg |
| Octreotide | 1,000–5,000 mcgm |
| Sargramostim | 250–500 mcgm |

Administration Regimen

For the methods of the present invention, any administration regimen regulating the timing and sequence of drug delivery can be used and repeated as necessary to effect treatment. Such regimen may include pretreatment and/or co-administration with additional therapeutic agents.

For patients with prostate cancer that is neither advanced nor metastatic, the compounds of the present invention may be administered (i)prior to surgery or radiation treatment to reduce the risk of metastasis; (ii) during surgery or in conjunction with radiation treatment; and/or (iii) after surgery or radiation therapy to reduce the risk of recurrence and to inhibit the growth of any residual tumorous cells.

For patients with advanced or metastatic prostate cancer, the compounds of the present invention may be administered as a continuous supplement to, or as a replacement for, hormonal ablation in order to slow tumor cell growth in both the untreated primary tumor and the existing metastatic lesions.

The methods of the present invention are particularly useful where shed cells could not be removed by surgical intervention. After post-surgical recovery, the methods of the present invention would be effective in reducing the chances of recurrence of a tumor engendered by such shed cells.

Combination with Other Treatments (i) Surgery and Radiation Treatment

In general, surgery and radiation treatment are employed as potentially curative therapies for patients with localized prostate cancer who are under 70 years of age and are expected to live at least 10 more years.

Approximately 70% of newly diagnosed prostate cancer patients fall into this category. Approximately 90% of these patients (65% of total patients) undergo surgery, while approximately 10%, of these patients (7% of total patients) undergo radiation treatment.

Histopathological examination of surgical specimens reveals that approximately 63% of patients undergoing surgery (40% of total patients) have locally extensive tumors or regional (lymph node) metastasis that was undetected at initial diagnosis. These patients are at a significantly greater risk of recurrence. Approximately 40% of these patients will actually develop recurrence within five years after surgery. Results after radiation treatment are even less encouraging. Approximately 80% of patients who have undergone radiation treatment as their primary therapy have disease persistence or develop recurrence or metastasis within five years after treatment.

Currently, most prostate cancer patients undergoing surgery and radiation treatment do not receive any immediate follow-up therapy. Rather, they are monitored frequently for elevated Prostate Specific Antigen ("PSA"), which is the primary indicator of recurrence or metastasis.

Based on the above statistics, there is considerable opportunity to use the present invention in conjunction with surgery and/or radiation treatment.

(ii) Hormonal Therapy

Hormonal ablation is the most effective palliative treatment for the 10% of patients with metastatic prostate cancer. Hormonal ablation by medication and/or orchiectomy is used to block hormones that promote further growth and metastasis of prostate cancer. With time, both the primary and metastatic tumors of virtually all of these patients become hormone-independent and resistant to therapy. Approximately 50% of patients with metastatic cancer die within three years after initial diagnosis, and 75% of such patients die within five years after diagnosis. Continuous supplementation with the compounds of the present invention may be used to prevent or reverse this potentially metastasis-permissive state.

(iii) Chemotherapy

While chemotherapy has been successful in treating some forms of cancer, it has shown slight therapeutic value in treating prostate cancer where it is generally reserved as a last resort. Accordingly, the opportunity to treat prostate cancer by combining chemotherapy with the methods of the present invention will be rare. When combined, however, such treatments should be more effective than chemotherapy alone in controlling prostate cancer.

(iv) Immunotherapy

The compounds of the present invention may also be used in combination with monoclonal antibodies to treat prostate cancer. Such combined treatment is particularly effective for patients with pelvic lymph node involvement, of which only 34% survive after 5 years. An example of such monoclonal antibodies is cell membrane-specific anti-prostate antibody.

The present invention may also be used with immunotherapies based on polyclonal or monoclonal antibody-derived reagents: Monoclonal antibody-derived reagents are preferred. These reagents are well known in the art, and include radiolabelled monoclonal antibodies such as monoclonal antibodies conjugated with strontium-89.

(v) Cryotherapy

The methods of the present invention may also be used in conjunction with cryotherapy for treatment of prostate cancer.

Experimental Studies

The following experimental studies of compounds of the present invention and of structurally related compounds provide strong evidence that the compounds of the present invention are non-toxic and are effective in inhibiting NAALADase activity, treating glutamate abnormalities and treating prostate diseases.

In Vivo Toxicity of NAALADase Inhibitors

To examine the toxicological effect of NAALADase inhibition in vivo, a group of mice were injected with 2-(phosphonomethyl)pentanedioic acid, a NAALADase inhibitor of high activity, in doses of 1, 5, 10, 30, 100, 300 and 500 mg/kg body weight. The mice were subsequently observed two times per day for 5 consecutive days. The survival rate at each dose level is provided in TABLE II below. The results show that the NAALADase inhibitor is non-toxic to mice, suggesting that the compounds of the present invention would be similarly non-toxic to humans when administered at therapeutically effective amounts.

TABLE II

TOXICOLOGICAL EFFECTS OF NAALADASE INHIBITORS

| Dose (mg/kg) | 1 | 5 | 10 | 30 | 100 | 300 | 500 |
|---|---|---|---|---|---|---|---|
| Survival Rate After 5 days (%) | 100 | 100 | 100 | 100 | 100 | 100 | 66.7 |

In Vitro Assay of NAALADase Activity

The following compounds were tested for in vitro inhibition of NAALADase activity. The results are provided in Tables III(a), III(b), and III(c) below.

TABLE III(a)

IN VITRO ACTIVITY OF NAALADASE INHIBITORS

| Compound | $K_i$ (nM) |
|---|---|
| 2-(phosphonomethyl)pentanedioic acid | 0.275 ± 0.08 |
| 2-(phosphonomethyl)succinic acid | 700.00 ± 67.3 |
| 2-[[2-carboxyethyl)hydroxyphosphinyl]-methyl]pentanedioic acid) | 1.89 ± 0.19 |

2-(phosphonomethyl)pentanedioic acid showed a high level of NAALADase inhibiting activity, with a $K_i$ of 0.27 nM (Table III(a)). The activity of this compound is >1000 times more potent than that of previously described inhibitors. Since 2-(phosphonomethyl)pentanedioic acid is similar in structure to the compounds of the present invention, the results suggest that the compounds of the present invention would also be potent NAALADase inhibitors. By comparison, 2-(phosphonomethyl)succinic acid exhibits much lower NAALADase inhibiting activity, suggesting that a glutamate analog attached to the phosphonic acid contributes to its NAALADase inhibiting activity. The results also show that 2-[[2-carboxyethyl)-hydroxyphosphinyl]methyl]pentanedioic acid, which has an additional carboxylic acid side chain similar to the aspartate residue found in NAAG, exhibits a lower NAALADase inhibiting activity than 2-(phosphonomethyl)-pentanedioic acid.

Table III (b)

Other compounds demonstrating inhibition of NAALADase activity are set forth below in Table III(b). Results of the nine compounds in Table III(b) shows the remarkable Ki activity of a variety of compounds of the present invention. These compounds show NAALADase inhibitory ability wherein R1 comprises an aliphatic group, a aliphatic which is substituted, an aromatic group, and aromatic which is substituted.

TABLE III(b)

In vitro Activity of NAALADase Inhibitors

| COMPOUND | Ki(nM) |
|---|---|
| (benzyl-P(O)(OH)-CH2-CH(CO2H)-CH2CH2-CO2H) | 34 |
| (phenyl-P(O)(OH)-CH2-CH(CO2H)-CH2CH2-CO2H) | 36 |
| (HO-CH(phenyl)-P(O)(OH)-CH2-CH(CO2H)-CH2CH2-CO2H) | 54 |
| (butyl-P(O)(OH)-CH2-CH(CO2H)-CH2CH2-CO2H) | 148 |
| (m-methylphenyl-P(O)(OH)-CH2-CH(CO2H)-CH2CH2-CO2H) | 190 |

TABLE III(b)-continued

In vitro Activity of NAALADase Inhibitors

| COMPOUND | Ki(nM) |
|---|---|
| (phenyl-CH2CH2CH2-P(O)(OH)-CH2-CH(CO2H)-CH2CH2-CO2H) | 231 |
| (4-F-phenyl-P(O)(OH)-CH2-CH(CO2H)-CH2CH2-CO2H) | 532 |
| (methyl-P(O)(OH)-CH2-CH(CO2H)-CH2CH2-CO2H) | 1100 |
| (phenyl-CH2CH2-P(O)(OH)-CH2-CH(CO2H)-CH2CH2-CO2H) | 148 |

Further results, provided in Table III(c), show the remarkable Ki activity of the compounds of the present invention. These compounds show NAALADase inhibition wherein R1 comprises a substituted aliphatic (benzyl) which is further substituted.

TABLE III(c)

in vitro Activity of NAALADase Inhibitors

| Compound | Ki Value (nM) |
|---|---|
| (4-methylbenzyl-P(O)(OH)-CH2-CH(COOH)-CH2CH2-COOH) | Ki = 68 nM |

TABLE III(c)-continued in vitro Activity of NAALADase Inhibitors

| Compound | Ki Value (nM) |
|---|---|
| 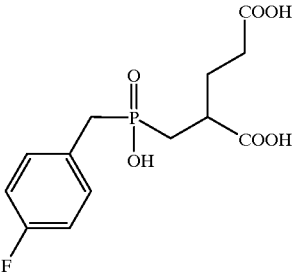 | Ki = 70 nM |
| 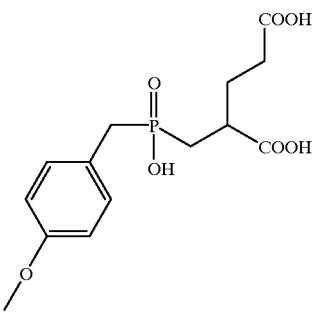 | Ki = 90 nM |
| 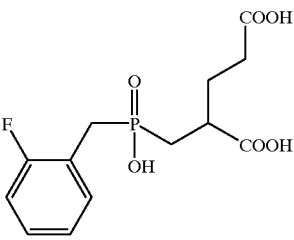 | Ki = 175 nM |
| 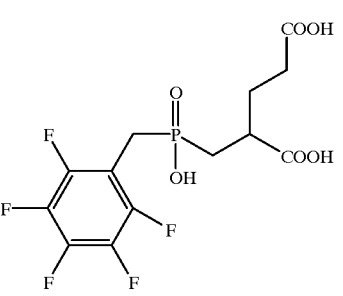 | Ki = 38 nM |

Protocol for In Vitro Assay of NAALADase Activity

The amount of [$^3$H]Glu liberated from [$^3$H]NAAG in 50 mM Tris-Cl buffer was measured for 15 minutes at 37° C. using 30–50 μg of synaptosomal protein. Substrate and product were resolved by anion-exchange liquid chromatography. Duplicate assays were performed so that no more than 20% of the NAAG was digested, representing the linear range of peptidase activity. Quisqualate (100 μM) was included in parallel assay tubes to confirm the specificity of the measurements.

In Vitro Assay of NAALADase Inhibitors on Cancer

Figure 2:
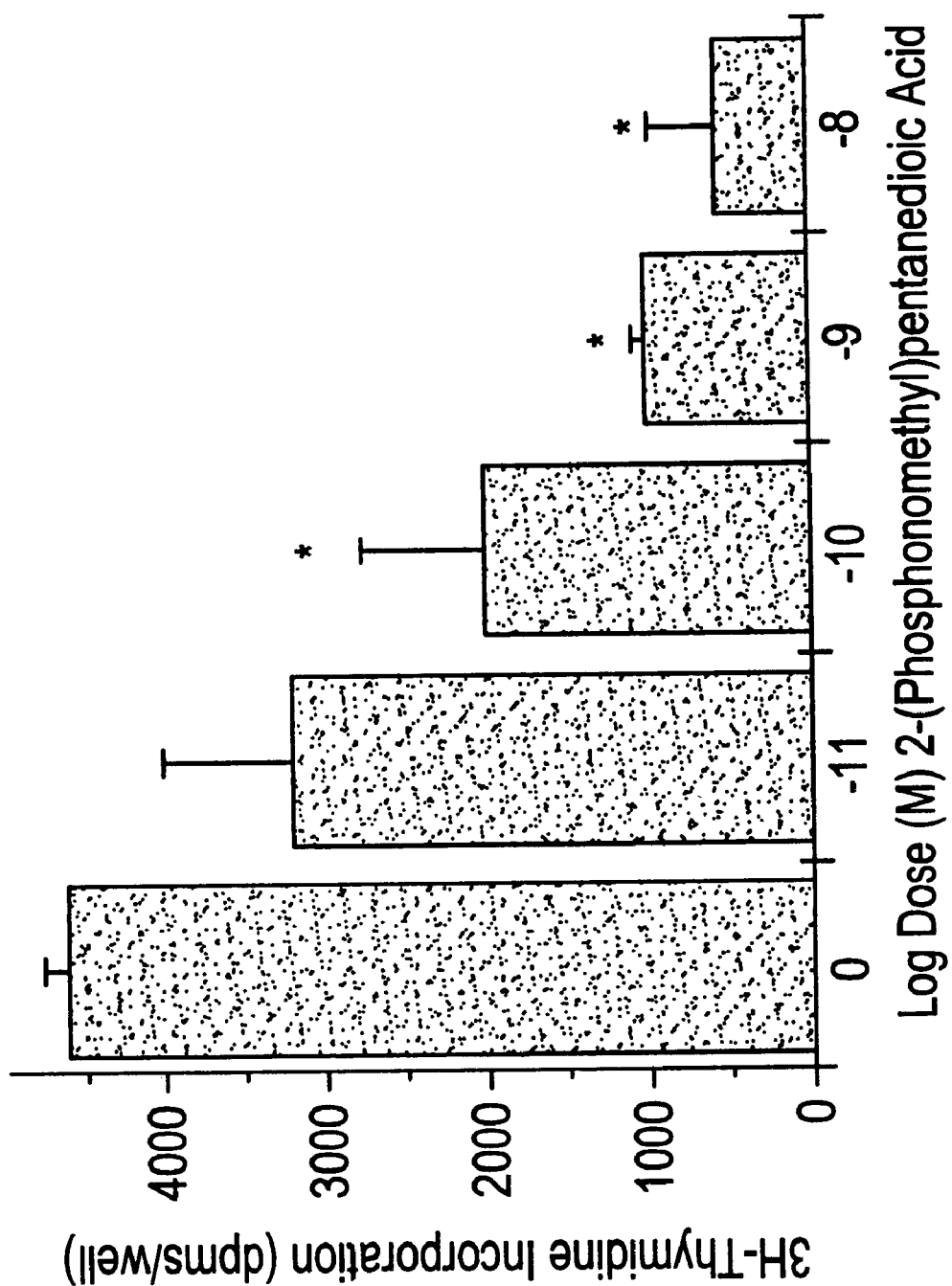
FIG. 2 is a bar graph plotting the growth of the prostate cancer cell line, LNCAP, against various concentrations of 2-(phosphonomethyl)pentanedioic acid, a NAALADase Inhibitor.

Referring now to FIGS. 1 and 2, the effect of NAALA-Dase inhibitors on cancer cell line were examined. LNCAP cells (a prostate cancer cell line) were treated with quisqualate acid (in concentrations ranging from 10 nM to 1 μM) and 2-(phosphonomethyl)pentanedioic acid (in concentrations ranging from 100 pM to 10 nM). The 3H-thymidine measurement for each concentration of quisqualate acid and 2-(phosphonomethyl)pentanedioic acid is also provided in TABLE IV below. FIGS. 1 and 2 present this data graphically and particularly illustrate the decrease in proliferation and thymidine uptake of cells treated with NAALADase inhibitors.

TABLE IV

| | 3H-Thymidine Incorporation (dpm/well) | |
|---|---|---|
| Dose | Quisqualic Acid | 2-(phosphonomethyl)-pentanedioic acid |
| Control | 4813 ± 572 | 4299 ± 887 |
| 10 pM | — | 3078 ± 1006 |
| 100 pM | — | 2062 ± 595 |
| 1 nM | 3668 ± 866 | 1001 ± 52 |
| 10 nM | 2137 ± 764 | 664 ± 366 |
| 100 nM | 1543 ± 312 | — |
| 1 μM | 1295 ± 181 | — |

The results show that LNCAP cell proliferation (as measured by the incorporation of 3H-thymidine) decreased significantly as the concentration of the NAALADase inhibitors increased, suggesting that the compounds of the present invention would be effective in treating cancer, particularly prostate cancer.

Protocol for In Vitro Cancer Assay

Cells in RPMI 1640 medium containing 10% Fetal Calf Serum (FCS) are plated in 24 well plates and allowed to adhere for 24 hours before addition of quisqualic acid ($10^{-9}$ M to $10^{-6}$ M) or 2-(phosphonomethyl)pentanedioic acid ($10^{-11}$ M to $10^{-8}$ M) for 7 days. On the 7th day, the cells are pulsed with 3H-thymidine for 4 hours, harvested and measured for radioactivity. Values represent means +/−SEM of 6 separate cell wells for each treatment. All experiments are performed at least twice.

To control for non-specific cytostatic effects of quisqualate acid and 2-(phosphonomethyl)pentanedioic acid, the agents are simultaneously evaluated on a non-NAALADase containing prostate cell line, DU145 (Carter et al., Proc. Natl. Acad. Sci. USA, (93) 749–753, 1996). If the treatments with quisqualate acid and 2-(phosphonomethyl) pentanedioic have no significant effect on cell growth, the NAALADase inhibiting activity of the agents are uniquely responsible for their cytostatic effects on NAALADase containing prostate carcinoma cell lines.

Cell Lines and Tissue Culture

LNCAP cells are obtained from Dr. William Nelson at the Johns Hopkins School of Medicine in Baltimore, Md. DU145 cells are obtained from American Type Culture Collection (Rockville, Md.). Cells are grown in RPMI-1640 media supplemented with 10% heat-inactivated fetal calf serum, 2 mM-glutamine, 100 units/ml penicillin, and 100 μg/ml streptomycin (Paragon) in a humidified incubator at 37° C. in a 5% $CO_2$/95% $O_2$ atmosphere.

[3H] Thymidine Incorporation Assays

The cells are suspended at 1×10$^3$ cells/ml in RPMI-1640 media and seeded into 24-well plates at 500 μl per well. After 24 hours, various concentrations of quisqualic acid (Sigma) or the potent NAALADase inhibitor 2-(phosphonomethyl)pentanedioic acid (synthesized according to the methods of Jackson et al., J Med Chem 39(2) 619–622) is added to the wells and the plates are returned to the incubator. On days 3, 5 and 7, media and drug are refreshed. On the 8th day following seeding, each well is pulsed with 1 $\mu$Ci $^3$H-thymidine (New England Nuclear) for 4 hours. Media is then removed and the wells washed 2 times with phosphate buffered saline (pH=7.4). The contents of each well is subsequently solubilized with 250 $\mu$l of 0.2 N NaOH and transferred to scintillation vials. 5 ml Ultima-Gold (Packard) scintillation cocktail is added and radioactivity is quantitated using a Beckman LS6001 scintillation counter.

The purity and/or identity of all synthetic compounds is ascertained by thin layer chromatography, High Pressure Liquid Chromatography (HPLC), mass spectrometry, and elemental analysis. Proton Nuclear Magnetic Resonance (NMR) spectra are obtained using a Bruker spectrometer. Chemical shifts are reported in parts per million relative to tetramethylsilane as internal standard. Analytical thin-layer chromatography (TLC) is conducted on prelayered silica gel GHLF plates (Analtech, Newark, Del.). Visualization of the plates is accomplished by using UV light, phosphomolybdic acid-ethanol, and/or iodoplatinate charring. Flash chromatography is conducted on Kieselgel 60, 230–400 mesh (E. Merck, Darmstadt, West Germany). Solvents are either reagent or HPLC grade. Reactions are run at ambient temperature and under a nitrogen atmosphere unless otherwise noted. Solutions are evaporated under reduced pressure on a Buchi rotary evaporator.

In vivo LNCaP Tumor Xenograft Assay and Results

Figure 3:
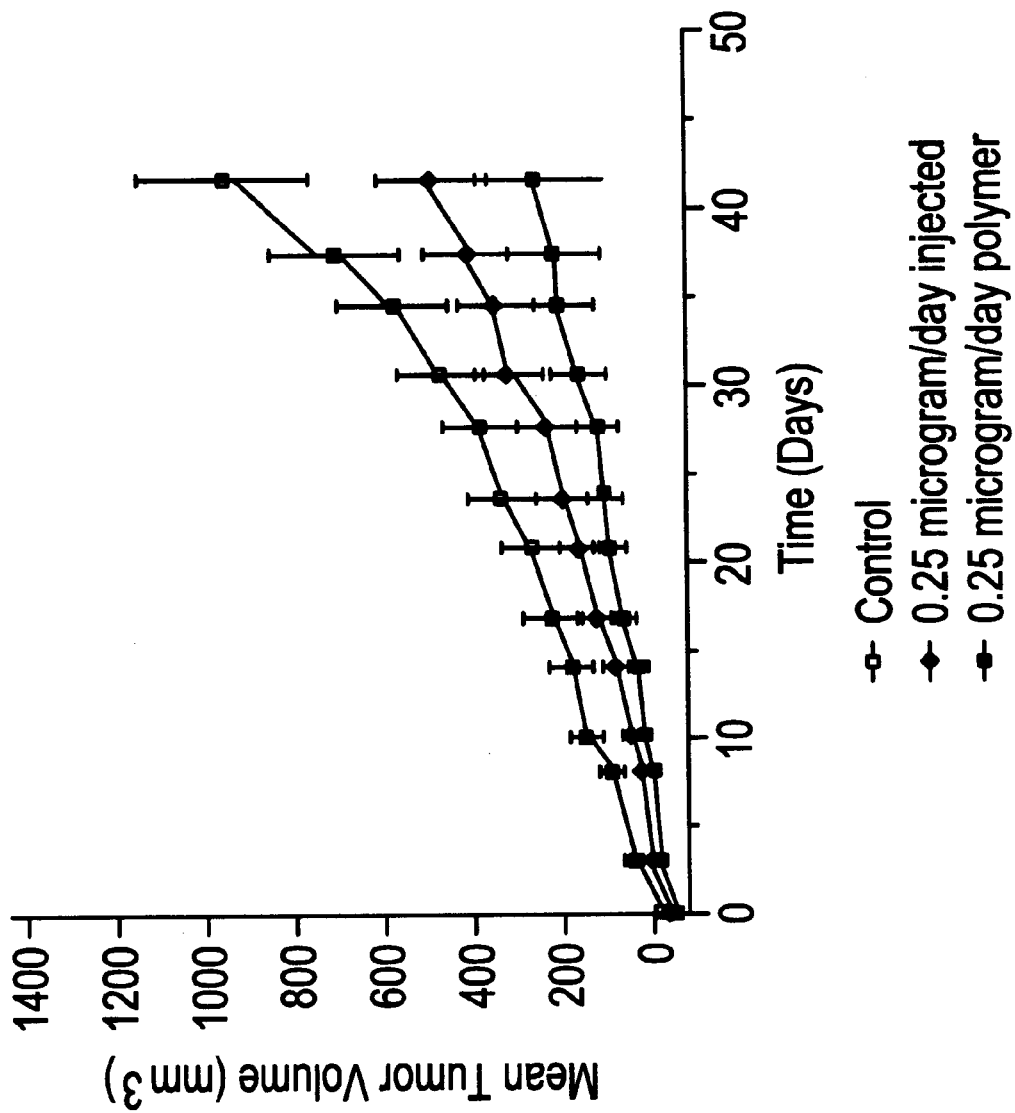
FIG. 3 is a line graph of the response of LNCAP human prostate tumors to daily treatment with 2-(phosphonomethyl)pentanedioic acid. Mean of individual tumor volumes are plotted as a function of time after the start of treatment. Error bars represent the SEM. Treatment with 2-(phosphonomethyl)pentanedioic acid for six weeks resulted in statistically significant difference between both the control group and animals given daily injections of drug (p=0.04), and the control group and animals implanted with polymer (p=0.02).
Figure 4:
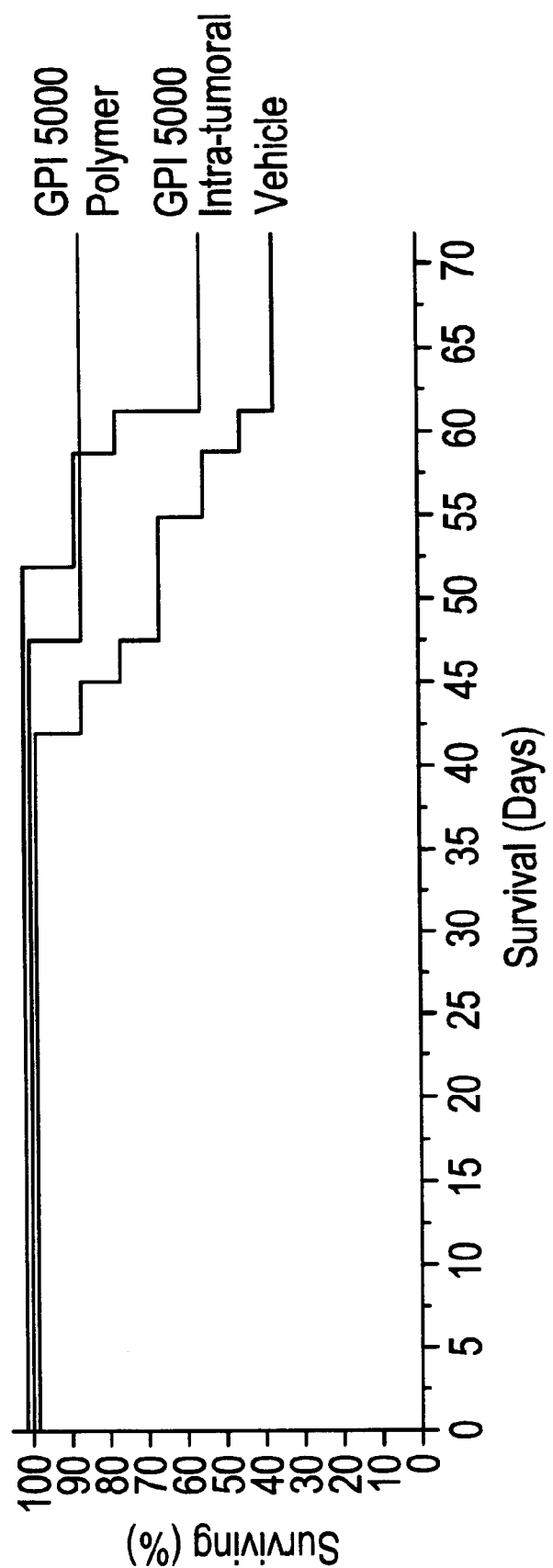
FIG. 4 is a line graphs plotting the survival percentage of animals treated with injections against the number of days.

Referring now to FIGS. 3 and 4, LNCaP human prostate cancer cells were injected subcutaneously into the right flank of male nude mice. 2-(phosphonomethyl)pentanedioic acid, a NAALADase inhibitor, was administered by daily intratumoral injection (0.25 $\mu$g/day)beginning when the tumors reached a volume of approximately 50–70 mm$^3$. An additional group was included using a silicon polymer containing 2-(phosphonomethyl)pentanedioic acid which released approximately 0.25 $\mu$g/day of drug locally into the tumor. The 2-(phosphonomethyl)pentanedioic acid polymer was changed two times per week. Tumor volumes were monitored for 42 days after the beginning of treatment.

EXPERIMENTAL PROCEDURES
Cell Lines

LNCaP is a human prostate cancer cell line that was established in 1973 from a pleural effusion of a patient who had been treated with 5-FU, doxorubicin, methotrexate, and CTX in the 3 months before the cell line was initiated. This line is androgen receptor positive and has been used in screening anticancer drugs that are targeted as hormone antagonists. LNCaP was grown in RPMI with 1.5 g NaHCO3/L, 10% fetal bovine serum (FBS), and 2 mM L-glutamine and was kept at 37° C. in a humidified 5% $CO_2/O_2$ incubator. Antibiotics were not added to the medium.

Animal Tumor Model

NCr nude (nu/nu)male mice, age 4–5 weeks, were purchased from Taconic (Germantown, N.Y.). The animals were housed four per cage in sterile filter-topped cages in a ventilated cage rack. Upon arrival, they were quarantined for four working days before use. Temperature was maintained at 72±5° F. and relative humidity at 35–70%, and a 12-hr light/dark cycle is used. The mice were fed sterile, autoclavable, certified Purina rodent chow ad libitum. Drinking water was acidified and autoclaved, and the source water was recirculated, deionized, UV-treated, and 5-$\mu$m filtered.

After the animals were released from quarantine, the mice were injected subcutaneously in the right flank with 1×10$^7$ LNCaP cells in Matrigel™ (0.1-ml injection volume) Tumor dimensions and body weight were measured twice weekly. Vernier calipers were used to measure tumors in three planes, and tumor volume (V) was calculated as follows: $V=\pi(x \times y \times z)/6$, where x, y, and z were the tumor measurements minus skin thickness. At the end of the experiment, the mice were sacrificed by $CO_2$ inhalation followed by cervical dislocation.

Pharmaceuticals 2-(phosphonomethyl)pentanedioic acid was made up in water at a concentration of 2.5 mg/ml. Polymer containing 2-(phosphonomethyl)pentanedioic acid was made up by grinding 140 mg NaCl to a fine powder then mixing with 5 mg 2-(phosphonomethyl)pentanedioic acid and 350 mg silicone gel. The mixture was spread to a thin film and allowed to dry for 24 hours. The material was cut into 1–1.5 mg pieces for subcutaneous implantation.

Treatment Protocol

When the tumor volumes reached a predetermined size (mean tumor volume 50–70 mm$^3$), mice were added randomly into treatment groups of six to eight mice each. All treatments were administered daily for at least 4 weeks. 2-(phosphonomethyl)pentanedioic acid was administered intratumorally daily in a volume of 0.05 ml containing 0.025 $\mu$g 2-(phosphonomethyl)pentanedioic acid per injection.

Polymer containing 2-(phosphonomethyl)pentanedioic acid (10 $\mu$g drug/mg polymer) was implanted subcutaneously. Mice were anaesthetized with metafane, and a small (<2 mm) incision was made near the tumor site. Following implantation, the incision was closed with a wound clip. Polymer was replaced twice weekly.

The tumor were measured twice weekly for at least 8 weeks after the first treatment. The mean tumor volume for each group was calculated for each time point. Comparisons between groups at specific times were made using an unpaired, two-tailed t-test, and the results were analyzed using analysis of variance (ANOVA).

Systemic toxicity was assessed from reductions in body weight after treatment. The mice were sacrificed at the end of the follow-up period, or earlier if their tumor volumes reached 1600 mm$^3$ or the tumors ulcerated.

Statistical Analysis

Statistical analysis as described above was performed using JMP (SAS Institute Inc., Cary, N.C.)

In vivo Rat Dunning R3327 Model

Figure 5:
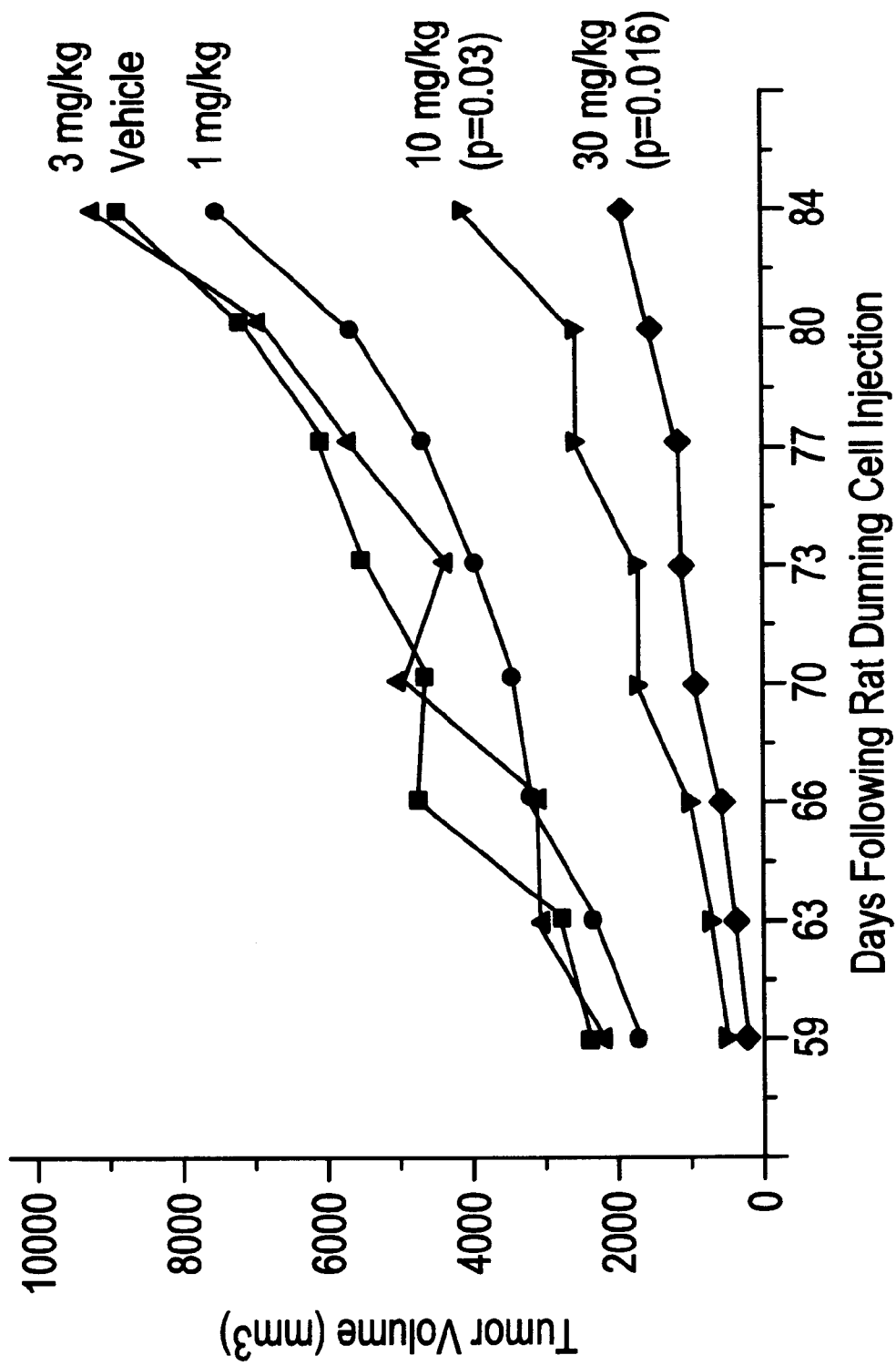
FIG. 5 is a line graph plotting tumor growth against days following rat dunning cell injections. Cells were injected, over a period of 84 days, with various dosages of 2-(phosphonomethyl)pentanedioic acid and a control vehicle.
Figure 6:
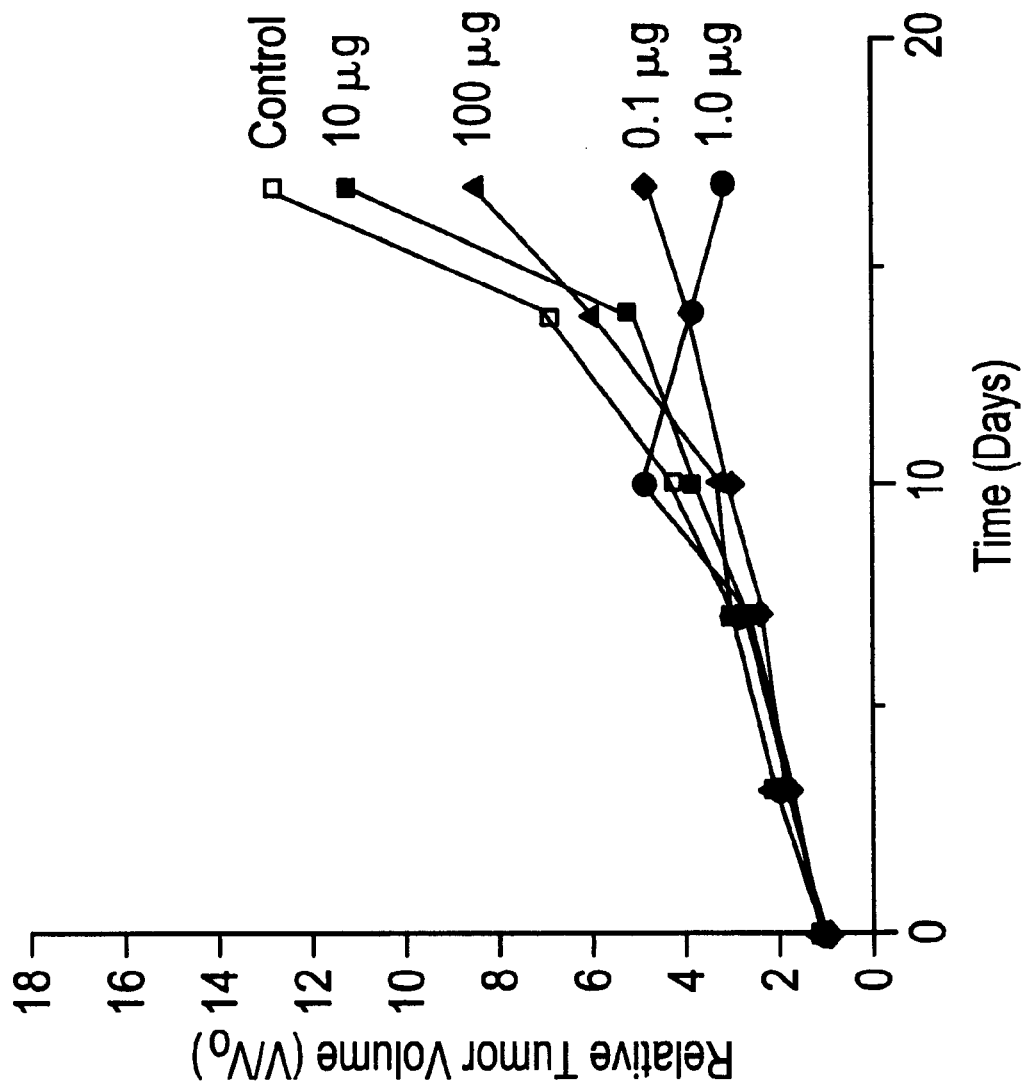
FIG. 6 is a line graph of the response of R3327 rat prostate tumors to daily treatment with 2-[[(phenylmethyl) hydroxyphosphinyl]methyl]pentanedioic acid. Mean of individual tumor volumes expressed relative to the volume at the start of treatment (V/V$_o$) are plotted as a function of time: Treatment with 2-[[(phenylmethyl) hydroxyphosphinyl]methyl]pentanedioic acid for 2.5 weeks resulted in a statistically significant difference between the control group and animals given daily injections of 1 μg of drug (p=0.02).

Referring now to FIGS. 5 and 6, Dunning R3327-G prostate cancer cells were injected subcutaneously into both flanks of syngeneic male rats. In the first study, the anti-tumor growth activity of 2-(phosphonomethyl)pentanedioic acid was tested following daily subcutaneous injections of the drug (1, 3 10 and 30 mg/kg). 2-(phosphonomethyl) pentanedioic acid injections and tumor measurements were continued for 12 weeks. In the second study, the anti-tumor growth activity of 2-[[phenylmethyl)hydroxyphosphinyl] methyl]pentanedioic acid was tested following daily intratumoral injections of the drug (0.1,1,10,100 $\mu$g) after the tumor reached an initial volume of 80–290 mm$^3$. Tumor volumes were subsequently monitored for 42 days after the beginning of drug treatment.

EXPERIMENTAL PROCEDURES

Cell Lines

R3327-G is a cell line derived from an androgen-sensitive papillary adenocarcinoma derived from a spontaneously forming tumor in the rat prostate. R3327-G cells were grown in RPMI, lot fetal bovine serum (FBS), 2 mM L-glutamine, and 10–8 M dexamethasone. Cultures were kept at 37° C. in a humidified 5% $CO_2/O_2$ incubator. Antibiotics were not added to the medium.

Animal Tumor Model

Copenhagen male rats, age 8–10 weeks, were purchased from Harlan Sprague Dawley (Indianapolis, Ind.). The animals were housed two per cage. Upon arrival, they were quarantined for four working days before use. Temperature was maintained at 72±5° F. and relative humidity at 35–70%, and a 12-hr light/dark cycle was used. The rats were fed certified Purina rodent chow and water ad libitum.

After the animals were released from quarantine, the rats were injected subcutaneously in both flanks with $1 \times 10^7$ R3327-G cells (0.1-ml injection volume). Tumor dimensions and body weight were measured twice weekly. Vernier calipers were used to measure tumors in three planes, and tumor volume (V) was calculated as follows: $V=\pi(x \times y \times z)/6$, where x, y, and z were the tumor measurements minus skin thickness. Tumors began to appear 4–5 weeks after tumor cell injection. At the end of the experiment, the rats were sacrificed by $CO_2$ inhalation.

Pharmaceuticals 2-(phosphonomethyl)pentanedioic acid was made up in physiological saline fresh each day prior to injection. A stock solution of 2-[[phenylmethyl)hydroxyphosphinyl]methyl] pentanedioic acid was made up in water at a concentration 2.5 mg/ml; ten-fold serial dilutions were made fresh weekly for injections.

Treatment Protocol

In the 2-(phosphonomethyl)pentanedioic acid study, the rats were given daily subcutaneous injections of drug beginning the 14 days following tumor cell implantation and continued for 12 weeks. In the 2-[[phenylmethyl) hydroxyphosphinyl]methyl]pentanedioic acid study, the drug was not administered until the tumor volumes reached a predetermined size (mean tumor volume 90–290 mm³). At this time, the rats were divided into treatment groups of five rats each. All treatments of 2-[[phenylmethyl) hydroxyphosphinyl]methyl]pentanedioic acid were subsequently administered Intra-tumorally daily for 6 weeks.

The tumors were measured twice weekly. The mean tumor volume for each group was calculated for each time point. Comparisons between groups at specific times were made using an unpaired, two-tailed t-test, and the results were analyzed using analyzed of variance (ANOVA). For the 2-[[phenylmethyl)hydroxyphosphinyl]methyl] pentanedioic acid study, individual tumor volumes (.V) were expressed as a fraction of the tumor volume on Day 0, the first day of treatment (V0). For each group, the mean of the ratio V/V0 was plotted as a function of time after treatment.

Statistical Analysis

Statistical analysis as described above was performed using JMP (SAS Institute, Inc. Cary, N.C.).

EXAMPLES

The following examples are illustrative of preferred embodiments of methods of use and preparation of compounds of the invention and are not to be construed as limiting the invention thereto. Unless otherwise indicated, all percentages are based upon 100% of the final formulations.

Example 1

Preparation of 2-[(methylhydroxyphosphinyl)methyl]pentanedioic acid

Scheme IV R=CH3, R1=CH2Ph

Methyl-O-benzylphosphinic Acid

Dichloromethylphosphite (10.0 g, 77 mmol) in 80 mL of dry diethyl ether was cooled to –20° C. under an atmosphere of nitrogen. A solution of benzyl alcohol (23 g, 213 mmol) and triethylamine (10.2 g, 100 mmol) in 40 mL of diethyl ether was added dropwise over 1 hour while maintaining an internal temperature range of 0° C. to 10° C. Once addition was complete the mixture was warmed to room temperature and stirred overnight. The mixture was filtered and the solid cake washed with 200 mL of diethyl ether. The organics were combined and evaporated under reduced pressure to give 25 g of a clear and colorless liquid. The liquid was purified by flash chromatography and eluted with a 1:1 hexane/ethyl acetate to ethyl acetate gradient. The desired fractions were collected and evaporated to give methyl O-benzylphosphinic acid (1, R=CH3, R1=CH2Ph, 6.5 g, 50%) as a clear and colorless oil. Rf 0.1 (1:1, Hexane/EtOAc).

$^1$H NMR (d6-DMSO): 7.4 ppm (m, 5H), 7.1 ppm (d, 1H), 5.0 ppm (dd, 2H), 1.5 ppm (d, 3H).

2,4-Di(benzyloxycarbonyl)butyl(methyl)-O-benzylohosphinic acid

Methyl-O-benzylphosphinic acid (3.53 g, 20.7 mmol) in 200 mL of dichloromethane was cooled to –5° C. under an atmosphere of nitrogen. Triethylamine (3.2 g, 32 mmol) was added via syringe followed by trimethylsilyl chloride (2.9 g, 27 mmol). The reaction mixture was stirred and warmed to room temperature over 1 hour. Dibenzyl 2-methylenepentanedicate (2, 6.0 g, 18.5 mmol) in 10 mL of dichloromethane was added. The mixture was then stirred at room temperature overnight. The reaction mixture was cooled to 0° C. and trimethylaluminum (9 mL, 18 mmol, 2.0 M in dichloromethane) was added. The flask was warmed and stirred for 72 hours. The clear light yellow solution was cooled to 5° C. and quenched by the slow addition of 5% hydrochloric acid. The quenched reaction mixture was warmed to room temperature and the organic layer removed. The organic layer was washed with 5% hydrochloric acid and with water. The organics were dried ($MgSO_4$) and evaporated under reduced pressure to give 8 g of a clear light yellow oil. The oil was purified on silica gel and eluted with a gradient of 1:1 hexanes/ethyl acetate to 100% ethyl acetate. The desired fractions were collected and evaporated to give 2,4-di(benzyloxycarbonyl)buty(methyl)-O-benzylphosphinic acid (3, R=CH3, R1=CH2Ph 0.8 g, 8%) as a clear and colorless oil. Rf 0.5 (ethyl acetate).

$^1$H NMR (CDCl$_3$): 7.4 ppm (m, 15H), 5.1 ppm (m, 6H), 3.0 ppm (m, 1H), 2.4 ppm (m, 3H), 2.1 ppm (m, 3H), 1.5 ppm (dd, 3H); Elemental Analysis Calculated $C_{28}H_{31}O_6P.0.5H_2O$: C, 68.01, H, 6.32 Found: C, 66.85, H, 6.35.

2-[(Methylhydroxyphosphinyl)methyl]pentanedioic acid 2,4-di(benzyloxycarbonyl)buty(methyl)-O-benzylphosphinic acid (0.8 g, 1.6 mmol) in 20 mL of water containing 100 mg of 10% Pd/C was hydrogenated at 40 psi for 4 hours. The mixture was filtered over a pad of Celite and evaporated at high vacuum to give 2-[(methylhydroxyphosphinyl)methyl]pentanedioic acid (4, R=CH3, 0.28 g, 78% as a clear and colorless viscous oil.

$^1$H NMR (D$_2$O): 2.5 ppm (m, 1H), 2.2 ppm (t, 2H), 2.0 ppm (m, 1H), 1.7 ppm (m, 3H), 1.3 ppm (d, 3H). Elemental-Analysis Calculated $C_7H_{13}O_6P.0.2\ H_2O$: C, 36.92 H, 5.93 Found: C, 37.06 H, 6.31.

Example 2

Preparation of 2-[(butylhydroxyphosphinyl)methyl]pentanedioic acid

Scheme IV R=n-butyl, R1=H

Butylphosphinic Acid

Diethyl chlorophosphite (25 g, 0.16 mol) in 60 mL of dry ether was cooled to 0° C. under an atmosphere of nitrogen. Butylmagnesium chloride (80 mL, 0.16 mol, 2.0 M solution in ether) was added dropwise over a period of 2 hours while maintaining the internal temperature at 0° C. Once addition was complete the thick white slurry was heated to 30° C. for 1 hour. The suspension was filtered under a nitrogen atmosphere and the filtrate evaporated under reduced pressure. The clear light yellow liquid was then brought up in 15 mL of water and stirred at room temperature. Concentrated hydrochloric acid (0.5 mL) was then added and an exothermic reaction was observed. The mixture was stirred an additional 15 minutes and extracted with two 75 mL portions of ethyl acetate. The organics were combined, dried ($MgSO_4$) and evaporated to give a clear and colorless liquid. The liquid was treated with NaOH (40 mL, 20 M) and stirred for 1 hour. The mixture was then washed with diethyl ether and acidified to pH 1.0. The desired material was extracted from the acidified extract with two 100 mL portions of ethyl acetate. The organics were combined, dried ($MgSO_4$) and evaporated under reduced pressure to give butylphosphinic acid (1, R=n-butyl, R1=H, 10 g, 51%) as a clear and colorless liquid.

$^1$H NMR (d6-DMSO): 6.9 ppm (d, 1H), 1.6 ppm (m, 2H), 1.4 ppm (m, 4H), 0.9 ppm (t, 3H).

Butyl[2,4-di(benzyloxycarbonyl)butyl]phosphinic acid

Butylphosphinic acid (2.0 g, 16 mmol) in 80 mL of dry dichloromethane was cooled to 0° C. under an atmosphere of nitrogen. Triethylamine (6.7 g, 66 mmol) was added followed by trimethylsilyl chloride (58 mL, 58 mmol, 1.0 M in dichloromethane). The mixture was stirred at 0° C. for 10 minutes and dibenzyl 2-methylenepentanedioate (2)(6.4 g, 20 mmol) in 20 mL of dichloromethane was added. The cold bath was removed and the reaction warmed to room temperature and stirred overnight. The mixture was then cooled to 0° C. and quenched by the slow addition of 5% hydrochloric acid. The dichloromethane layer was then removed and washed with 5% hydrochloric acid and with brine. The organic layer was dried ($MgSO_4$) and evaporated to give a clear light golden liquid. The liquid was purified by flash chromatography and eluted with 3:1 hexane/ethyl acetate containing 5% acetic acid. The desired fractions were combined and evaporated to give butyl[2,4-di(benzyloxycarbonyl)butyl]phosphinic acid (3, R=n-butyl, R1=H) (2.9 g, 40%) as a clear and colorless oil. Rf 0.12 (3:1, Hex./EtOAc 5% AcOH).

$^1$H NMR (d6-DMSO): 7.3 ppm (m, 10), 5.0 ppm (s, 4H), 2.7 ppm (m, 1H), 2.3 ppm (y, 2H), 1.8 ppm (m, 2H), 1.3 ppm (m, 4H), 0.8 ppm (t, 3H).

2-[(Butylhydroxyphosphinyl)methyl]pentanedioic acid

Butyl[2,4-di(benzyloxycarbonyl)butyl]phosphinic acid (2.9 g, 6.5 mmol) in 30 mL of water containing 0.32 g 10% Pd/C was hydrogenated on a Parr hydrogenator at 40 psi for 4.5 hours. The mixture was filtered through a pad of Celite and evaporated under high vacuum to give 2-[(butylhydroxyphosphinyl)methyl]pentanedioic acid (4, R=n-butyl) (0.75 g, 43w) as a clear and colorless viscous oil.

$^1$H NMR ($D_2O$): 2.4 ppm (m, 1H), 2.1 ppm (t, 2H), 1.9 ppm (m, 1H), 1.6 ppm (m, 3H), 1.4 ppm (m, 2H), 1.1 ppm (m, 4H), 0.6 ppm (t, 3H); Elemental Analysis Calculated $C_{10}H_{19}O.P.0.5\ H_2O$: C, 43.64, H, 7.32: Found C, 43.25, H, 7.12.

Example 3

Preparation of 2-[(benzylhydroxyphosphinyl)methyl]pentanedioic acid

Scheme IV R=CH2Ph, R1=H

Benzylphosphinic Acid

Diethylchlorophosphite (25 g, 0.16 mol) in 100 mL of dry diethyl ether was cooled to 0° C. under an atmosphere of nitrogen. Benzylmagnesium chloride (80 mL, 0.16 mol, 2.0 M solution in $Et_2O$) was added dropwise over two hours while maintaining a temperature below 10° C. A thick white slurry formed and stirring was continued at room temperature for 1 hour. The mixture was filtered under a nitrogen atmosphere and the filtrate evaporated under reduced pressure to give a clear and colorless liquid. The liquid was stirred as 15 mL of water was added followed by 0.5 ml concentrated hydrochloric acid. An exothermic reaction was observed and stirring was continued for an additional 30 minutes followed by extraction with ethyl acetate. The organics were combined, washed with brine, dried ($MgSO_4$) and evaporated. The clear light golden liquid was added to sodium hydroxide (50 mL, 2.0 M NaOH), stirred for one hour and washed with diethyl ether. The aqueous layer was acidified to pH 1.0 with concentrated hydrochloric acid and extracted with ethyl acetate. The organics were combined, dried ($MgSO_4$) and evaporated to give benzylphosphinic acid (1, R=CH2Ph, R1+H) (8 g, 32%) as a clear light golden oil.

$^1$H NMR (d6-DMSO): 7.3 ppm (m, 5H), 6.9 ppm (d, 1H), 3.1 ppm (d, 2H).

Benzyl[2,4-di(benzyloxycarbonyl)butyl]phosphinic acid

Benzylphosphinic acid (2.3 g, 15 mmol) in 150 mL of dry dichloromethane was cooled to 0° C. under a nitrogen atmosphere. Triethylamine (6.5 g, 65 mmol) was added followed by trimethylsilyl chloride (5.8 g, 54 mmol) while the reaction temperature was maintained at 0° C. After 30 minutes dibenzyl 2-methylenepentanediote (2) in 20 mL of dichloromethane was added over 5 minutes. The reaction mixture was left to warm to room temperature and stirred overnight. The clear solution was cooled to 0° C. and quenched with 5% hydrochloric acid and with brine, dried ($MgSO_4$) and evaporated to give a clear yellow liquid. Purification by flash chromatography and elution with 1:1 hexane/ethyl acetate containing 10% acetic acid yielded 2.0 g (28%) of benzyl[2,4-di(benzyloxycarbonyl)butyl]phosphinic acid (3, R=CH2Ph, $R_1$+H) as a clear light yellow oil. Rf 0.37 (1:1 Hex./EtOAc, 10% AcOH).

$^1$H NMR (d6-DMSO): 7.2 ppm (m, 15H), 5.0 ppm (s, 4H), 3.0 (d, 2H), 2.8 ppm (m, 1H), 2.3 ppm (t, 2H), 1.9 ppm (m, 2H), 1.7 ppm (t, 1H).

2-[(Benzylhydroxyphosphinyl)methyl]pentanedioic acid

Benzyl[2,4-di(benzyloxcarbonyl)butyl]phosphinic acid (0.5 g, 1.0 mmol) in 20 mL of water containing 120 mg of 10% Pd/C was hydrogenated on a Parr hydrogenator at 40 psi for 6 hours. Filtration through a Celite pad followed by evaporation on high vacuum gave 0.17 g (57%) of 2-[(benzylhydroxyphosphinyl)methyl]pentanedioic acid (4, R=CH2Ph) as a white solid.

$^1$H NMR ($D_2O$): 7.1 ppm (m, 5H), 2.9 ppm (d, 2H), 2.4 ppm (m, 1H), 2.1 ppm (t, 2H), 1.8 ppm (m, 1H), 1.6 ppm (m, 3H); Elemental Analysis, Calculated $C_{13}H_{17}O_6P$: C, 52.00 H, 5.71: Found: C, 51.48 H, 5.70.

Example 4

Preparation of 2-[(phenylethylhydroxyphosphinyl)methyl]pentanedioic acid

Scheme IV R=CH2CH2Ph, R1=H

Phenethylphosphinic Acid

Diethylchlorophosphite (15.6 g, 0.1 mol) in 100 mL of dry diethyl ether was cooled to 50° C. under an atmosphere of nitrogen. Phenethylmagnesium chloride (100 mL, 0.1 mol, 1.0 M in THF) was added dropwise over 2 hours while maintaining a temperature between 0–10° C. A thick white slurry formed and stirred at room temperature overnight. The mixture was filtered under a nitrogen atmosphere and the filtrate evaporated under reduced pressure to give a clear and colorless liquid. The liquid was stirred as 15 mL of water was added followed by 0.5 mL of concentrated hydrochloric acid. An exothermic reaction was observed and stirring continued for 15 minutes followed by extraction with ethyl acetate. The organics were combined, washed with brine, dried ($MgSO_4$) and evaporated. The clear liquid was brought up in sodium hydroxide (40 mL, 2.0 M NaOH), stirred for 1 hour and washed once with diethyl ether. The aqueous layer was acidified to pH 1.0 with concentrated hydrochloric acid and extracted with ethyl acetate. The organics were combined, dried ($MgSO_4$) and evaporated to give phenethylphosphinic acid (1, R=CH2CH2Ph, R1=H) (9.8 g, 58%) as a clear light yellow oil.

$^1$H NMR (d6-DMSO): 7.2 ppm (m, 5H), 6.9 ppm (d, 1H), 2.8 ppm (m, 2H), 1.9 ppm (m, 2H).

2,4-Di(benzyloxycarbonyl)butyl(phenethyl)phosphinic acid

Phenethylphosphinic acid (1.0 g, 5.9 mmol) in 50 mL of dry dichloromethane was cooled to −5° C. under a nitrogen atmosphere. Triethylamine (2.3 g, 23 mmol) was added followed by trimethylsilyl chloride 2.2 g, 21 mmol) while the reaction temperature was maintained at 0° C. After 10 minutes dibenzyl 2-methylenepentanedioate (2) in 10 mL of dichloromethane was added over 10 minutes. The reaction mixture was left to warm to room temperature and stirred overnight. The clear solution was cooled to 0° C. and quenched with 5% hydrochloric acid followed by removal of the organic layer. The organic layer was washed with brine, dried (MgSO4) and evaporated to give a clear light golden liquid. Purification by flash chromatography and elution with 1:1 Hexane/EtOAc containing 5% AcOH resulted in 1.2 g (41%) of 2,4-di(benzyloxycarbonyl)butyl(phenethyl) phosphinic acid (3, R=CH2CH2Ph, R1=H) as a clear and colorless oil.

$^1$H NMR (d6-DMSO): 7.2 ppm (m, 15H), 5.0 ppm (s, 4H), 3.3 ppm (m, 1H), 2.8 ppm (m, 4H), 2.3 ppm (m, 2), 1.8 ppm (m, 4H).

2,4-[(Phenethylhydroxyphosphinyl)methyl]pentanedioic acid 2,4-Di(benzyloxycarbonyl)butyl(phenethyl)phosphinic acid (1.1 g, 2.2 mmol) in 20 mL of water containing 120 mg of 10% Pd/C was hydrogenated on a Parr hydrogenator at 40 psi overnight. Filtration through a Celite pad followed by evaporation on high vacuum gave 0.8 g (114%) of 2-[(phenethylhydroxyphosphinyl)methyl]pentanedioic acid (4, R=CH2CH2Ph) as a white solid.

$^1$H NMR ($D_2O$): 7.2 ppm (m, 5H), 2.7 ppm (m, 2H), 2.5 ppm (m, 1H), 2.3 ppm (t, 2H), 1.9 ppm (m, 6H), 1.5 ppm (t, 1H).

Elemental Analysis: Calculated $C_{14}H_{19}O_6P$ 0.75$H_2O$, 0.5 AcOH: C, 50.35 H, 6.34 Found: C, 50.26 H, 5.78.

Example 5

Preparation of 2-[(3-phenylpropylhydroxyphosphinyl) methyl]pentanedioic acid

Scheme IV R=CH2CH2CH2Ph, R1=H

3-Phenylproylphosphinic Acid

Magnesium turnings (2.44 g, 0.10 mol) in 20 mL of dry diethyl ether under an atmosphere of nitrogen was added several iodine crystals. Phenylpropyl bromide (20.0 g, 0.10 mol) in 80 mL of diethyl ether was placed in a dropping funnel. Approximately 10 mL of the bromide solution was added to the magnesium turnings and stirring was initiated. After several minutes the iodine was consumed and additional phenylpropyl bromide was added while maintaining a temperature of 35° C. Once additional was complete (1.5 hours) the mixture was sealed and stored at 5° C.

Diethylchlorophosphite (15.7 g, 0.1 mol) in 50 mL of dry diethyl ether was cooled to 5° C. under an atmosphere of nitrogen. Phenylpropylmagnesium bromide (100 mL, 0.1 mol, 1.0 M solution of in $Et_2O$) was added dropwise over 2 hours while maintaining a temperature between 0–10° C. A thick white slurry formed and was stirred an additional 30 minutes. The mixture was filtered under a nitrogen atmosphere and the filtrate evaporated under reduced pressure to give a clear and colorless liquid. To the liquid was added 20 mL of water followed by 0.5 ml of concentrated hydrochloric acid. An exothermic reaction was observed and stirring continued for 20 minutes followed by extraction with ethyl acetate. The organics were combined, washed with brine, dried ($MgSO_4$) and evaporated. To the clear liquid was added sodium hydroxide (40 mL, 2.0 M NaOH), the resulting solution stirred for 1 hour and then washed with diethyl ether. The aqueous layer was acidified to pH 1.0 with concentrated hydrochloric acid and extracted twice with ethyl acetate. The organics were combined, dried ($MgSO_4$) and evaporated to give 3-phenylpropylphosphinic acid (1, R=CH2CH2CH2Ph, R1=H) (9.8 g, 53%) as a clear and colorless oil.

$^1$H NMR (d6-DMSO): 7.2 ppm (m, 5H), 6.9 ppm (d, 1H), 2.6 ppm (t, 2H). 1.7 ppm (m, 2H), 1.6 ppm (m, 2H).

2,4-Di(benzyloxycarbonyl)butyl(3-phenylpropyl) phosphinic acid 3-phenylpropylphosphinic acid (1.0 g, 5.4 mmol) in 50 mL of dry dichloromethane was cooled to −5° C. under a nitrogen atmosphere. Triethylamine (2.2 g, 22 mmol) was added followed by trimethylsilyl chloride (2.1 g, 19 mmol) while the reaction temperature was maintained at 0° C. After 10 minutes dibenzyl 2-methylenepantanedioate (2) in 10 mL of dichloromethane was added over 10 minutes. The reaction mixture was warmed to room temperature and stirred overnight. The clear solution was cooled to 0° C. and quenched with 5% hydrochloric acid followed by removal of the organic layer. The organic layer was washed with brine, dried ($MgSO_4$) and evaporated to give a clear yellow liquid. Purification by flash chromatography and elution with 4:1-hexane/ethyl-acetate containing 5% acetic acid resulted in 1.5 g (56%) of 2,4-di(benzyloxycarbonyl)butyl(3-phenylpropyl)phosphinic acid (3, R=CH2CH2CH2Ph, R1=H) as a clear light yellow oil. Rf 0.58 (1:1 Hex./EtOAc, 5% AcOH);

$^1$H NMR (d6-DMSO): 7.2 ppm (m, 15H), 5.0 ppm (s, 4H), 2.7 ppm (m, 1H), 2.5 ppm (m, 5H), 2.2 ppm (m, 2H), 1.5 ppm (m, 3H), 1.6 ppm (m, 2H);

Elemental Analysis: Calculated $C_{29}H_{33}O_6P.1.3H_2O$: C, 65.48 H, 6.75 Found: C, 65.24 H, 6.39.

2-[(3-Phenylpropylhydroxyphosphinyl)methyl] pentanedioic acid 2,4-Di(benzyloxycarbonyl)butyl(3-phenylpropyliphosphinic acid (15) (1.4 g, 2.8 mmol) in 20 mL of water containing 150 mg of 10% Pd/C was hydrogenated on a Parr hydrogenator at 40 psi overnight. Filtration through a Celite pad followed by evaporation on high vacuum gave 0.8 g (89%) of 2-[(3-phenylpropylhydroxyphosphinyl)methyl]pentanedioic acid (4, R=CH2CH2CH2Ph) as a light yellow viscous oil).

$^1$H NMR (D2O): 7.4 ppm (m, 5H), 2.7 ppm (m, 3H), 2.4 ppm (t, 3H), 1.8 ppm (m, 7H);

Elemental Analysis: Calculated $C_{15}H_{21}O_6P$ 0.75 $H_2O$, 0.75 AcOH: C, 51.23 H, 6.64 Found: C, 50.85 H, 6.02.

Example 6
Preparation of 2-[(4-methylbenzyl)hydroxyphosphinyl] methyl]pentanedioic acid Scheme V, Compound 5

Hexamethyldisilazane (21.1 mL, 100 mmol) was added to vigorously stirred ammonium phosphinate (8.30 g, 100 mmol), and the resulting suspension was stirred at 105° C. for 2 h. A solution of 4-methylbenzyl bromide (5.00 g, 27.0 mmol) was then dropwise added to the suspension at 0° C. The mixture was stirred at rt for 19 h. The reaction mixture was then diluted with dichloromethane (50 mL) and washed with 1 N HCl (50 mL). The organic layer was separated, dried over $Na_2SO_4$, and concentrated to give 4.72 g of a white solid. This was dissolved in dichloromethane (50 mL) and benzyl alcohol (3.24 g, 30 mmol) was added to the solution. 1,3-Dicyclohexylcarbodiimide (DCC) (6.19 g, 30 mmol) was then added to the solution at 0° C., and the suspension was stirred at rt for 14 h. The solvent was removed under reduced pressure and the residue was suspended in EtOAc. The resulting suspension was filtered and the filtrate was concentrated. The residue was purified by silica gel chromatography (hexanes: EtOAc, 4:1 to 1:1) to give 2.40 g of 4-methylbenzyl-O-benzylphosphinic acid (2, R=4-methylbenzyl) as a white solid (34% yield): Rf 0.42 (EtOAc); $^1$H NMR (DMSO-$d_6$) delta 2.30 (s, 3H), 3.29 (d, J=16.6 Hz, 2H), 5.2 (m, 2H), 7.0 (d, J =543 Hz, 1H), 7.1–7.2 (m, 4H), 7.3–7.4 (m, 5H).

To a solution of 4-methylbenzyl-O-benzylphosphinic acid (2, R=4-methylbenzyl) (2.16 g, 8.3 mmol) in THF (15 mL) was added sodium hydride (0.10 g, 60% dispersion in oil) followed by dibenzyl 2-methylenepentanedioate at 0° C., and the mixture was stirred at rt for 4 h. The reaction mixture was then diluted with EtOAc (50 mL) and poured into 1N HCl (50 mL). The organic layer was separated, dried over $Na_2SO_4$, and concentrated. This material was purified by silica gel chromatography (hexanes: EtOAc, 4:1 to 1:1) to give 3.41 g of 2,4-di(benzyloxycarbonyl)butyl(4-methylbenzyl)-o-benzylphosphinic acid (4, R=4-methylbenzyl)as colorless oil (70% yield): Rf 0.61 (EtOAc); $^1$H NMR (CDCl$_3$) delta 1.6–1.8 (m, 1H), 1.9–2.0 (m, 2H), 2.1–2.4 (m, 6H), 2.7–2.9 (m, 1H), 3.05 (dd, J 9.0, 16.8 Hz, 2H), 4.8–5.1 (m, 6H), 7.0–7.1 (m, 4H), 7.2–7.4 (m, 15H).

To a solution of 2,4-di(benzyloxycarbonyl)butyl(4-methylbenzyl)-o-benzylphosphinic acid (0.70 g, 1.2 mmol) in ethanol (30 mL) was added Pd/C (5%, 0.10 g) and the suspension was shaken under hydrogen (50 psi) for 18 h. The suspension was then filtered through a pad of Celite and concentrated under reduced pressure. The resulting residue was dissolved in distilled water (5 mL), passed through a column of AG 50W-X8 resin (H$^+$ form), and lyophilized to give 0.21 g of 2-[[(4-methylbenzyl)hydroxyphosphinyl] methyl]pentanedioic acid (5, R=4-methylbenzyl) as a white solid (55% yield): Rf 0.62 (i-PrOH:H$_2$O, 7:3); $^1$H NMR (D$_2$O) delta 1.7–1.9 (m, 3H), 2.0–2.2 (m, 1H), 2.33 (dt, J =1.7 Hz, 7.4 Hz, 2H), 2.55–2.70 (m, 1H), 3.12 (d, J =16.5 Hz, 2H), 7.0–7.1 (m, 2H), 7.2–7.3 (m, 2H). Anal. Calcd for $C_{13}H_{17}O_6P*0.30H_2O$: C, 52.60; H, 6.18. Found: C, 52.60; H, 6.28.

Example 7
Preparation of 2-[[(4-Fluorobenzyl)hydroxyphosphinyl] methyl]pentanedioic acid (R=4-fluorobenzyl):

Scheme V, prepared as described in the above example where R=methylbenzyl: Rf 0.64 (i-PrOH:H$_2$O, 7:3); $^1$H NMR (D$_2$O) delta 1.7–1.9 (m, 3H), 2.0–2.2 (m, 1H), 2.3–2.4 (m, 2H), 2.5–2.70 (m, 1H), 3.12 (d, J=16.5 Hz, 2H), 7.0–7.1 (m, 2H), 7.2–7.3 (m, 2H). Anal. Calcd for $C_{13}H_{16}FO_6P*0.25H_2O$: C, 48.38; H, 5.15. Found: C, 48.38; H, 5.15.

Example 8
Preparation of 2-[[(4-Methoxybenzyl)hydroxyphosphinyl] methyl]pentanedioic acid (R=4-methoxybenzyl):

Scheme V, prepared as described in the above example where R=methylbenzyl: Rf 0.5G (i-PrOH:H$_2$O, 7:3); $^1$H NMR (D$_2$O) delta 1.8–1.9 (m, 3H), 2.0–2.2 (m, 1H), 2.3–2.4 (m, 2H), 2.55–2.70 (m, 1H), 3.16 (d, J=16.7 Hz, 2H), 3.81 (s, 3H), 6.98 (d, J=8.7 Hz, 2H), 7.25 (d, J=8.7 Hz, 2H). Anal. Calcd for $C_{14}H_{19}O_7P*0.30H_2O$: C, 50.09; H, 5.89. Found: C, 49.98; H, 5.80.

Example 9
Preparation of 2-[[(2-Fluorobenzyl)hydroxyphosphinyl] methyl]-pentanedioic acid (R=2-fluorobenzyl):

Scheme V, prepared as described in the above example where R=methylbenzyl: Rf 0.67 (i-PrOH:H$_2$O, 7:3); $^1$H NMR (D$_2$O) delta 1.8–1.9 (m, 3H), 2.0–2.2 (m, 1H); 2.3–2.4 (m, 2H), 2.55–2.70 (m, 1H), 3.28 (d, J=16.6 Hz, 2H), 7.1–7.5 (m, 4H). Anal. Calcd for $C_{13}H_{16}FO_6P*0.10H_2O$: C, 48.79; H, 5.10. Found: C, 48.84; H, 5.14.

Example 10
Preparation of 2-[[(Pentafluorobenzyl)hydroxyphosphinyl] methyl]pentanedioic acid (R=pentafluorobenzyl):

Scheme V, prepared as described in the above example where R=methylbenzyl: Rf 0.69 (i-PrOH:H$_2$O, 7:3); $^1$H NMR (D$_2$O) delta 1.8–2.0 (m, 3H), 2.1–2.3 (m, 1H), 2.3–2.5 (m, 2H), 2.7–2.9 (m, 1H), 3.29 (d, J=15.4 Hz, 2H), Anal. Calcd for $C_{13}H_{12}F_5O_6P*0.45H_2O$: C, 39.20; H, 3.26. Found: C, 39.17; H, 3.28.

Example 11
Preparation of 2-[(methylhydroxyphosphinyl)methyl] pentanedioic acid Scheme VI, Compound 9

2,4-Di(benzyloxycarbonyl)butylphosphinic acid (6)

Dry phosphinic acid (100 g, 1.52 mol) was dissolved in 100 ml of chloroform and treated with triethylamine (155 g, 1.52 mol). The mixture was evaporated and transferred to a three liter flask, containing 750 mL of chloroform. The solution was stirred by means of a mechanical stirrer and the flask cooled to 0° C. The clear solution was treated with triethylamine (277 g, 2.72 mol) followed by trimethylsilyl chloride (281 g, 2.58 mol). Once addition of trimethylsilyl chloride was complete dibenzyl 2-methylenepentanedioate (2) in 150 mL of chloroform was added dropwise over 20 minutes. The low temperature bath was removed and the mixture warmed to room temperature. After 6 hours the thick slurry was filtered and the filtrate cooled to 0° C. The filtrate was then quenched with 5% hydrochloric acid and the organic layer removed. The aqueous layer was extracted with chloroform, the organics combined, dried (MgSO$_4$) and evaporated under reduced pressure to give 55 g of 2,4-di (benzyloxycarbonyl)butylphosphinic acid (6) as a light yellow liquid. The liquid was purified by flash chromatography and eluted using 3:1 hexanes/ethyl acetate containing 5-trifluoroacetic acid to give 40 g (7%) of the desired product. Rf 0.28 (3:1 Hex./EtOAc 5% TFA); $^1$H NMR (CDCl$_3$): 7.3 ppm (m, 10H), 7.2 ppm (d, 1H), 5.12 ppm (s, 2H), 2.9 ppm (m, 1H), 2.4 ppm (t, 2H), 2.2 ppm (m, 1H), 2.0 ppm (m, 3H).

2,4-Di(benzyloxycarbonyl)butylbenzylphosphinic acid (7)

To a solution of 2,4-di-(benzyloxycarbonyl) butylphosphinic acid (6) (19.3 g, 49.4 mmol) in tetrahydrofuran was added benzyl alcohol (5.3 g, 49.3 mmol) and dimethylamino in tetrahydrofuran was added benzyl alcohol (5.3 g, 49.3 mmol) and dimethylamino pyridine (0.5 g). Dicylcohexylcarbodiimide (DCC, 12 g, 58 mmol) was added and a white precipitate formed. After 30 minutes the white suspension was filtered and the filtrate evaporated under reduced pressure. The clear and colorless oil was purified by flash chromatography and eluted with 1:1 Hex./EtOAc to give 2,4-di(benzyloxycarbonyl) butylbenzylphosphinic acid (7) (11.5 g, 47%) as a clear and colorless oil. Rf. 0.16 (1:1 Hex./EtOAc); $^1$H NMR (CD1C$_3$): 7.3 ppm (m, 15H), 7.2 ppm (d, 1H), 5.0 ppm (m, 6H), 2.9 ppm (m, 1H), 2.2 ppm (m, 3H), 1.9 ppm (m, 3H).

2,4-Di(benzyloxycarbonyl)butyl[hydroxy(phenyl)methyl] benzylphosphinic acid (8)

2,4-Di(benzyloxycarbonyl)butylbenzylphosphinic acid (7) in 5 mL of dry THF was added dropwise to a stirring cooled (0° C.) mixture of sodium hydride (0.09 g, 2.3 mmol) in 15 mL of THF. After 15 minutes benzaldehyde (0.23 g, 2.2 mmol) was added via syringe while maintaining a temperature of 0° C. After 30 minutes the mixture was quenched with water and extracted with two portions of dichloromethane. The organics were combined and evaporated to give a clear colorless oil. The oil was chromatographed on silica and eluted with a 1:1 Hex./EtOAc solvent system. The desired fractions were collected and evaporated to give 0.4 g (33%) of 2,4-di(benzyloxycarbonyl)butyl[hydroxy (phenyl)methyl]benzylphosphinic acid (6) as a clear and colorless oil. Rf 0.18 (1:1 Hex./EtOAc);

$^1$H NMR (CDCl$_3$): 7.3 ppm (m, 20H), 5.2 ppm (m, 1H), 4.9 ppm (m, 6H), 2.8 ppm (dm, 1H), 2.2 ppm (m, 3H), 1.9 ppm (m, 3H).

2-([Hydroxy(phenyl)methyl]hydroxyphosphinylmethyl) pentanedioic acid (9)

2,4-Di(benzyloxycarbonyl)butyl[hydroxy(phenyl) methyl]benzylphosphinic acid (6)(0.37 g, 0.6 mmol) in 25 mL of water containing 0.10 g of 10% Pd/C was hydrogenated at 40 psi for 6 hours. The mixture was filtered through a pad of Celite and lyophilized to give 2-([hydroxy(phenyl) methyl]hydroxyphosphinylmethyl)pentanedioic acid (9) (0.14 g, 70%) as a white solid.

$^1$H NMR (D2O): 7.4 ppm (m, 5H), 5.0 ppm (d, 1H), 2.7 ppm (m, 1H), 2.4 ppm (m, 2H), 2.2 ppm (m, 1H), 1.9 ppm (m, 3H).

Element Analysis: Calculated $C_{13}H_{17}O_7P\cdot0.6H_2O$: C, 47.74 H, 5.61 Found: C, 47.73 H, 5.68.

Example 12

Preparation of Dibenzyl 2-Methylenepentanedioate.
Scheme III.

Benzyl acrylate (500 g, 3 mol) was heated to 100° C. under an atmosphere of nitrogen. The heating was stopped and HMPT (10 g, 61 mmol) was added dropwise while maintaining an internal temperature of 135–145° C. Once addition was complete the mixture was cooled to room temperature and a slurry of silica with 5:1 Hex/EtOAc was added. The slurry was then transferred to a column containing a plug of dry silica. The column was then washed with 1:1 Hex/EtOAc and the solvent was collected and evaporated. The clear yellow liquid was distilled under high vacuum (200 µHg) to give an initial fraction of 8 g distilling at 45° C. and then the desired product at 180–185° C. (212 g, 42%) as a clear and colorless liquid.

1H-NMR (CDCl$_3$) 7.3 ppm (s, 10H); 6.2 ppm (s, 1H); 5.5 ppm (s, 1H); 5.2 ppm (s, 2H); 5.1 ppm (s, 2H); 2.5 ppm (m, 4H).

Example 13

Preparation of Dibenzyl 2-[[Bis(benzyloxy)phosphoryl] methyl]pentanedioate.
Scheme III Dibenzyl phosphite (9.5 g, 36 mmol) in 350 ml of dichloromethane was cooled to 0° C. To this stirring solution was added trimethyl aluminum (18.2 ml, 2.0M solution in hexane, 36.4 mmol). After 30 minutes 1 (6.0 g, 37 mmol) in 90 ml of dichloromethane was added dropwise over 10 minutes. The clear and colorless solution was then warmed to room temperature and left to stir overnight. The mixture was then quenched by the slow addition of 5% HCl. After stirring an additional 1.5 hours the lower organic layer was removed and the aqueous layer extracted once with 100 ml of dichloromethane. The organics were combined, dried (MgSO$_4$), and evaporated to give a clear light golden liquid. The liquid was chromatographed on silica gel (4 cm*30 cm) and eluted with a gradient (4:1–1:1) solvent system (Hexane/EtOAc). The fractions containing the desired product were combined and evaporated to yield 2 (7.1 g, 42%) as a clear and colorless liquid. The liquid was then distilled on a Kughleror apparatus at 0.5 mm Hg and 195–200° C. The distillate was discarded and the remaining light golden oil was chromatographed on silica gel (1:1, Hex./EtOAc) to give 2.9 g of 2 as a clear and colorless oil. TLC R$_f$ 0.5 (1:1, Hex./EtOAc).

1H-NMR (CDCl$_3$) 7.1–7.4 (m, 20H); 5.05 (s, 2H); 4.8–5.03 (m, 6H); 2.8 (1H); 2.22–2.40 (m, 3H); 1.80–2.02 (m, 3H).

Example 14

Preparation of 2-(Phosphonomethyl)pentanedioic acid.
Scheme III

The benzyl pentanedioate (2.9 g, 4.9 mmol) was added to a mixture of 20 ml of methanol containing 0.29 g (6 mol %) of 10% Pd/C. This mixture was hydrogenated on a Parr hydrogenator at 40 psi for 24 hours, filtered and evaporated to give 3 (1.0 g, 90%) as a clear slightly golden viscous oil.

1H-NMR (D$_2$O) 2.6–2.78 (m, 1H); 2.25–2.40 (m, 2H); 1.75–2.15 (m, 4H).

Example 15

A patient is diagnosed with adenocarcinoma of the prostate. The patient may then be administered a NAALADase inhibitor, such as set forth in examples 1 through 3, by direct injection into the tumor. After this initial treatment, the patient may be optionally administered the same or different NAALADase inhibitor by intermittent or continuous administration by subdural pump. It would be expected that no further occurrences of the adenocarcinoma would develop.

Example 16

A patient is diagnosed with adenocarcinoma of the prostate. The patient may then be administered a NAALADase inhibitor, such as set forth in examples 1 through 3, by direct injection into the tumor. After this initial treatment, the patient may be optionally administered the same or different NAALADase inhibitor by intermittent or continuous administration by implantation of a biocompatible, polymeric matrix delivery system. It would be expected that no further occurrences of the adenocarcinoma would develop.

Example 17

A patient is diagnosed with benign prostatic hyperplasia. The patient may then be administered a NAALADase inhibitor, such as set forth in examples 1 through 3, by direct injection into the tumor. After this initial treatment, the patient may be optionally administered the same or different NAALADase inhibitor by intermittent or continuous administration by injection, subdural pump, or polymeric matrix implant. It would be expected that the benign prostatic hyperplastic cells do not develop into carcinoma.

Example 18

A patient is diagnosed with adenocarcinoma of the prostate. The adenocarcinoma appears not to have metastasized. The adenocarcinoma would be removed by surgery. After post-operative recovery, the patient would be locally administered NAALADase inhibitor by intermittent or continuous administration by injection, subdural pump or by polymeric matrix implant. It would expected that no further occurrences of the carcinoma would develop.

Example 19

A patient is diagnosed with metastatic adenocarcinoma of the prostate. The adenocarcinoma appears to have metastasized, but surgery still is indicated as an effective treatment modality. Tumor tissue would be removed by surgery.

The patient would be locally administered a NAALADase inhibitor such as described herein from the time, approximately, of the initial diagnosis and would continue after surgery. After post-operative recovery, the patient would be maintained at this level of NAALADase inhibitor by a regimen of periodic local administration. The patient would be monitored carefully for intolerable adverse side-effects of NAALADase inhibitor administration. It would be expected that no further tumors develop. If some of the original, small tumorous masses are detected after surgery, they would be expected to not grow in size.

Example 20

A patient is diagnosed with ACTH-producing tumors. The patient may then be administered a NAALADase inhibitor, such as set forth in examples 1 through 3, by direct injection into the tumor. After this initial treatment, the patient may be optionally administered the same or different NAALADase inhibitor by direct injection, subdural pump, or implantation of a biocompatible, polymeric matrix delivery system. It would be expected that tumor growth or tumor cell growth would be prevented or inhibited and that no further occurrences of the ACTH-producing tumor would develop.

Example 21

A treatment such as that described in Example 9 wherein the patient is diagnosed with acute lymphocytic leukemia.

Example 22

A treatment such as that described in Example 9 wherein the patient is diagnosed with acute non-lymphocytic leukemia.

Example 23

A treatment such as that described in Example 9 wherein the patient is diagnosed with metastatic or non-metastatic cancer of the adrenal cortex.

Example 24

A treatment such as that described in Example 9 wherein the patient is diagnosed with metastatic or non-metastatic bladder cancer.

Example 25

A treatment such as that described in Example 9 wherein the patient is diagnosed with metastatic or non-metastatic brain cancer.

Example 26

A treatment such as that described in Example 9 wherein the patient is diagnosed with metastatic or non-metastatic breast cancer.

Example 27

A treatment such as that described in Example 9 wherein the patient is diagnosed with metastatic or non-metastatic cervical cancer.

Example 28

A treatment such as that described in Example 9 wherein the patient is diagnosed with metastatic or non-metastatic chronic lymphocytic leukemia.

Example 29

A treatment such as that described in Example 9 wherein the patient is diagnosed with metastatic or non-metastatic chronic myelocytlc leukemia.

Example 30

A treatment such as that described in Example 9 wherein the patient is diagnosed with metastatic or non-metastatic colorectal cancer.

Example 31

A treatment such as that described in Example 9 wherein the patient is diagnosed with metastatic or non-metastatic cutaneous T-cell lymphoma.

Example 32

A treatment such as that described in Example 9 wherein the patient is diagnosed with metastatic or non-metastatic endometrial cancer.

Example 33

A treatment such as that described in Example 9 wherein the patient is diagnosed with metastatic or non-metastatic esophageal cancer.

Example 34

A treatment such as that described in Example 9 wherein the patient is diagnosed with metastatic or non-metastatic Ewing's sarcoma.

Example 35

A treatment such as that described in Example 9 wherein the patient is diagnosed with metastatic or non-metastatic gallbladder cancer.

Example 36

A treatment such as that described in Example 9 wherein the patient is diagnosed with metastatic or non-metastatic hairy cell leukemia.

Example 37

A treatment such as that described in Example 9 wherein the patient is diagnosed with metastatic or non-metastatic head and neck cancer.

Example 38

A treatment such as that described in Example 9 wherein the patient is diagnosed with metastatic or non-metastatic Hodgkin's lymphoma.

Example 39

A treatment such as that described in Example 9 wherein the patient is diagnosed with metastatic or non-metastatic Kaposi's sarcoma.

Example 40

A treatment such as that described in Example 9 wherein the patient is diagnosed with metastatic or non-metastatic kidney cancer.

Example 41

A treatment such as that described in Example 9 wherein the patient is diagnosed with metastatic or non-metastatic liver cancer.

Example 42

A treatment such as that described in Example 9 wherein the patient is diagnosed with metastatic or non-metastatic lung cancer (small cell and/or non-small cell).

Example 43

A treatment such as that described in Example 9 wherein the patient is diagnosed with metastatic or non-metastatic malignant peritoneal effusion.

Example 44

A treatment such as that described in Example 9 wherein the patient is diagnosed with metastatic or non-metastatic malignant pleural effusion.

Example 45

A treatment such as that described in Example 9 wherein the patient is diagnosed with metastatic or non-metastatic melanoma.

Example 46

A treatment such as that described in Example 9 wherein the patient is diagnosed with metastatic or non-metastatic mesothelioma.

Example 47

A treatment such as that described in Example 9 wherein the patient is diagnosed with metastatic or non-metastatic multiple myeloma.

Example 48

A treatment such as that described in Example 9 wherein the patient is diagnosed with metastatic or non-metastatic neuroblastoma.

Example 49

A treatment such as that described in Example 9 wherein the patient is diagnosed with metastatic or non-metastatic non-Hodgkin's lymphoma.

Example 50

A treatment such as that described in Example 9 wherein the patient is diagnosed with metastatic or non-metastatic osteosarcoma.

Example 51

A treatment such as that described in Example 9 wherein the patient is diagnosed with metastatic or non-metastatic ovarian cancer (and/or germ cell ovarian cancer).

Example 52

A treatment such as that described in Example 9 wherein the patient is diagnosed with metastatic or non-metastatic pancreatic cancer.

Example 53

A treatment such as that described in Example 9 wherein the patient is diagnosed with metastatic or non-metastatic penis cancer.

Example 54

A treatment such as that described in Example 9 wherein the patient is diagnosed with metastatic or non-metastatic retinoblastoma.

Example 55

A treatment such as that described in Example 9 wherein the patient is diagnosed with metastatic or non-metastatic skin cancer.

Example 56

A treatment such as that described in Example 9 wherein the patient is diagnosed with metastatic or non-metastatic soft-tissue sarcoma.

Example 57

A treatment such as that described in Example 9 wherein the patient is diagnosed with metastatic or non-metastatic squamous cell carcinoma.

Example 58

A treatment such as that described in Example 9 wherein the patient is diagnosed with metastatic or non-metastatic stomach cancer.

Example 59

A treatment such as that described in Example 9 wherein the patient is diagnosed with metastatic or non-metastatic testicular cancer.

Example 60

A treatment such as that described in Example 9 wherein the patient is diagnosed with metastatic or non-metastatic thyroid cancer.

Example 61

A treatment such as that described in Example 9 wherein the patient is diagnosed with metastatic or non-metastatic trophoblastic neoplasm.

Example 62

A treatment such as that described in Example 9 wherein the patient is diagnosed with metastatic or non-metastatic uterine cancer.

Example 63

A treatment such as that described in Example 9 wherein the patient is diagnosed with metastatic or non-metastatic vaginal cancer.

Example 64

A treatment such as that described in Example 9 wherein the patient is diagnosed with metastatic or non-metastatic cancer of the vulva.

Example 65

A treatment such as that described in Example 9 wherein the patient is diagnosed with metastatic or non-metastatic Wilm's tumor.

The invention being thus described, it will be obvious that the same may be varied in many ways. Such variations are not to be regarded as a departure from the spirit and scope of the invention and all such modification are intended to be included within the scope of the following claims.

What is claimed is:

1. A method of treating cancer in an animal which comprises:
   administering to an animal suffering from a cancer an effective amount of a NAALADase inhibitor, wherein the cancerous tissue or associated neovasculature contains NAALADase.

2. The method of claim 1 wherein the cancer is selected from the group consisting of: ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, retinoblastoma, skin cancer, soft tissue sarcoma, squamous cell carcinomas, stomach cancer, testicular cancer, thyroid cancer, trophoblastic neoplasms, cancer of the uterus, vaginal cancer, cancer of the vulva, and Wilm's tumor.

3. The method of claim 1 wherein the cancer is selected from the group consisting of: brain cancer, cancer of the adrenal cortex, kidney cancer, and testicular cancer.

4. A method of inhibiting tumor cell growth in an animal which comprises: administering to an animal suffering from a tumor cell growth an effective amount of a NAALADase inhibitor, wherein the tumor or associated neovasculature contains NAALADase.

5. The method of claim 4 wherein the tumor is selected from the group consisting of: ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, retinoblastoma, skin cancer, soft tissue sarcoma, squamous cell carcinomas, stomach cancer, testicular cancer, thyroid cancer, trophoblastic neoplasms, cancer of the uterus, vaginal cancer, cancer of the vulva, and Wilm's tumor.

6. The method of claim 4 wherein the tumor is selected from the group consisting of: brain cancer, cancer of the adrenal cortex, kidney cancer, and testicular cancer.

7. A method of treating cancer in an animal which comprises:
   administering to an animal suffering from a cancer an effective amount of a NAALADase inhibitor, wherein the diseased tissue contains NAALADase.

8. The method of claim 7 wherein the cancer is selected from the group consisting of: ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, retinoblastoma, skin cancer, soft tissue sarcoma, squamous cell carcinomas, stomach cancer, testicular cancer, thyroid cancer, trophoblastic neoplasms, cancer of the uterus, vaginal cancer, cancer of the vulva, and Wilm's tumor.

9. The method of claim 8 wherein the cancer is selected from the group consisting of: brain cancer, cancer of the adrenal cortex, kidney cancer, and testicular cancer.

10. A method of treating cancer in an animal which comprises:
    administering to an animal suffering from a cancer an effective amount of a NAALADase inhibitor, wherein NAALADase is inhibited in the animal.

11. The method of claim 10 wherein the cancer is selected from the group consisting of: ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (gem cell) cancer, pancreatic cancer, penis cancer, retinoblastoma, skin cancer, soft tissue sarcoma, squamous cell carcinomas, stomach cancer, testicular cancer, thyroid cancer, trophoblastic neoplasms, cancer of the uterus, vaginal cancer, cancer of the vulva, and Wilm's tumor.

12. The method of claim 11 wherein the cancer is selected from the group consisting of: brain cancer, cancer of the adrenal cortex, kidney cancer, and testicular cancer.

* * * * *